US008680327B2

(12) United States Patent
Endres et al.

(10) Patent No.: US 8,680,327 B2
(45) Date of Patent: Mar. 25, 2014

(54) METHODS FOR MANUFACTURING TETRANOR-PROSTAGLANDIN D, J, E, A AND F METABOLITES

(75) Inventors: Gregory W. Endres, Saline, MI (US); Andriy M. Kornilov, Ypsilanti, MI (US); Adam Uzieblo, Farmington Hills, MI (US)

(73) Assignee: Cayman Chemical Company, Incorporated, Ann Arbor, MI (US)

( * ) Notice: Subject to any disclaimer, the term of this patent is extended or adjusted under 35 U.S.C. 154(b) by 305 days.

(21) Appl. No.: 13/160,483

(22) Filed: Jun. 14, 2011

(65) Prior Publication Data

US 2012/0041229 A1 Feb. 16, 2012

Related U.S. Application Data

(60) Provisional application No. 61/354,489, filed on Jun. 14, 2010.

(51) Int. Cl.
*C07C 405/00* (2006.01)
*C07C 51/347* (2006.01)
*C07C 59/82* (2006.01)

(52) U.S. Cl.
USPC ........................................ 562/504

(58) Field of Classification Search
None
See application file for complete search history.

(56) References Cited

U.S. PATENT DOCUMENTS

| 3,944,593 | A | 3/1976 | Nelson |
| 3,992,413 | A | 11/1976 | Taub et al. |
| 7,166,730 | B2 | 1/2007 | Gutman et al. |

FOREIGN PATENT DOCUMENTS

WO WO 2009/043015 A1 4/2009

OTHER PUBLICATIONS

Lin, C.H., "Prostaglandin Metabolites, Synthesis of E and F Urinary Metabolites", Journal of Organic Chemistry, 1976, pp. 4045-4047, vol. 41, No. 25.
Granstrom, E. et al., "The Structure of a Urinary Metabolite of Prostaglandin, F20 in Man", Journal of the American Chemical Society, 1969, pp. 3398-3400, vol. 91.
Cayman Chemical, Product Information, Tetranor-PGDM, Item No. 12850, 2011.
Cayman Chemical, Product Information, Tetranor-PGDM-d6, Catalog No. 10009039, 2008.
Cayman Chemical, Product Information, Tetranor-PGEM, Catalog No. 14840, 2010.
Cayman Chemical, Product Information, Tetranor-PGEM-d6, Catalog No. 314840, 2008.
Cayman Chemical, Product Information, Tetranor-PGFM, Catalog No. 16840, 2010.
Prakash, C. et al., "Synthesis of the Major Urinary Metabolite of Prostaglandin D2", Journal of Chemical Society Perkin Trans., 1988, pp. 2821-2826.
Neale, J.R. et al., "Liquid chromatography-tandem mass spectrometric quantification of the dehydration product of tetranor PGE-M, the major urinary metabolite of prostaglandin E(2) in human urine", Journal of Chromatography B, 2008, 871(1), pp. 72-77.
International Search Report for Application No. PCT/US2011/040408 dated Feb. 17, 2012, 2 pages.
D.C. Monkhouse et al., Kinetics of Dehydration and Isomerization of Prostaglandins E1 and E2; Journal of Pharmaceutical Sciences, vol. 62, No. 4, 1973; pp. 576-580.
European Extended Search Report for Application No. EP 11 79 6329 dated Nov. 12, 2013, 7 pages.

*Primary Examiner* — Yevegeny Valenrod
(74) *Attorney, Agent, or Firm* — Howard & Howard Attorneys PLLC

(57) ABSTRACT

The present invention generally relates to synthetic methods for preparing tetranor-prostaglandin D, J, E, A, and F metabolites.

13 Claims, 41 Drawing Sheets

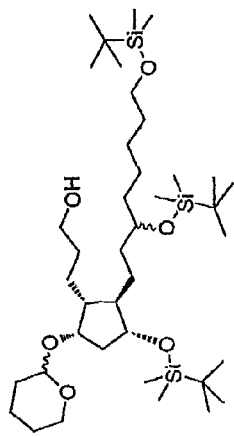
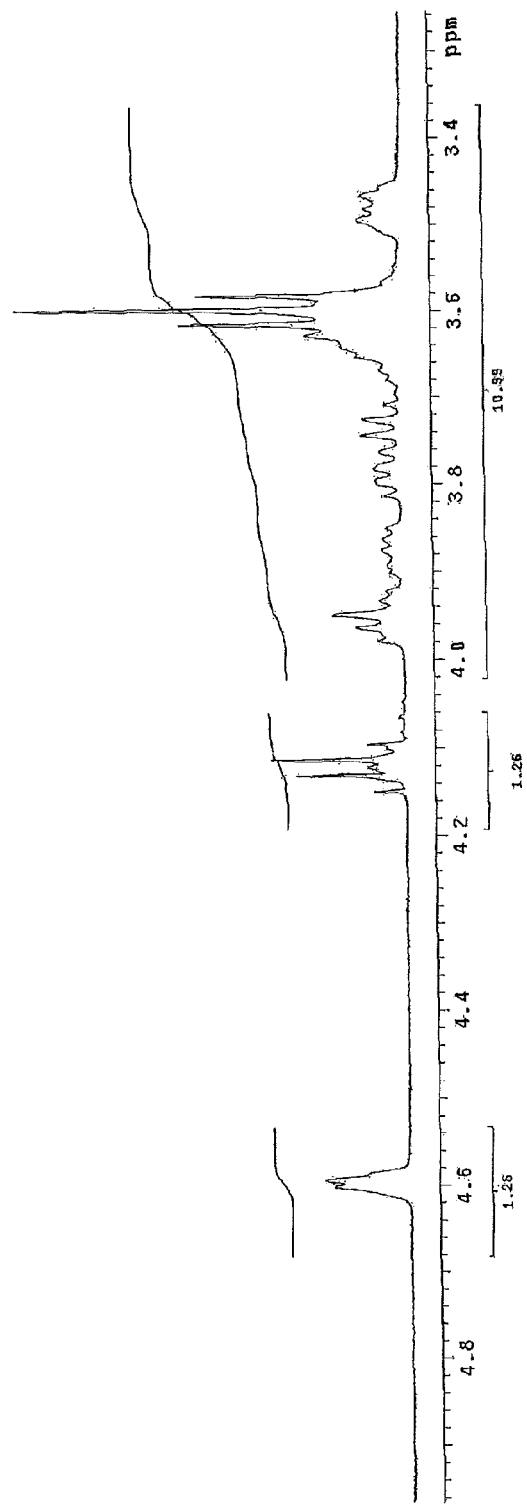
Figure 8B
Compound 11A
3.3–4.9 ppm $C_{39}H_{82}O_6Si_3$
MW: 731.32
Compound 11A
0-2.3 ppm

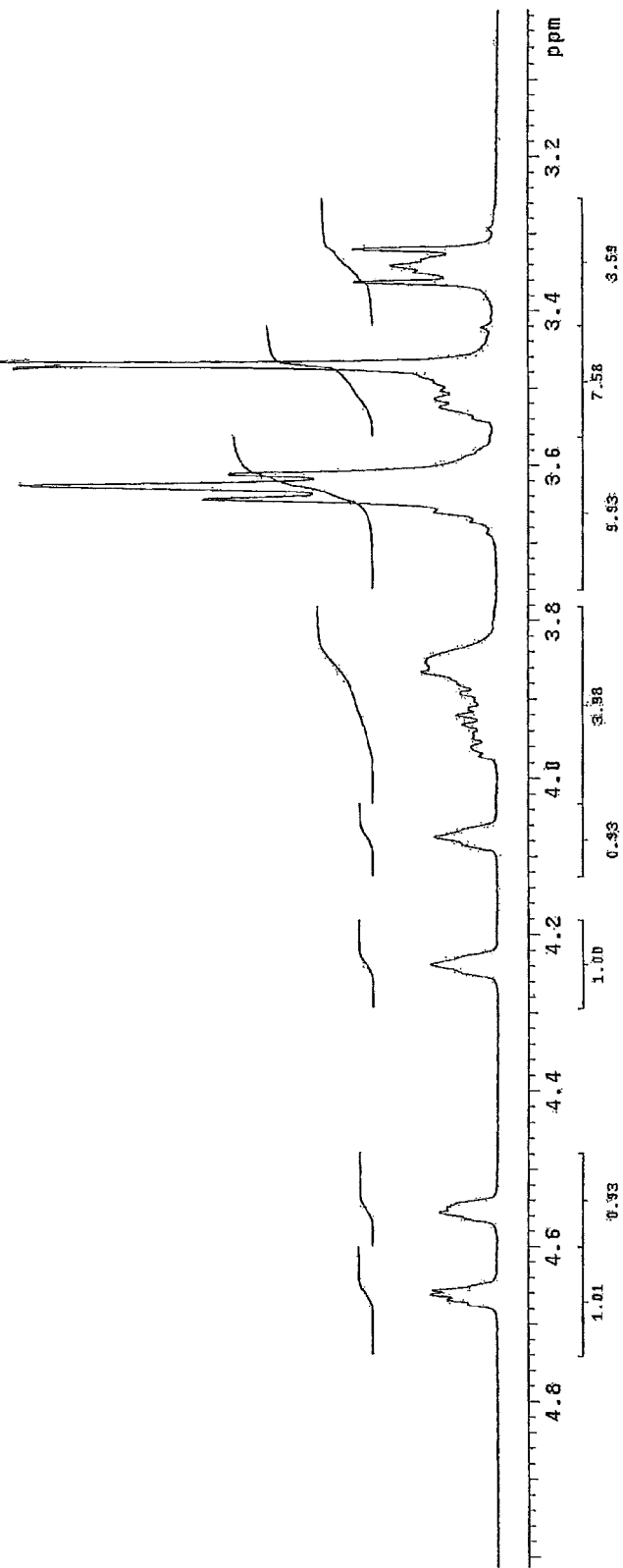
Figure 9B
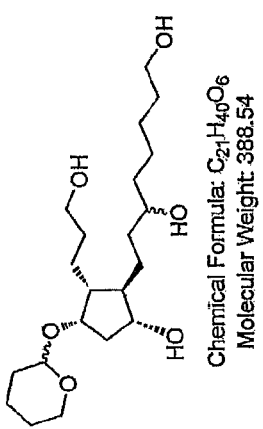
Chemical Formula: $C_{21}H_{40}O_6$
Molecular Weight: 388.54
Compound 12
3.0-5.0 ppm Compound 12
0.6–2.6 ppm Chemical Formula: $C_{21}H_{32}O_8$
Molecular Weight: 412.47

Compound 13

Chemical Formula: $C_{21}H_{32}O_8$
Molecular Weight: 412.47

Compound 13
0.8-4.8 ppm

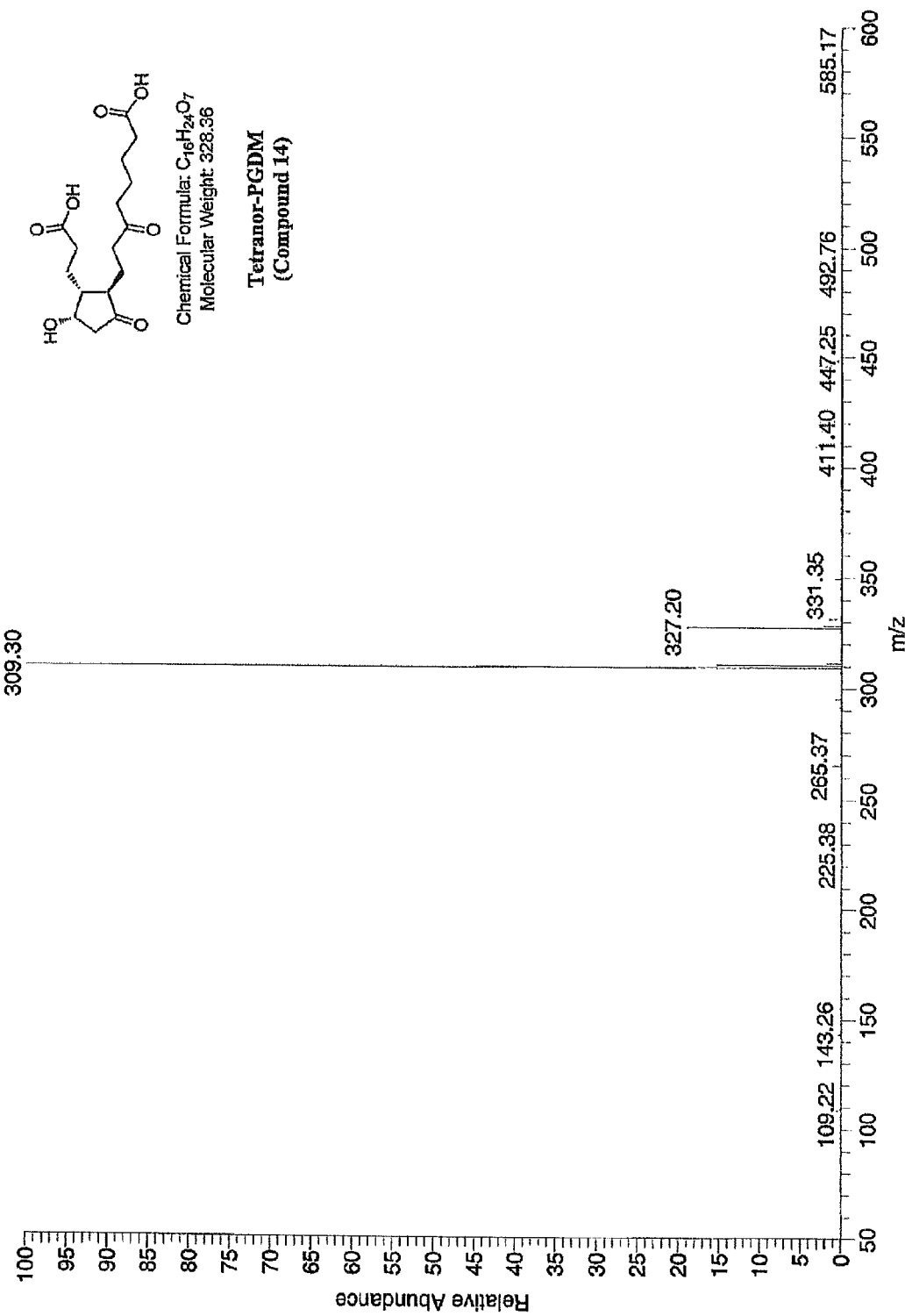

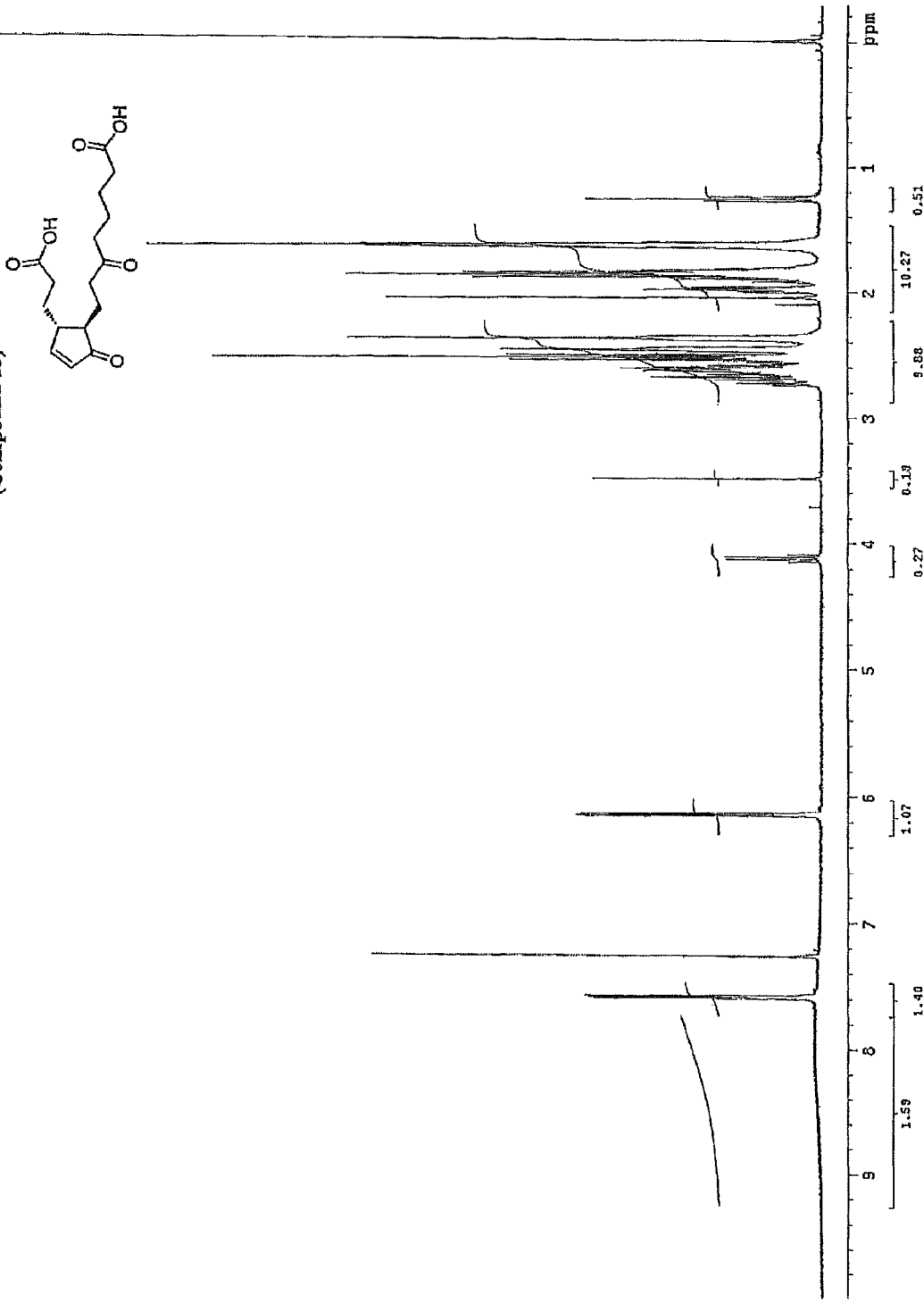

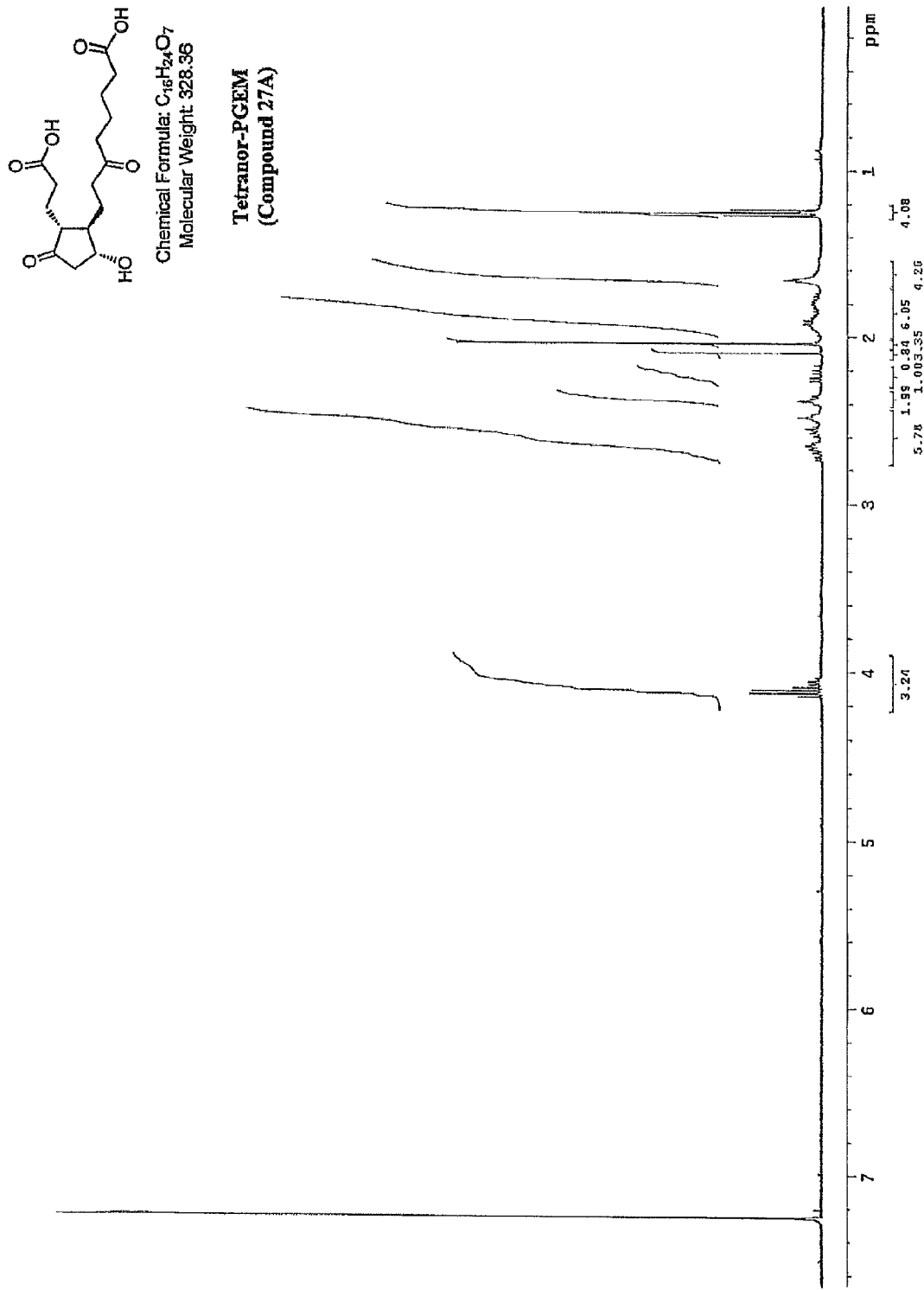

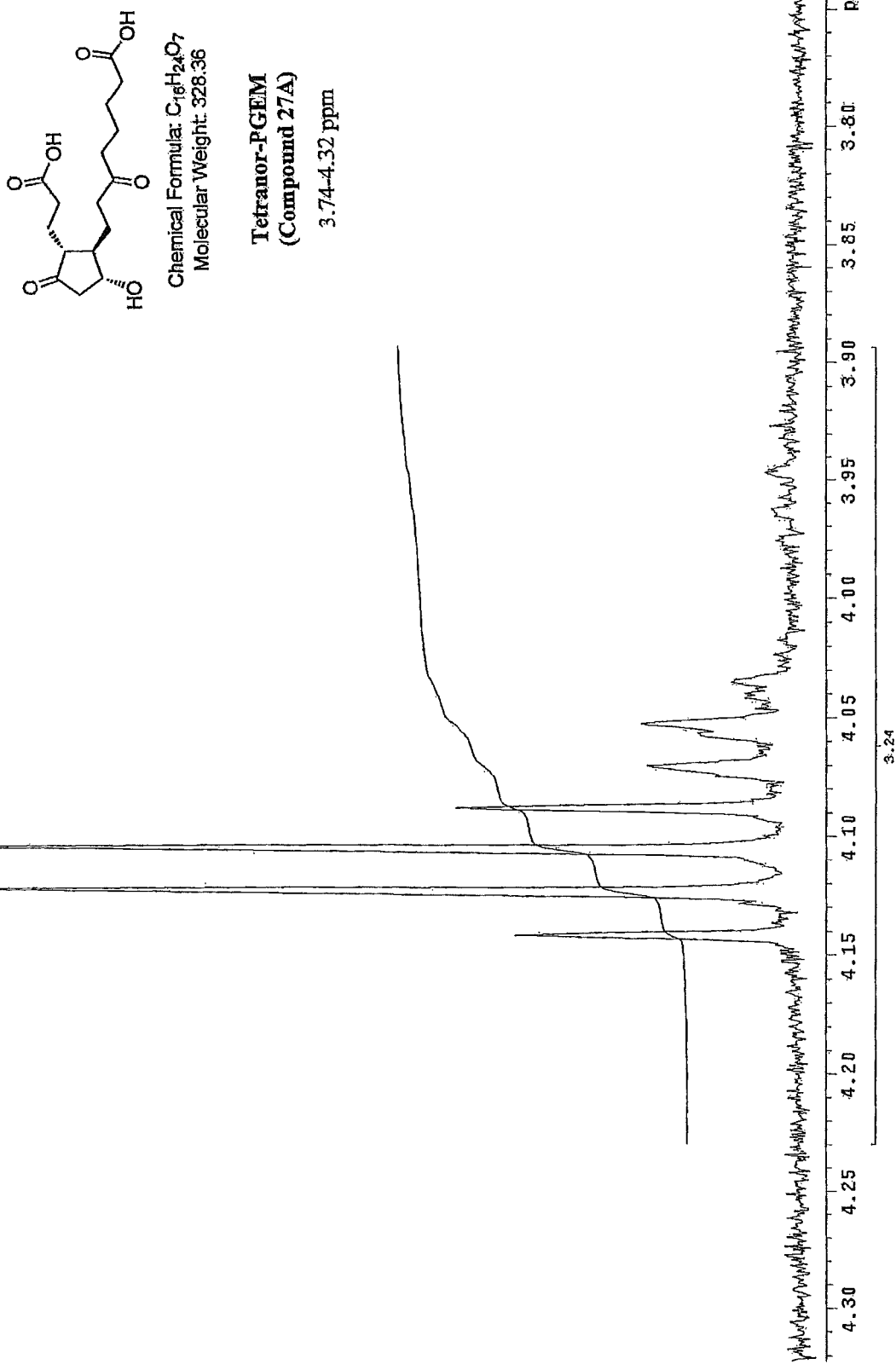

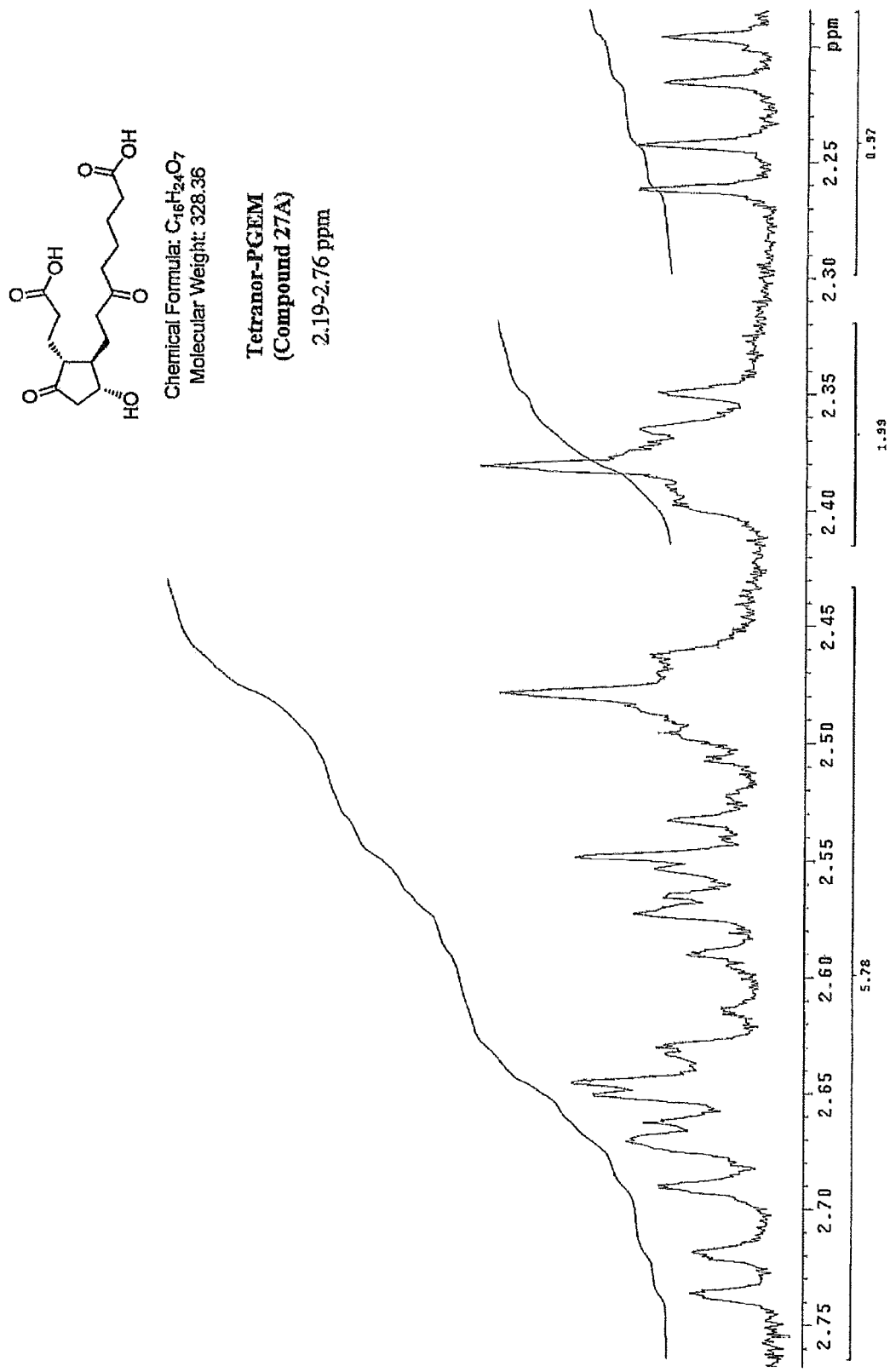

Tetranor-PGEM (Compound 27A)
1.48-2.00 ppm

Tetranor-PGAM
(Compound 28A)

Chemical Formula: $C_{16}H_{22}O_6$
Molecular Weight: 310.34

Tetranor-PGAM (Compound 28A)
5.3–8.0 ppm

Chemical Formula: C₁₆H₂₂O₅
Molecular Weight: 310.34

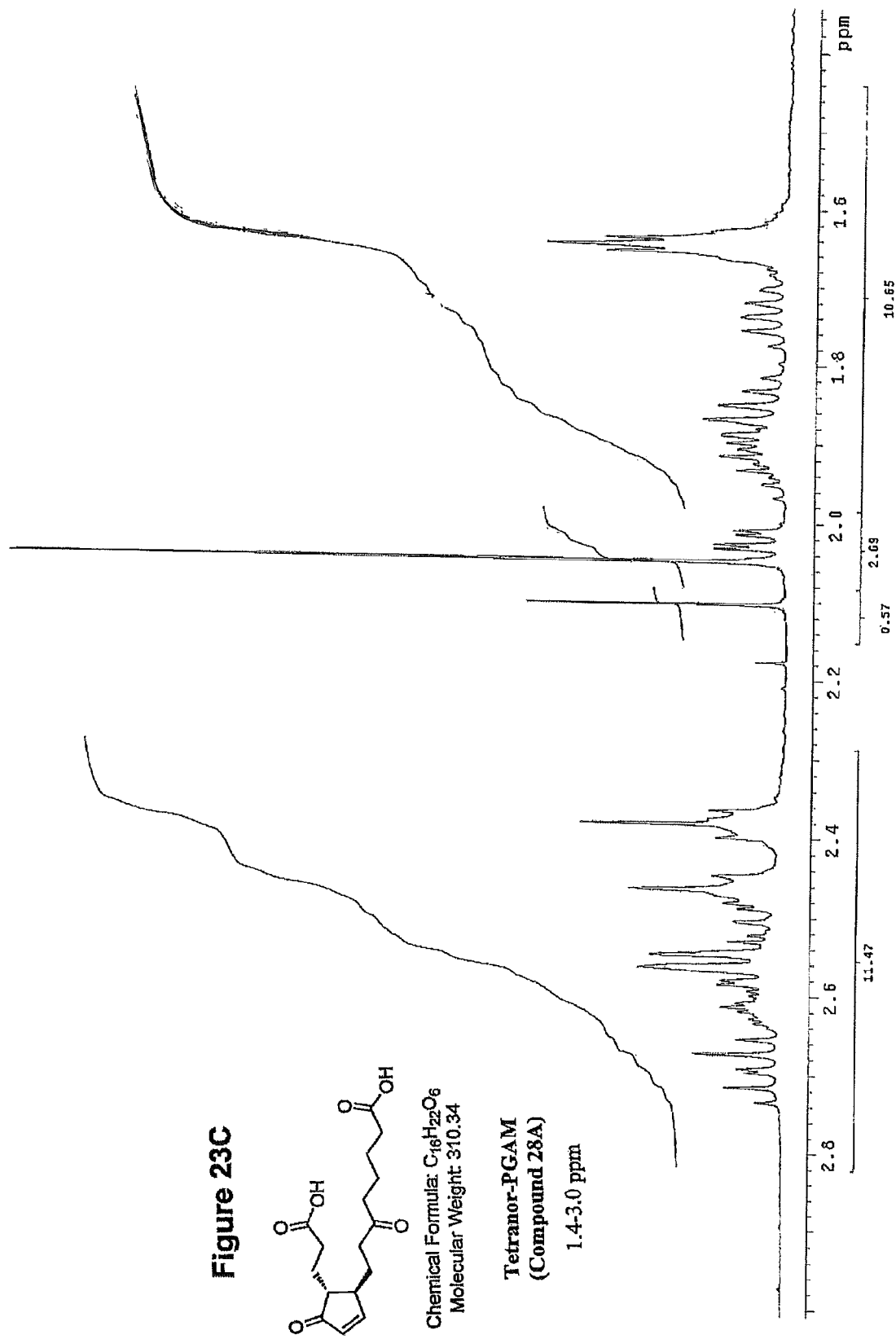

Compound 29, wherein R² is methyl and R³ is tert-butyl

Compound 29, wherein R² is methyl and R³ is *tert*-butyl 3.1-6.1 ppm

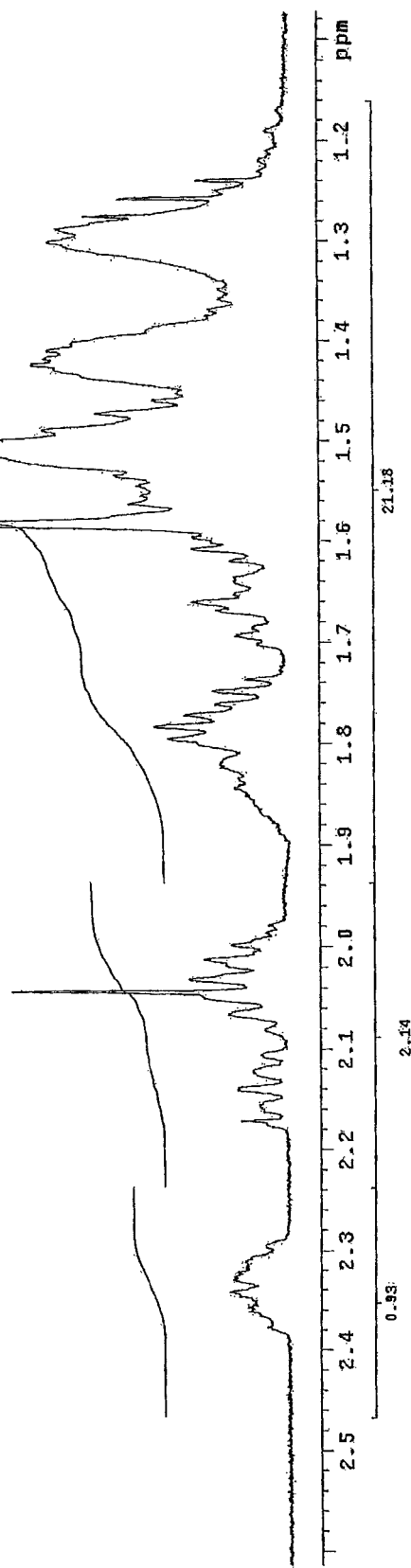
Figure 25C
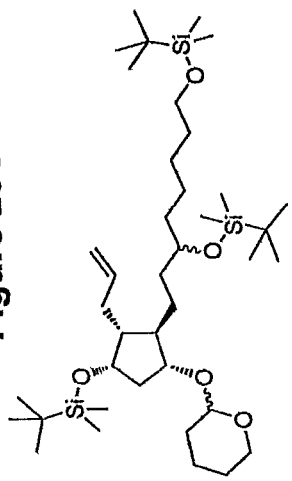
Compound 29,
wherein R² is methyl and R³ is *tert*-butyl
1.1-2.6 ppm

METHODS FOR MANUFACTURING TETRANOR-PROSTAGLANDIN D, J, E, A AND F METABOLITES

CROSS REFERENCE TO RELATED APPLICATIONS

The present application claims priority from U.S. Provisional Application Ser. No. 61/354,489, filed Jun. 14, 2010, which is herein incorporated by reference.

FIELD OF THE INVENTION

The present invention generally relates to synthetic methods for preparing tetranor-prostaglandin D, J, E, A, and F metabolites.

BACKGROUND OF THE INVENTION

Prostaglandins are found in virtually all tissues and glands and are extremely potent mediators of a diverse group of physiological processes (Funk, C. D. *Science*, 2001, 294, 1871-1875). Prostaglandins can participate in a wide range of body functions, such as the contraction and relaxation of smooth muscle (Andersson, K. E., Forman, A. *Acta Pharmacol. Toxicol.*, 1978, 43 (Suppl. 2), 90-95), the dilation and constriction of blood vessels (Abramovich, D. R., Page, K. R., Parkin, A. M. L. *Br. J. Pharmac.*, 1984, 81, 19-21), control of blood pressure (Anderson, R. J., Berl, T., McDonald, K. M., Schrier, R. W. *Kidney International*, 1976, 10, 205-215), and modulation of inflammation and immunity (Hata, A. N., Breyer, R. M. *Pharmacol. Ther.*, 2004, 103(2), 147-166). In general, prostaglandins and related compounds are transported out of the cells that synthesize them and affect other target cells close to their site of formation, mainly by interacting with the target cell's prostaglandin receptors to stimulate or inhibit some target cell function. They also alter the activities of the cells in which they are synthesized. The nature of these effects may vary from one cell type to another, and from the target cell type.

Prostaglandin $D_2$ ($PGD_2$) and $PGE_2$ are biosynthesized from the cyclooxygenase (COX) product of arachidonic acid and common prostanoid precursor prostaglandin $H_2$ ($PGH_2$) by the catalytic action of a class of prostaglandin synthases that includes the prostaglandin D synthases (PGDSs) and the PGESs, respectively. Methods and products exist for the measurement of $PGD_2$ and $PGE_2$ levels in samples derived from biological systems; however, their relative scarcity in urine due to rapid metabolism and degradation makes their use as biofluid markers for measurement of their biosyntheses impractical.

The relatively abundant $PGD_2$ and $PGE_2$ urinary metabolites tetranor-PGDM and tetranor-PGEM, respectively, are favorable quantification species for the assessment of $PGD_2$ and $PGE_2$ biosyntheses. All four species, $PGD_2$, tetranor-PGDM, $PGE_2$, and tetranor-$PGE_2$ readily dehydrate to their cyclopentenone derivatives $PGJ_2$, tetranor-PGJM, $PGA_2$, and tetranor-PGAM, respectively. In addition, the major urinary metabolite of the prostaglandin $PGF_{2\alpha}$ is tetranor-PGFM (Granström, E., Samuelsson, B., *J. Am. Chem. Soc.*, 91, 1969, 3398-3400.).

One synthesis of tetranor-PGEM is disclosed (Lin, C., *J. Org. Chem.*, 41(25), 1976, 4045-4047). The disclosed route began from lactone-aldehyde intermediate (I).

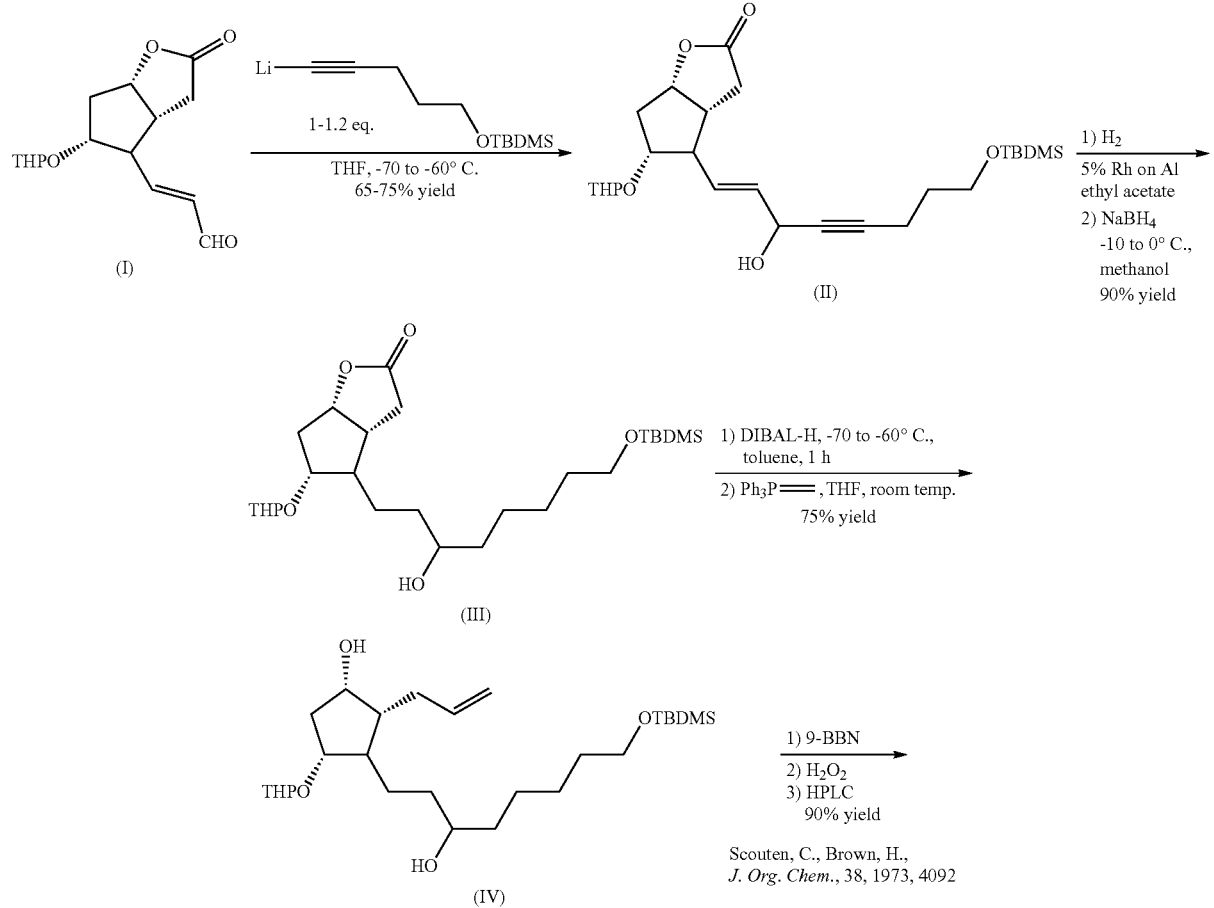

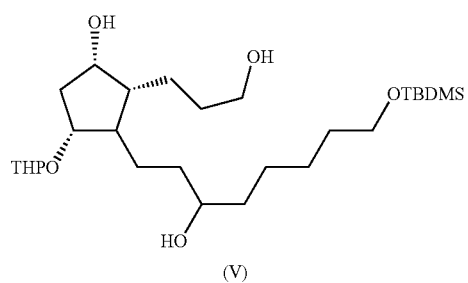

(V)

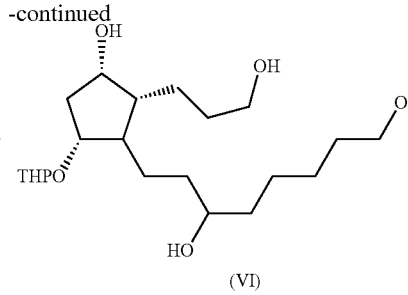

(VI)

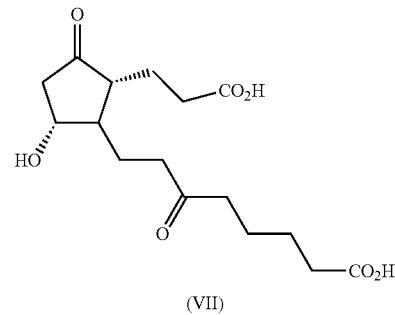

(VII)

tetranor-PGEM

The disclosed route involves process for installing the prostaglandin metabolite lower chain (ω-chain) starting with (I), an intermediate that is not readily available. The ω-chain is further extended by addition of 1-dimethyl-tert-butylsilyloxy-4-pentynyllithium. Other than this disclosure, practical chemical syntheses of the tetranor-prostaglandin metabolites are not disclosed. Ready supplies of these important metabolites by controlled chemical processes would provide advantage over the current art of isolation through biosynthesis. Characterized standard compounds are potentially useful, for example, as assay standards or building blocks for preparing analogs for medicinal chemistry purposes. This present invention provides many practical chemical syntheses of the tetranor-prostaglandin metabolites beginning with the readily available hydroxyl-protected Corey lactone aldehyde.

SUMMARY OF THE INVENTION

The exemplary embodiments may be directed to methods for synthesizing tetranor-prostaglandin D, J, E, A, and F metabolites (tetranor-PGDM, tetranor-PGJM, tetranor-PGEM, tetranor-PGAM, and tetranor-PGFM).

The exemplary embodiments may also be directed to novel synthetic intermediates.

Other exemplary embodiments of the invention will become apparent from the detailed description provided hereinafter. It should be understood that the detailed description and specific examples, while disclosing exemplary embodiments of the invention, are intended for purposes of illustration only and are not intended to limit the scope of the invention.

BRIEF DESCRIPTION OF THE DRAWINGS

FIGS. 1-25D are compound spectra confirming the synthesis for certain compounds described in Schemes I, II and III and the Examples below.

DETAILED DESCRIPTION OF THE INVENTION

Figure 1:
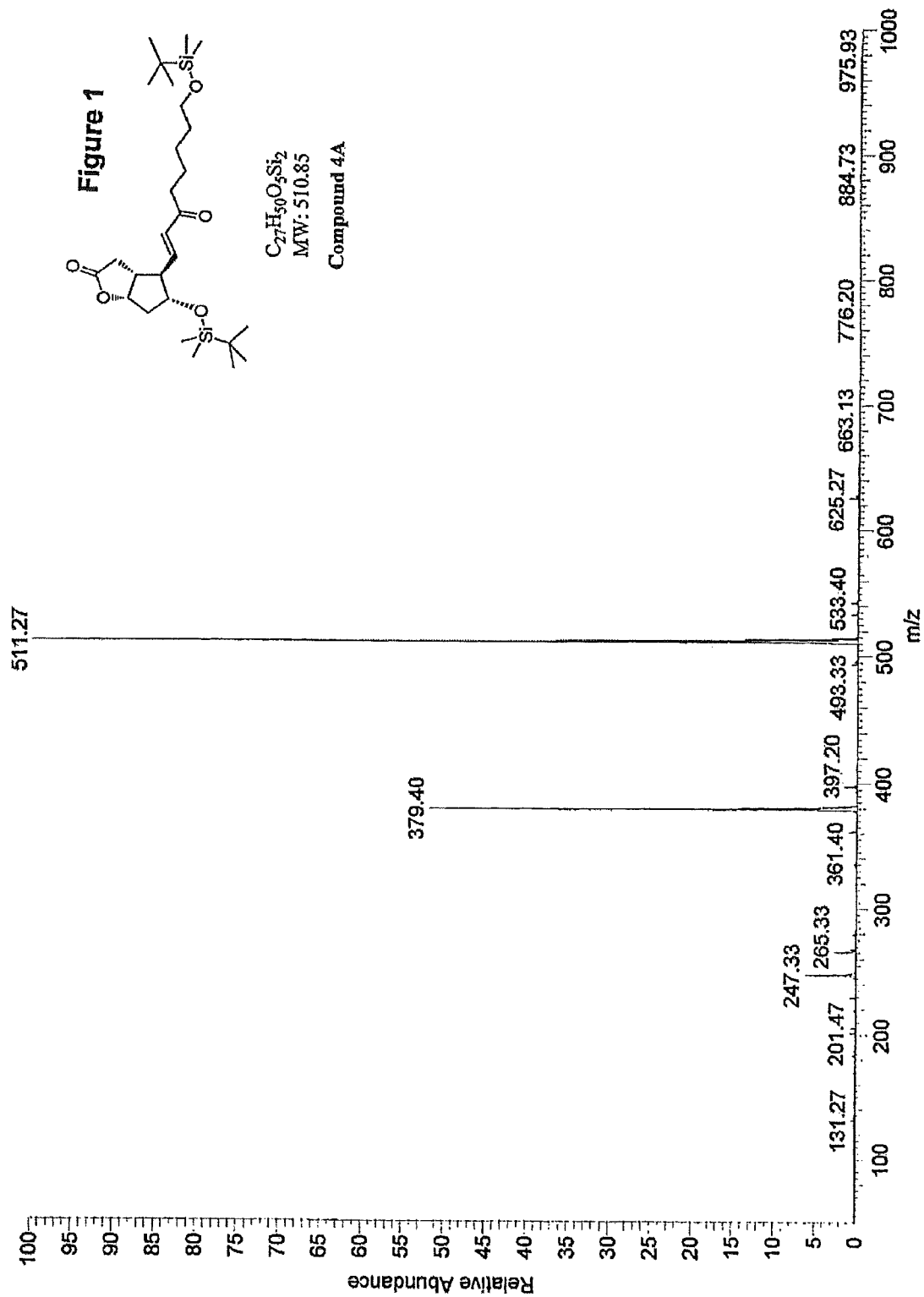
Figure 2:
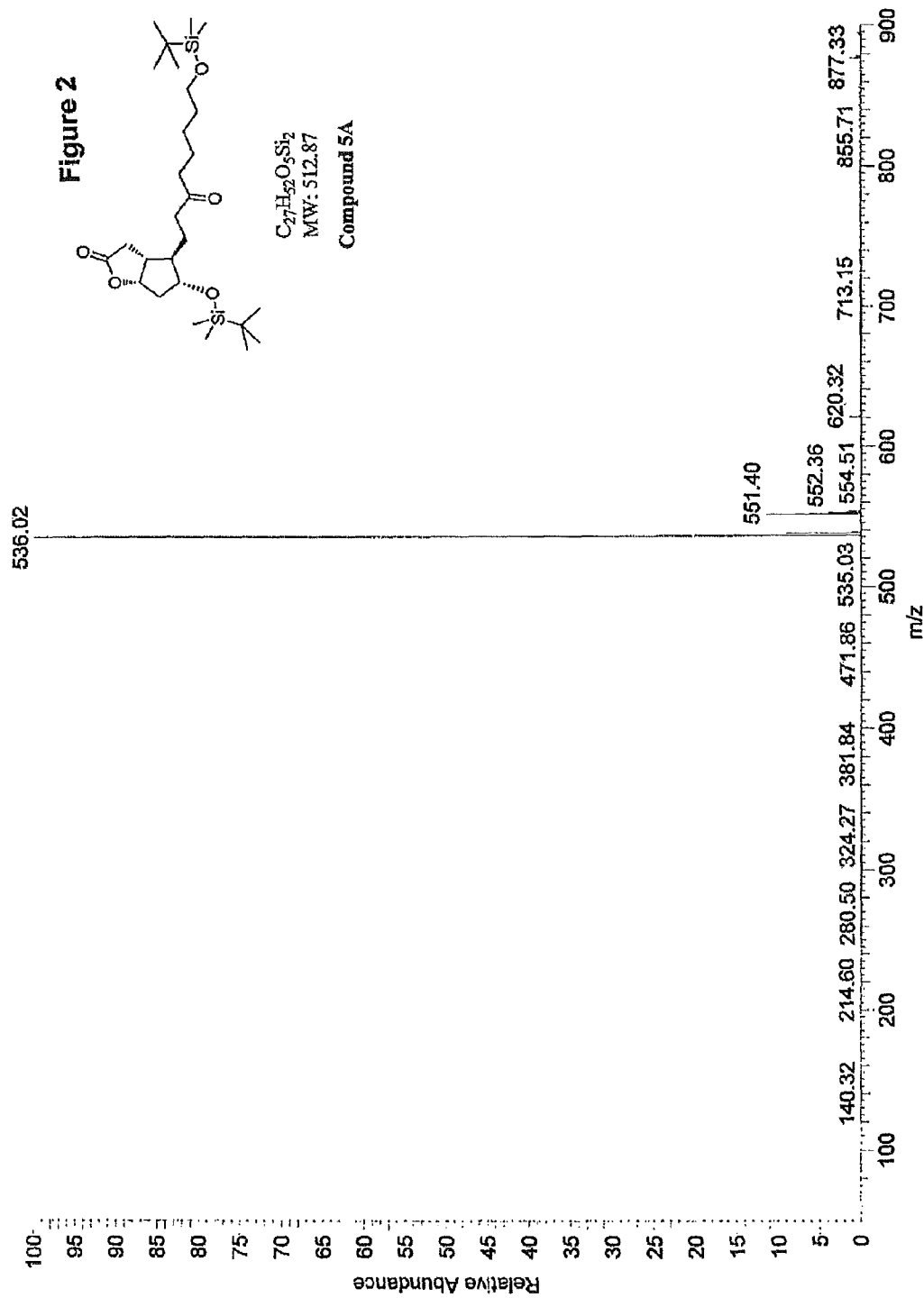
Figure 3:
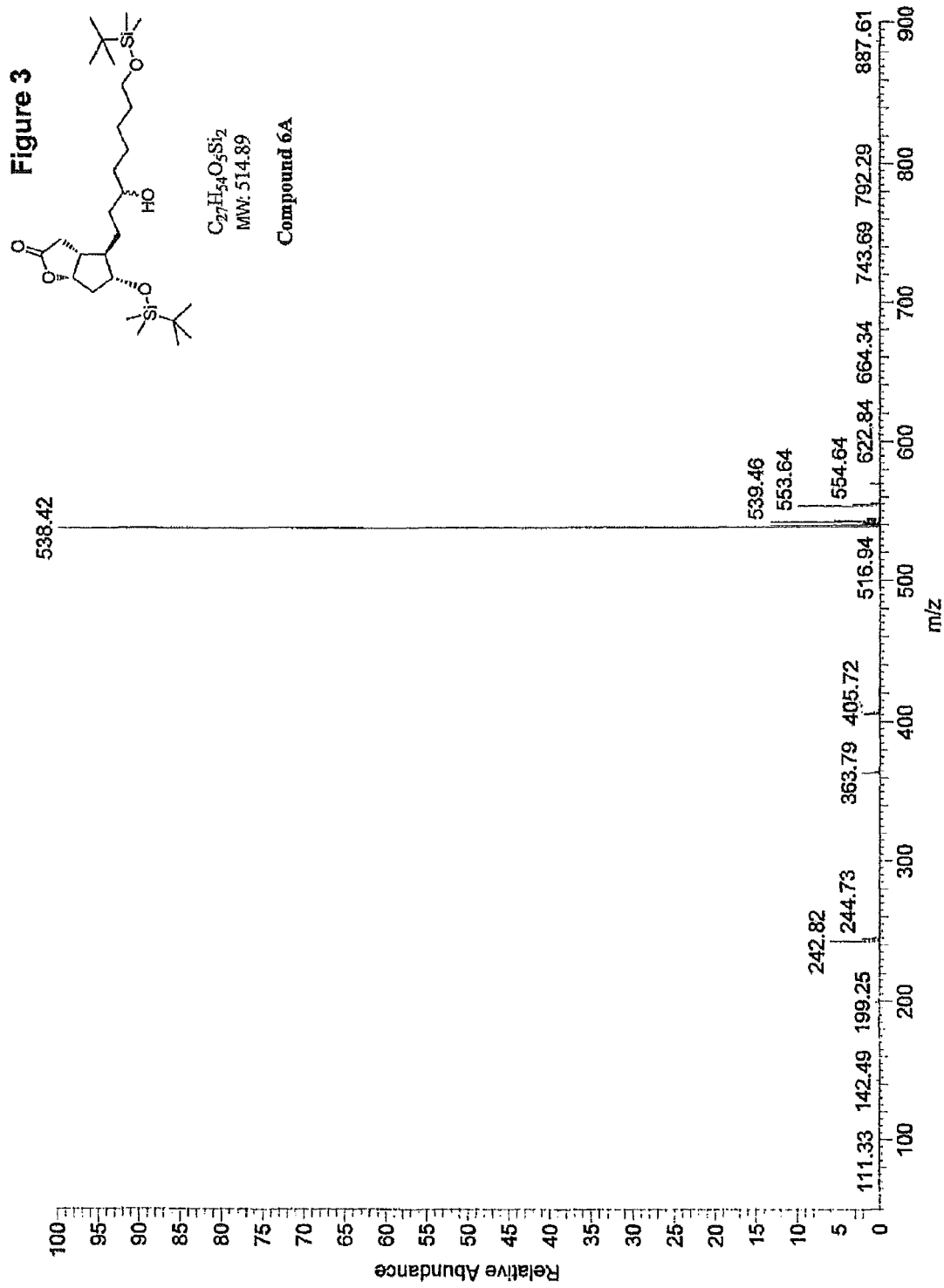
Figure 4:
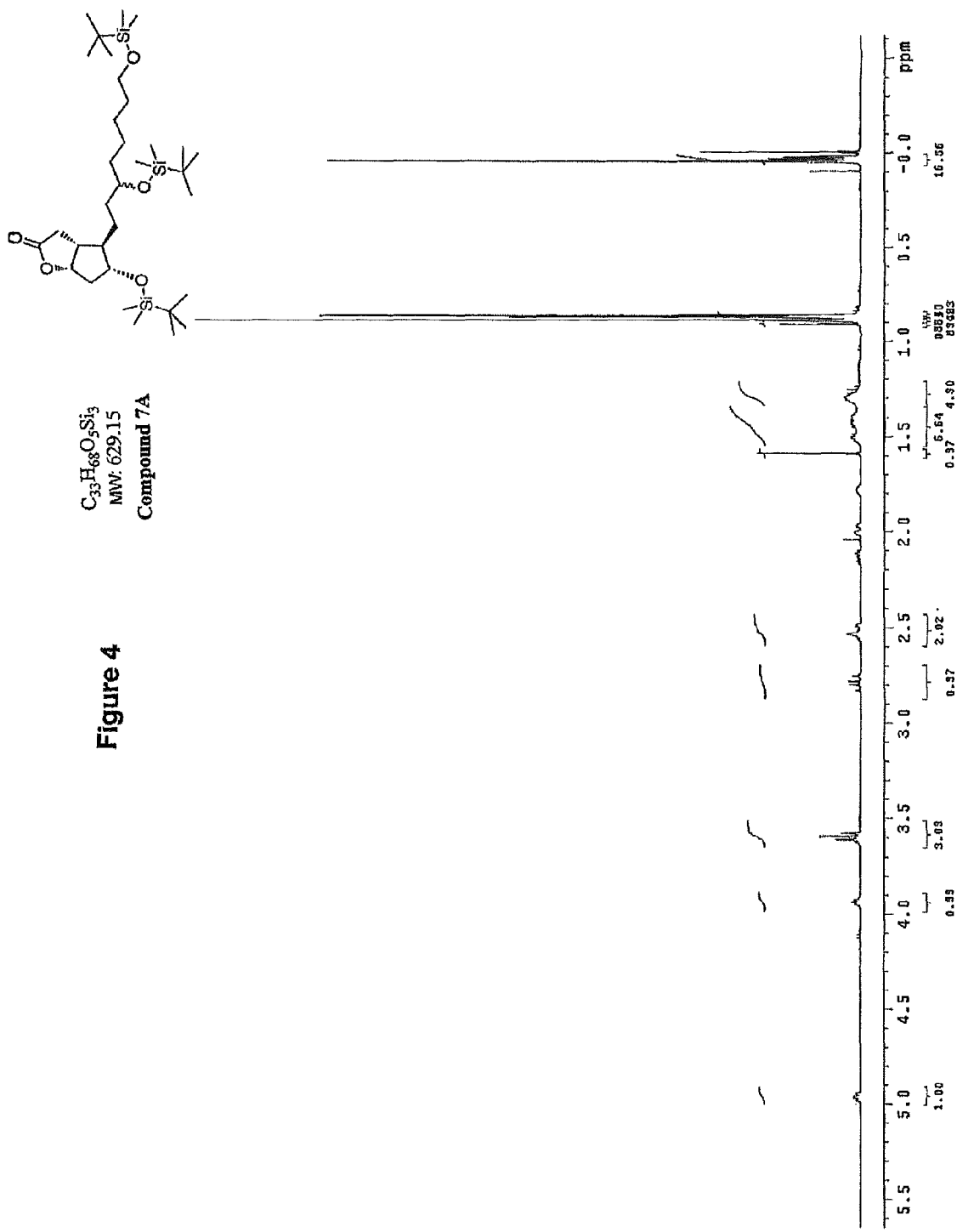
Figure 5A:
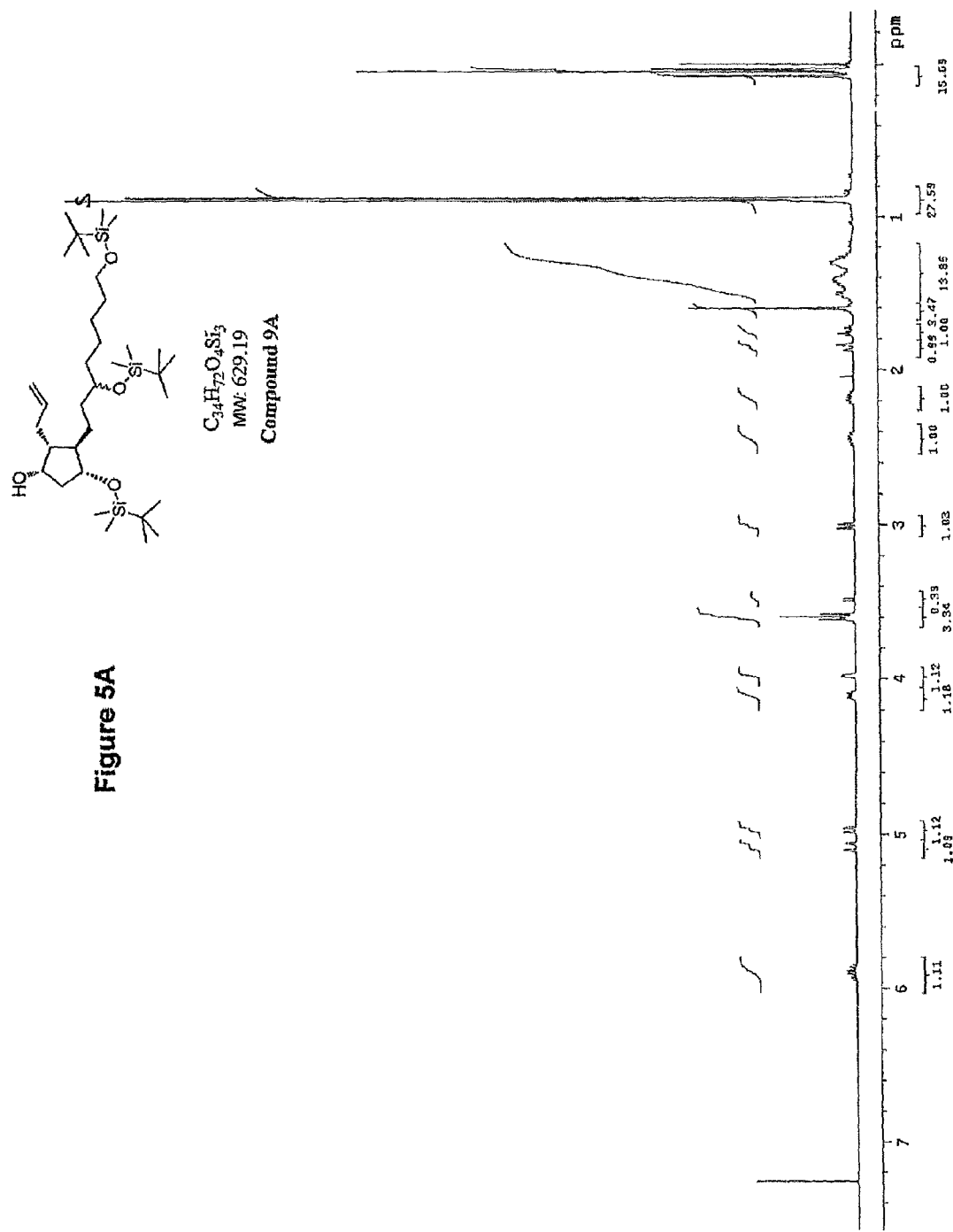
Figure 5B:
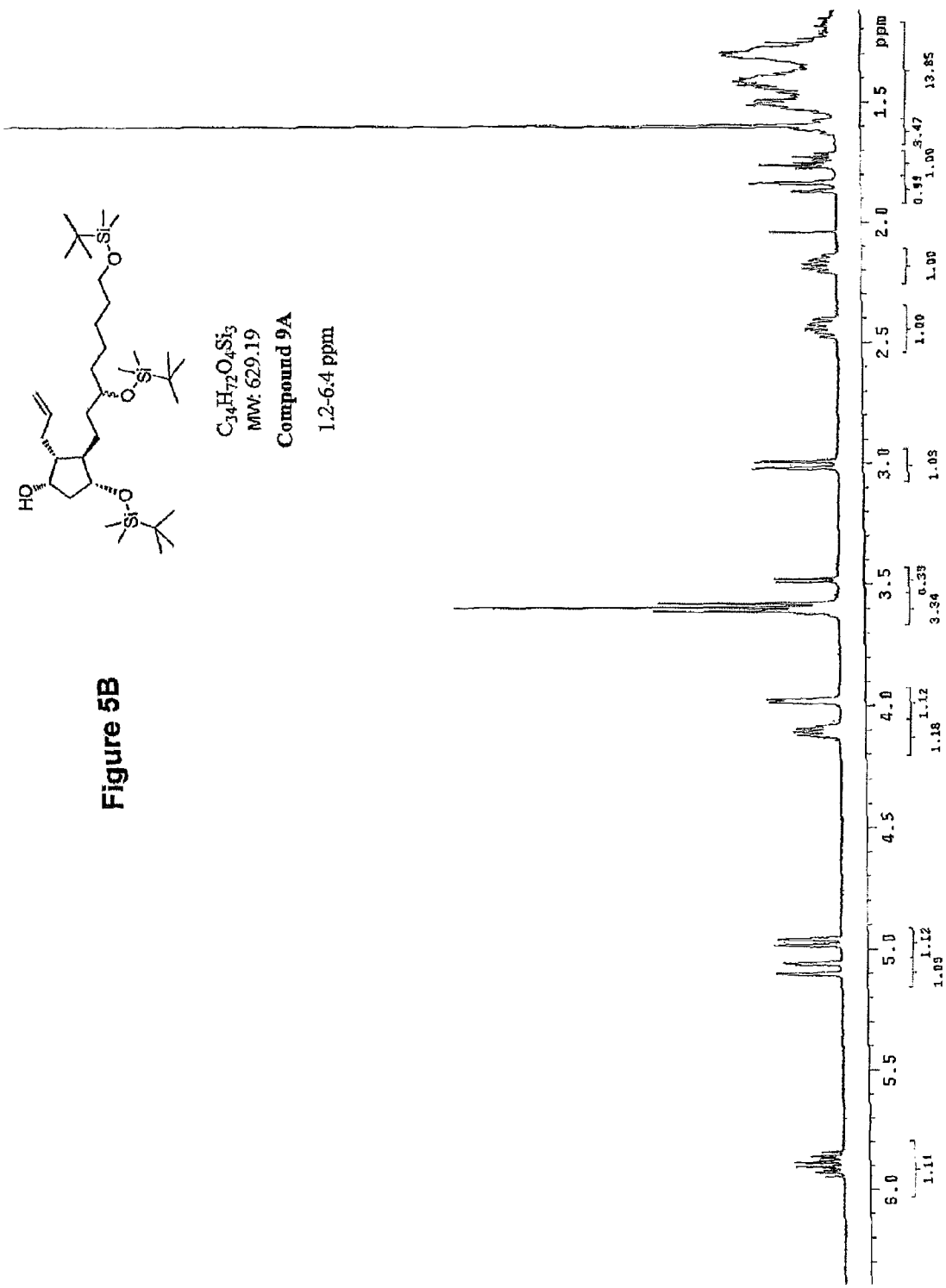
Figure 5C:
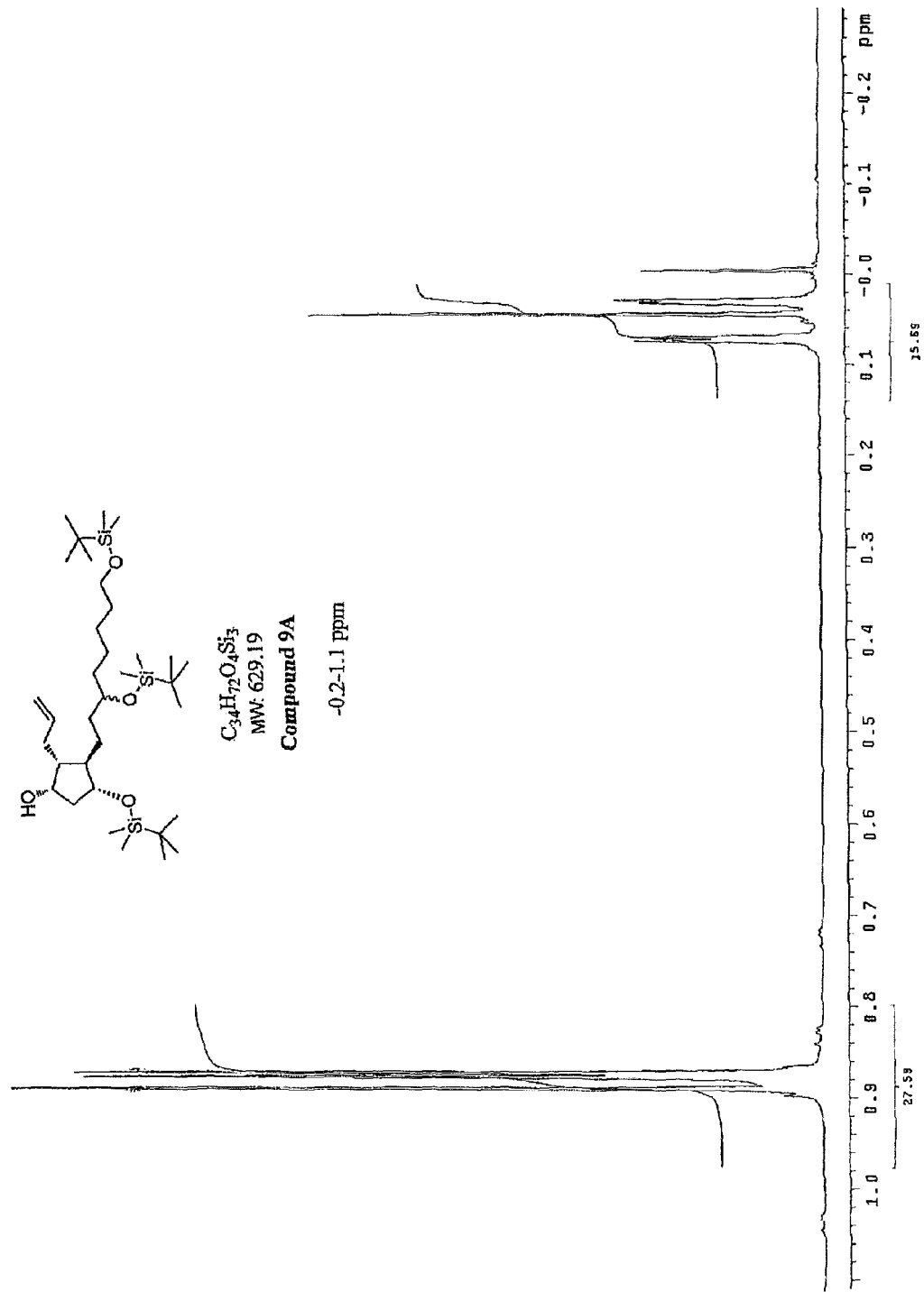
Figure 6:
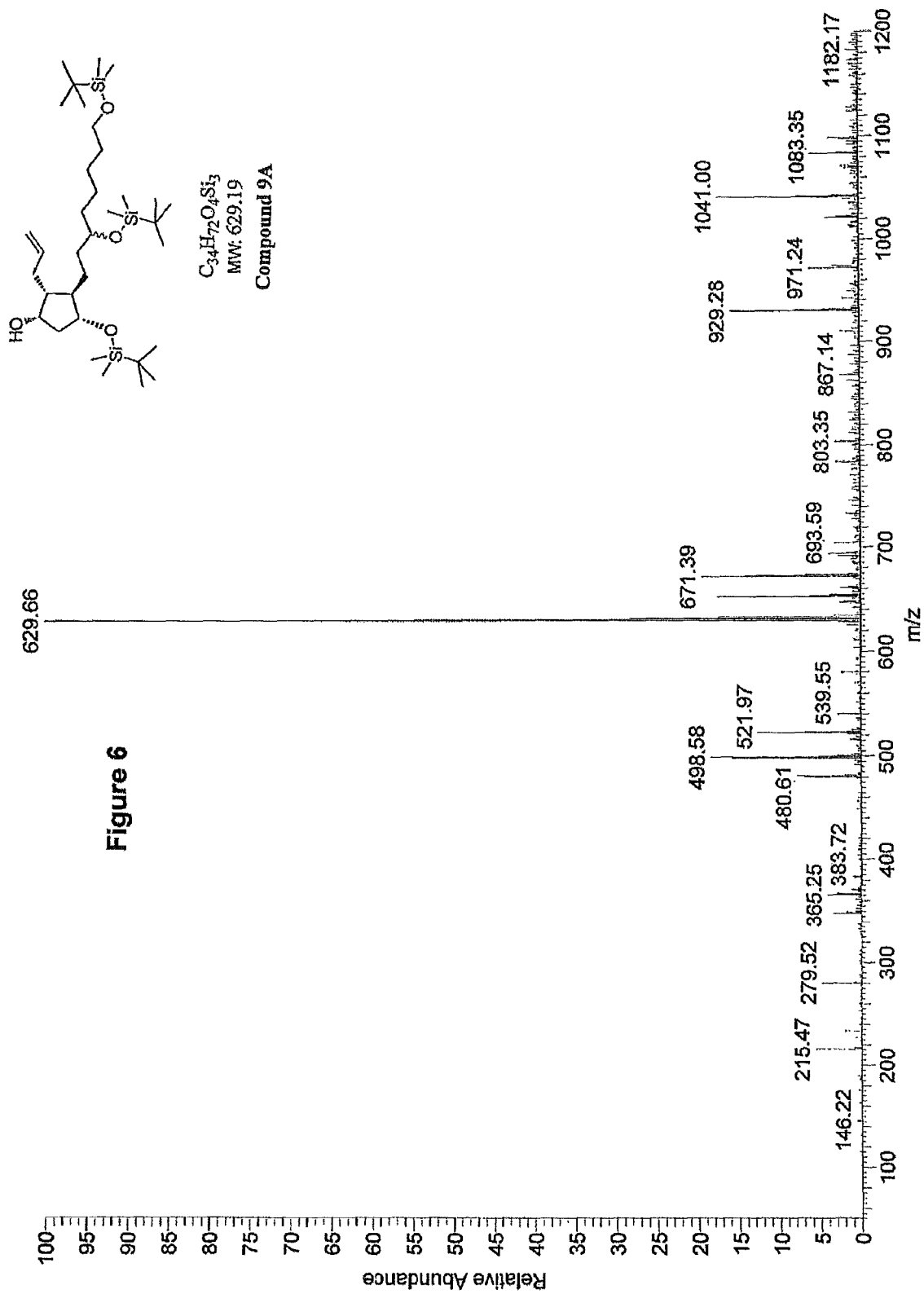
Figure 7:
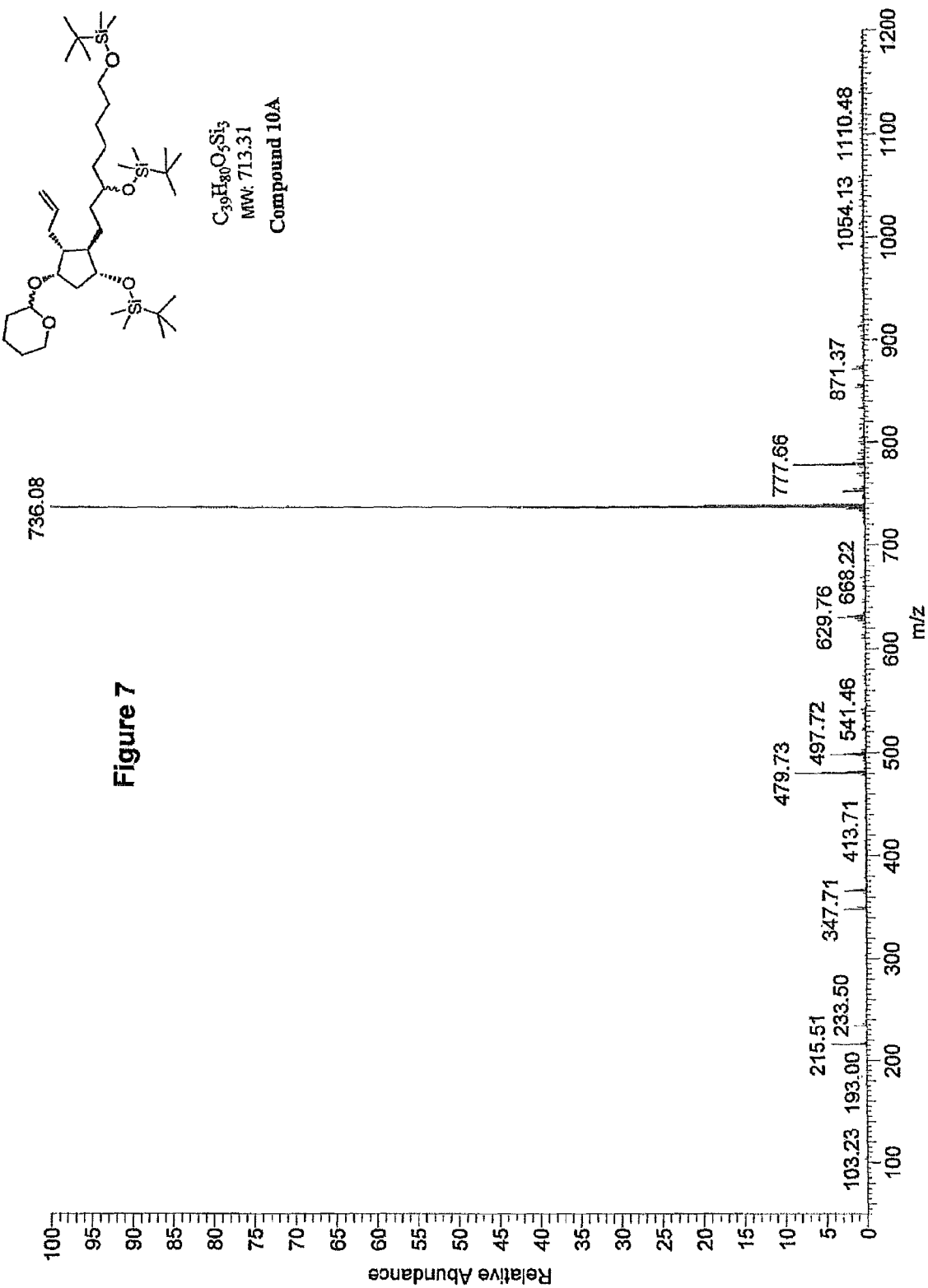
Figure 8A:
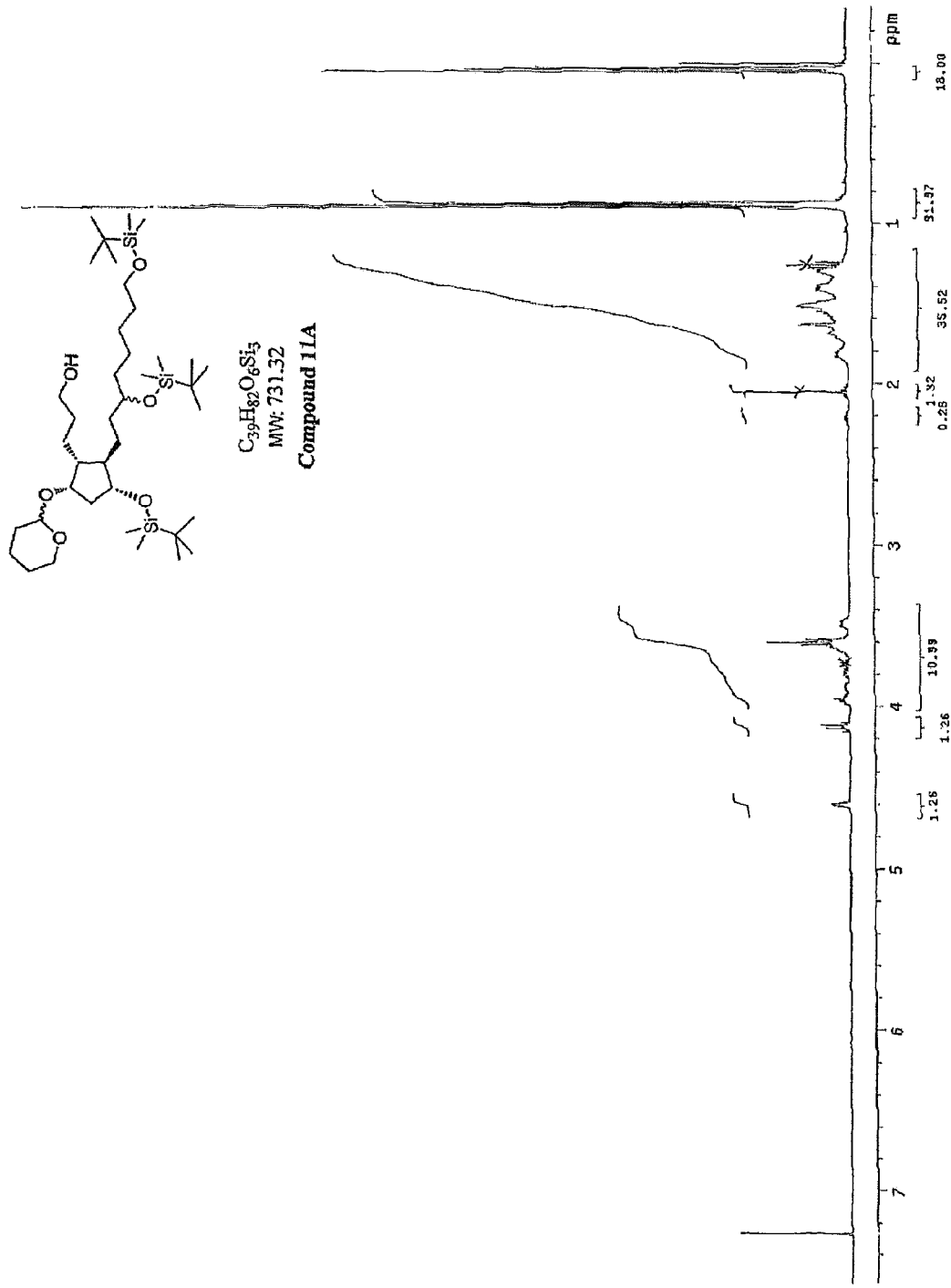
Figure 8C:
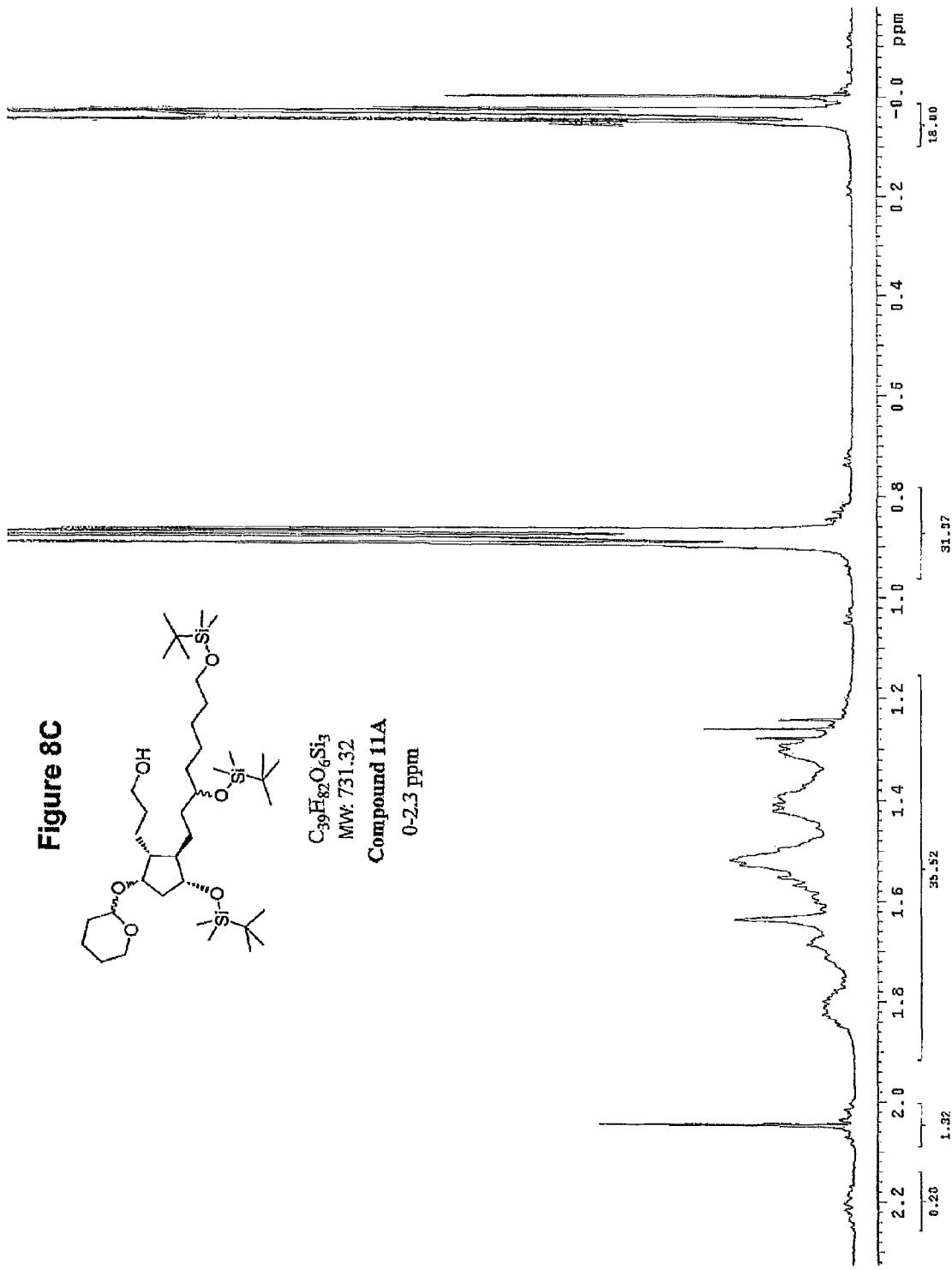
Figure 9A:
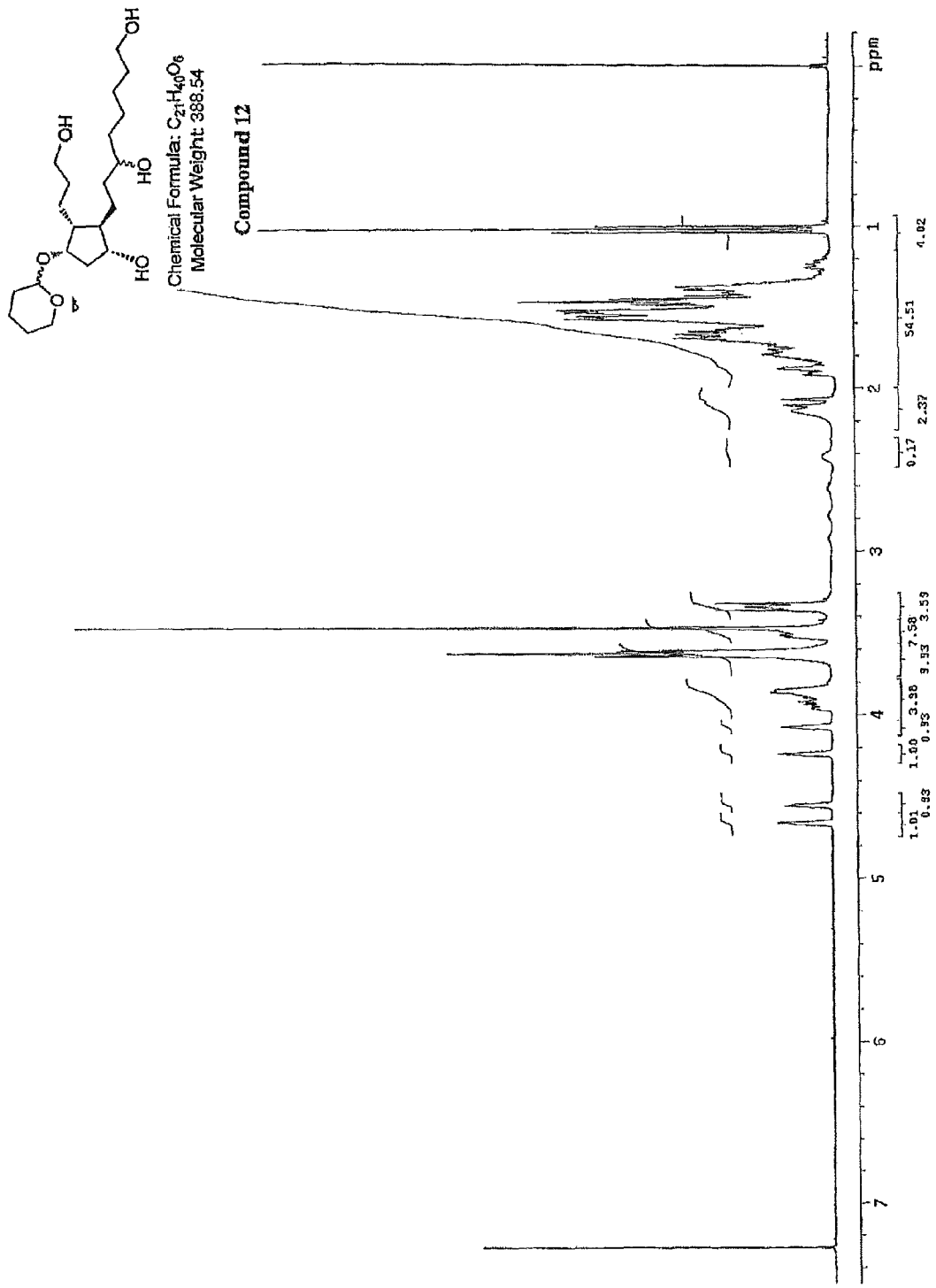
Figure 9C:
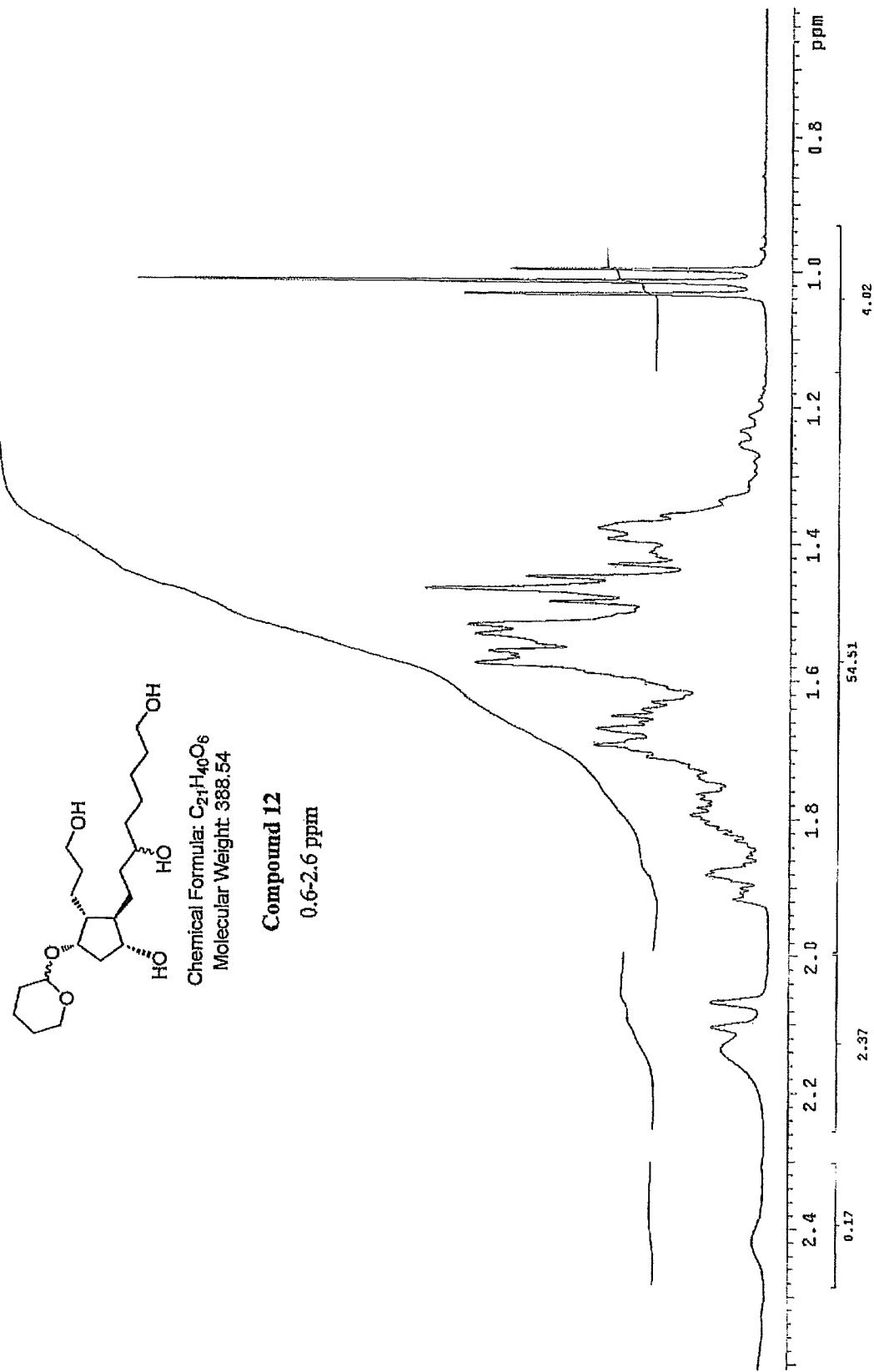
Figure 10A:
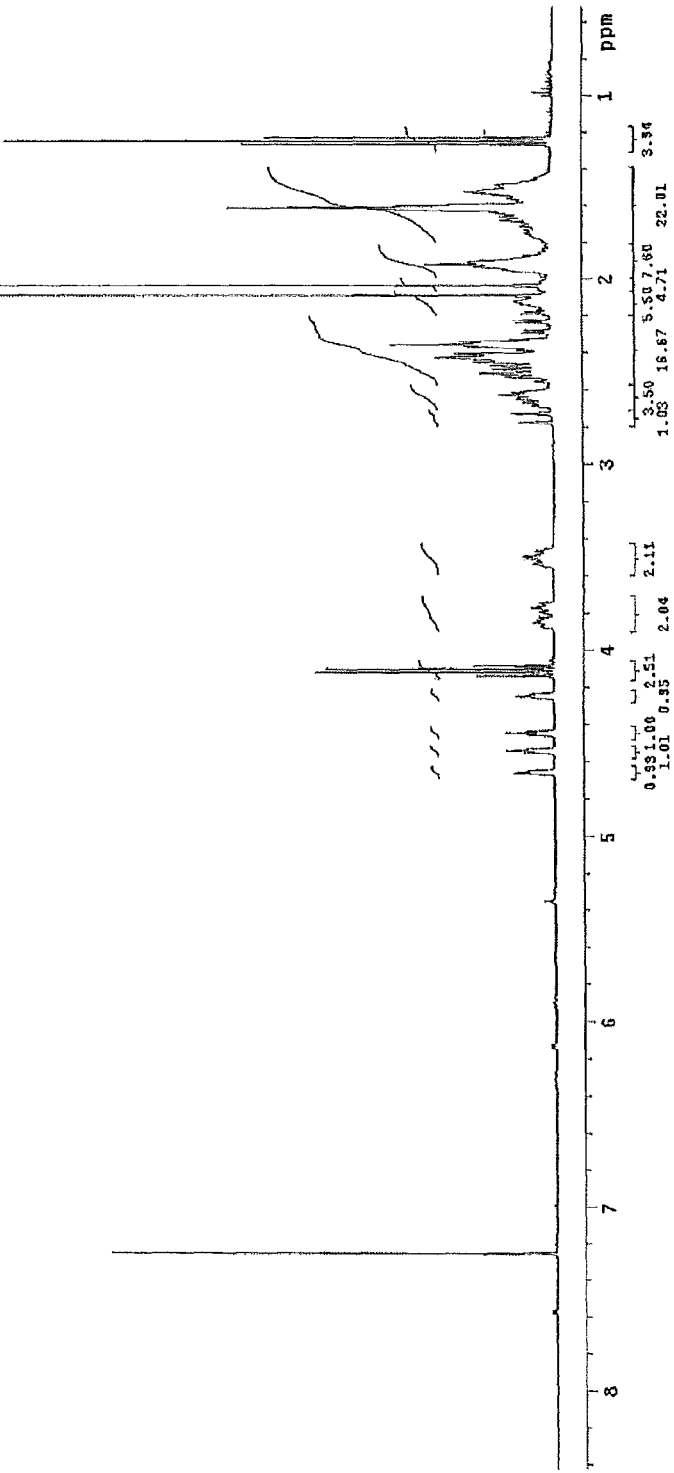
Figure 10B:
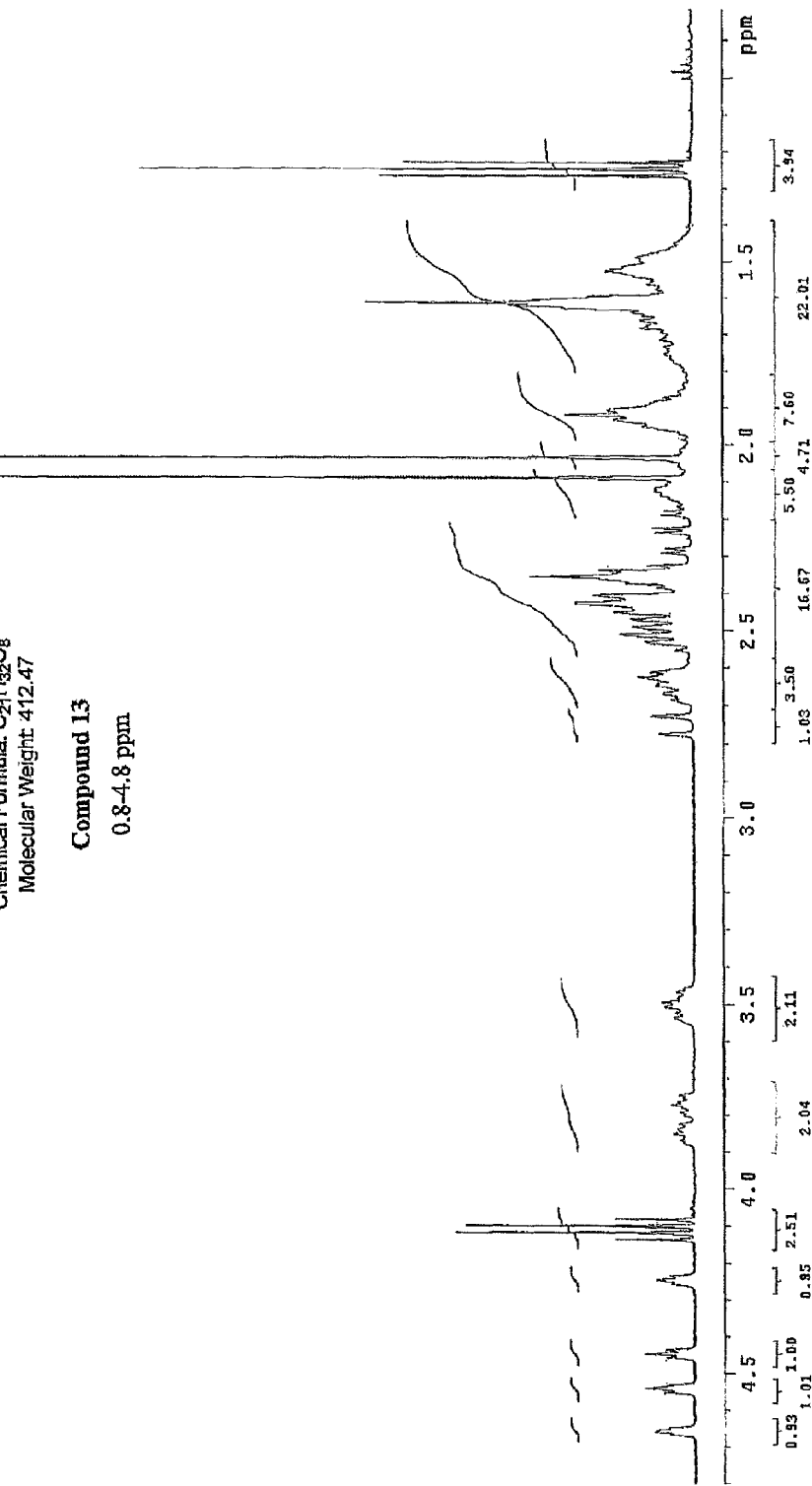
Figure 11:
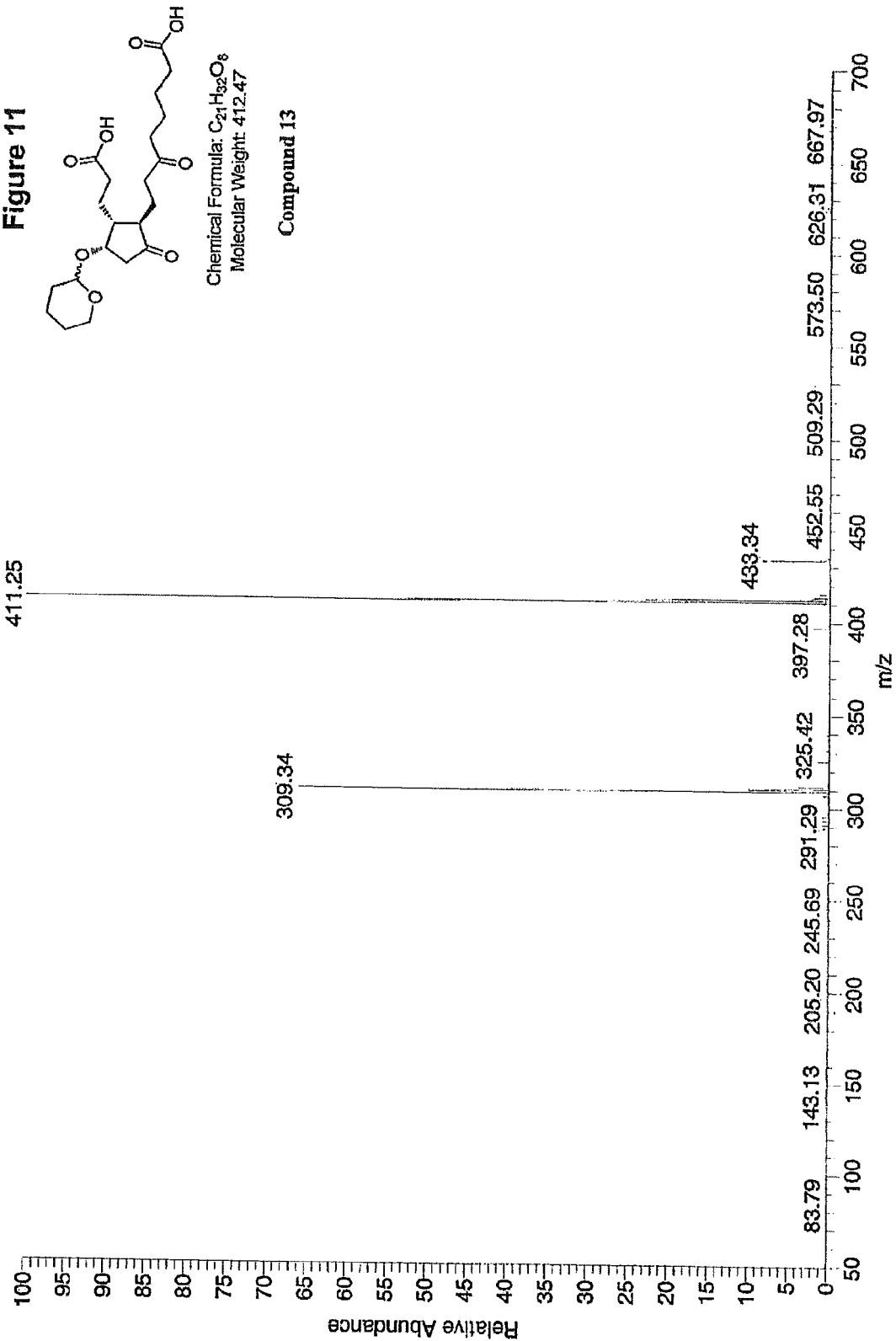

For purposes of the following detailed description, it is to be understood that the invention may assume various alternative variations and step sequences, except where expressly specified to the contrary. Moreover, other than in any operating examples, or where otherwise indicated, all numbers expressing, for example, quantities of ingredients used in the specification and claims are to be understood as being modified in all instances by the term "about". Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard variation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of equal to or less than 10.

In this application, the use of the singular includes the plural and plural encompasses singular, unless specifically stated otherwise. In addition, in this application, the use of "or" means "and/or" unless specifically stated otherwise, even though "and/or" may be explicitly used in certain instances.

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and biology described herein are those well known and commonly used in the art.

The term "protecting group" is a moiety that chemically modifies an organic functional group such that certain reaction conditions that would ordinarily cause chemical transformation of the functional group while unprotected are blocked from occurring on the protected functional group, and allowing desired chemical transformations to be carried out selectively on other functional groups that may be transformed by the reaction conditions. Protecting groups and protective group chemistry commonly used in the art is described in Greene, T. W. and Wuts, P. G. M., 1991, *Protective Groups in Organic Synthesis*, Second Edition, John Wiley & Sons, Inc., New York.

The term "THF" refers to tetrahydrofuran.

The term "DMF" refers to N,N-dimethylformamide.

The term "DHP" refers to 3,4-dihydropyran (added to hydroxyl group to form THP-O group, or THP-protected hydroxyl group).

The term "PPTS" refers to pyridinium p-toluenesulfonate.

The term "Et" as in "Et$_3$N", refers to ethyl.

The term "DIBAL" refers to diisobutylaluminum.

The term "BuOK" refers to potassium butoxide, while the term "$^t$BuOK" refers to potassium tert-butoxide.

The term "THP" refers to tetrahydropyran.

The term "BBN" refers to borabicyclo[3.3.1]nonane, while the term "9-BBN" refers to 9-borabicyclo[3.3.1]nonane.

The term "Jones Oxidation" refers to an organic reaction for the oxidation of primary and secondary alcohols to carboxylic acids and ketones, respectively. A "Jones Reagent" is a solution of chromium trioxide in dilute sulfuric acid and acetone. A mixture of potassium dichromate and dilute sulfuric acid can also be used as the "Jones Reagant".

The term "Ac" as in "AcOH" refers to acetyl, or $CH_3$—C=O, also written as $CH_3CO$, with an open valence on the carbonyl carbon atom that bonds to —OH to form acetic acid. Accordingly, the term "AcOH" refers to acetic acid, or $CH_3$—$CO_2H$.

The term "TBDMS" refers to tert-butyldimethylsilyl.

The term "TBDPS" refers to tert-butyldiphenylsilyl.

The term "TIPS" refers to triisopropylsilyl.

The term "TBAF" refers to tetrabutylammonium fluoride.

The term "EA" refers to ethyl acetate.

The term "$R_f$" refers to retention factor. For thin layer chromatography (TLC), $R_f$ is defined as the distance traveled by the compound divided by the distance traveled by the solvent or solvent system (mobile phase) on the silica (stationary phase) of the TLC plate.

The term "PG" refers to prostaglandin.

The term "TLC" refers to thin layer chromatography.

The term "Bz" refers to the benzoyl group, or Ph-C=O, also written as PhCO, with an open valence on the carbonyl carbon atom that bonds to —OH to form benzoic acid, for example.

The exemplary embodiments may be directed to a synthetic route for the preparation of tetranor-PGDM (Compound 14), comprising the reaction steps illustrated in Scheme I:

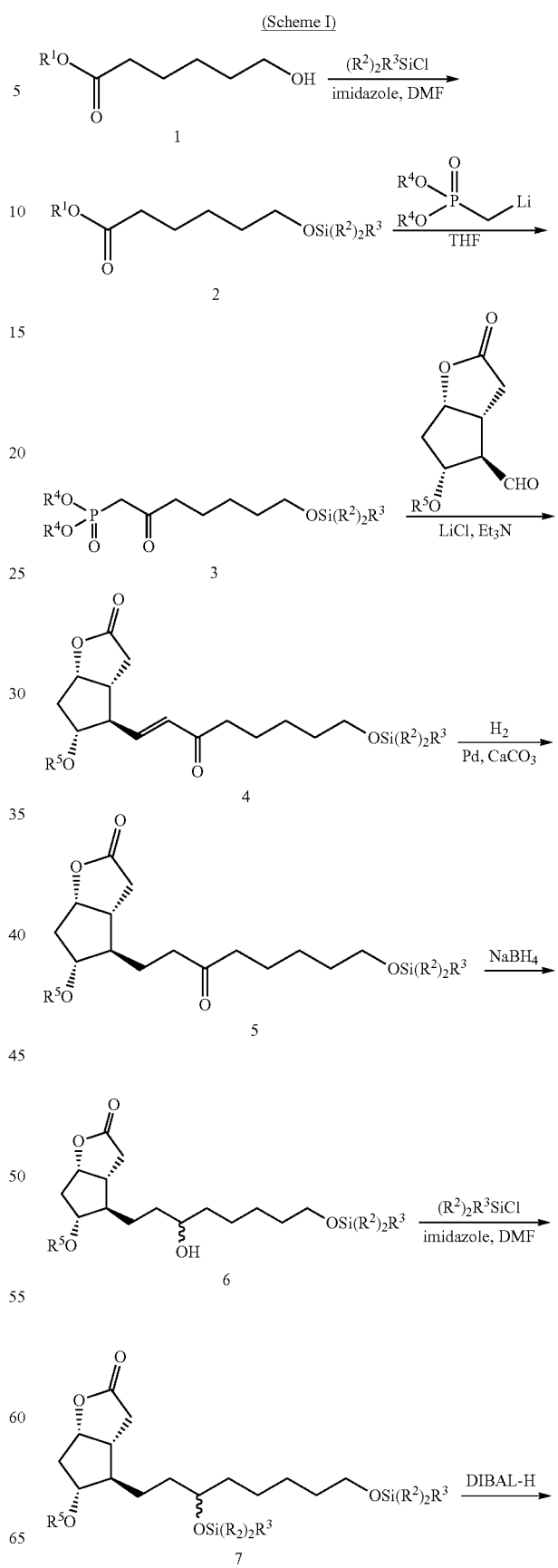

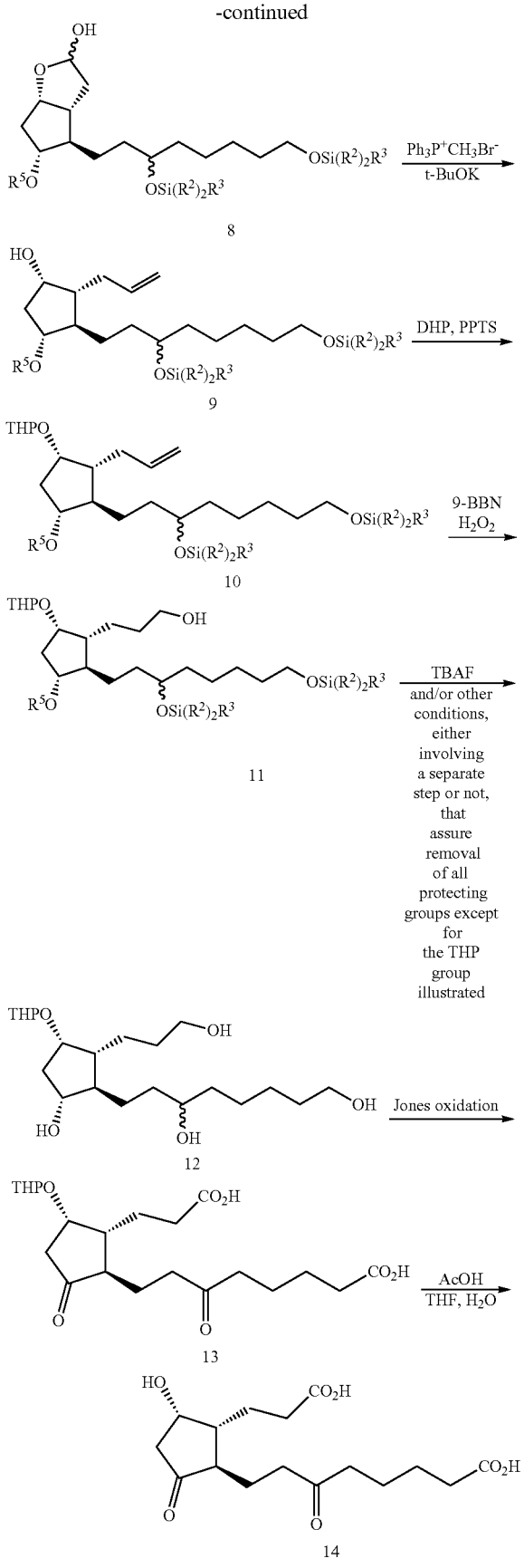

wherein $R^1$ is $C_{1-4}$ alkyl; each $R^2$ is independently $C_{1-5}$ alkyl or phenyl; each $R^3$ is independently a $C_{1-4}$ alkyl; $R^4$ is methyl or ethyl; and $R^5$ is a protecting group. See FIGS. 1 through 12 for spectral data confirming the synthesis of certain forms of Compounds 4A, 5A, 6A, 7A, 9A, 10A, 11A, 12, 13 and 14 by the methods of Scheme I.

In certain embodiments, the protecting group $R^5$ comprises tert-butyldimethylsilyl (TBDMS), a protecting group that is stable to all reaction conditions between its introduction to the reaction sequence illustrated in Scheme I and its required removal by appropriate deprotection conditions.

Other exemplary embodiments may be directed to a synthetic method for the preparation of Compound 15, tetranor-PGJM, from tetranor-PGDM comprising an acid-catalyzed dehydration as illustrated in Scheme II:

(Scheme II)

Figure 14A:
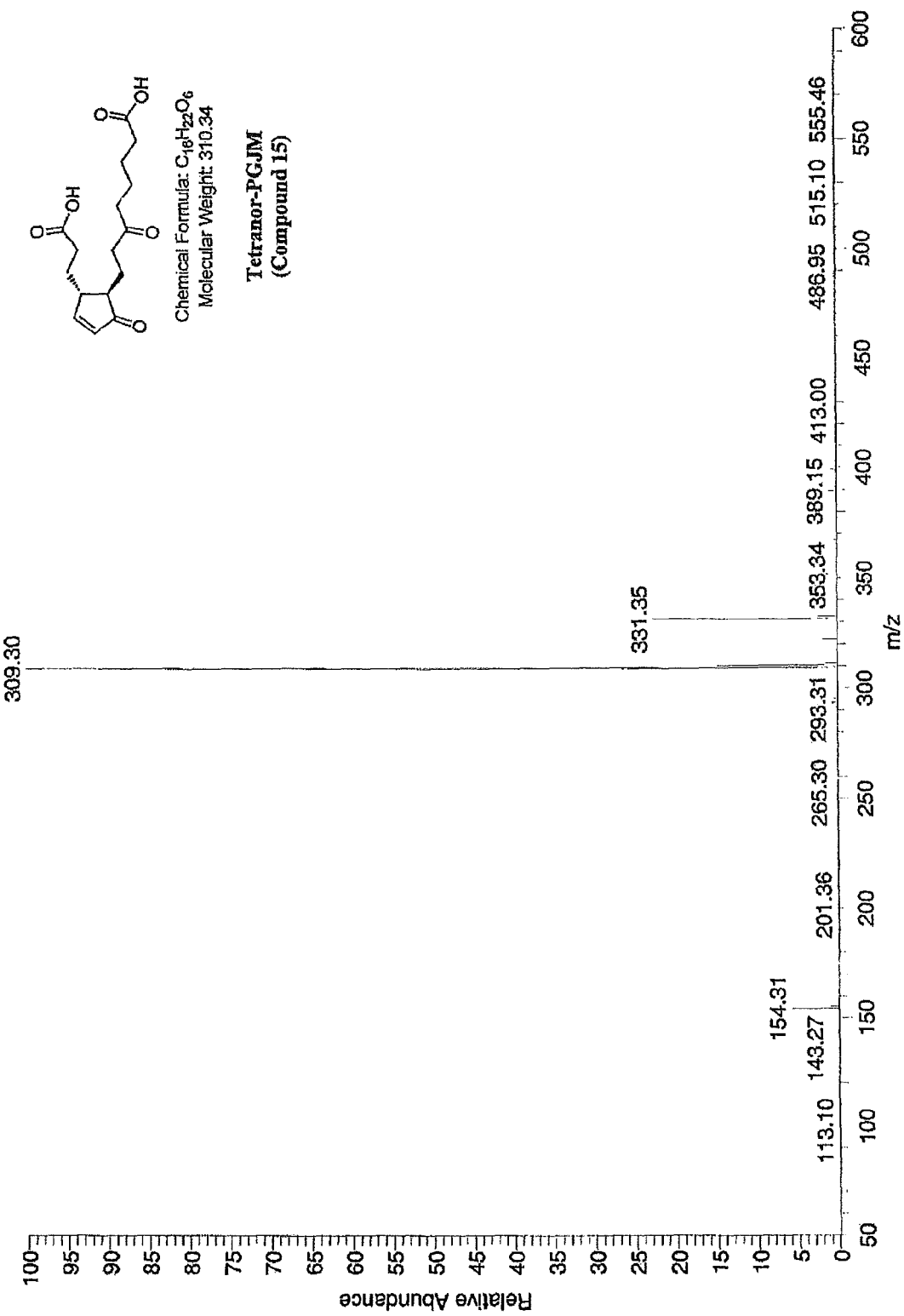
Figure 14B:
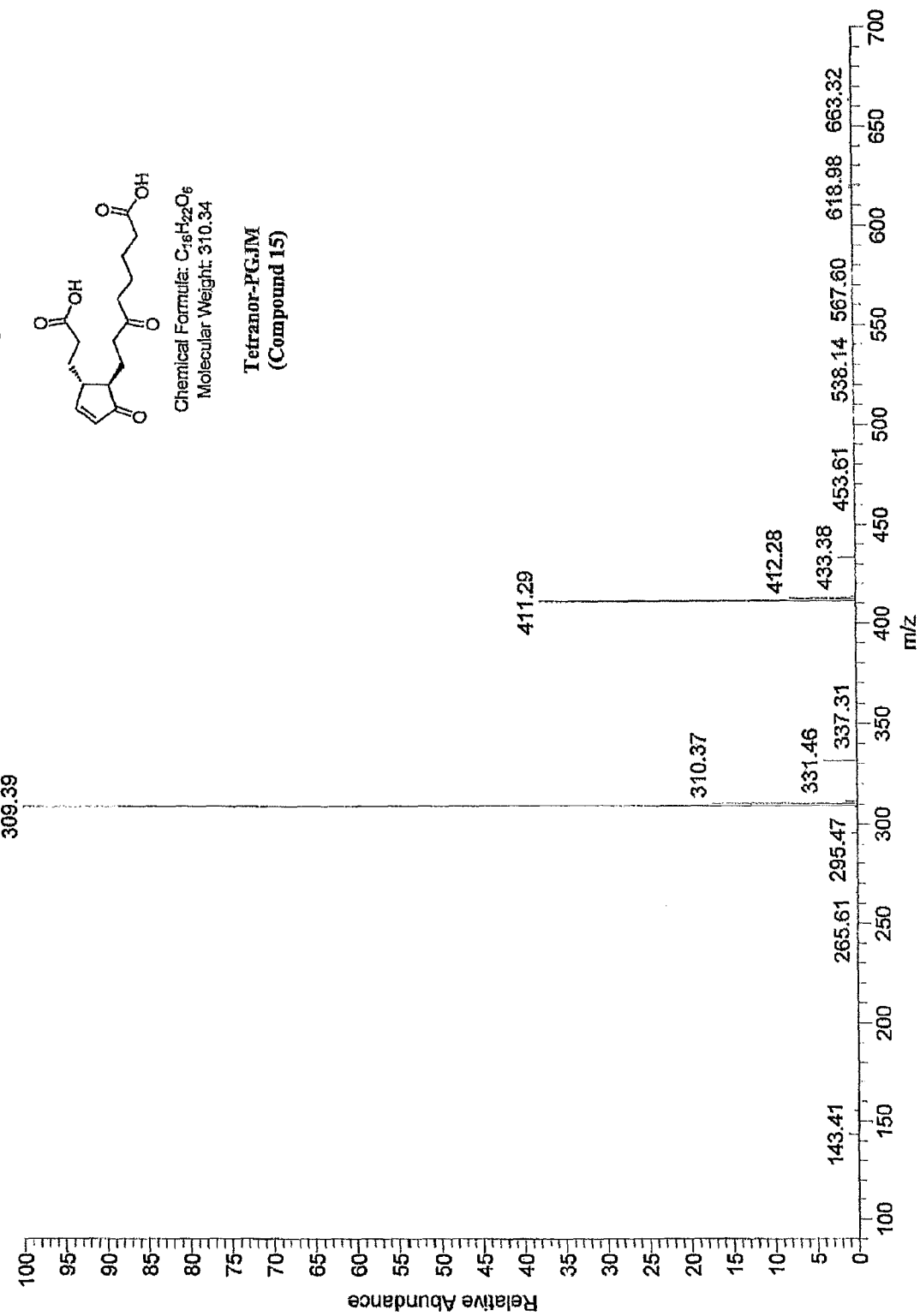
Figure 15:
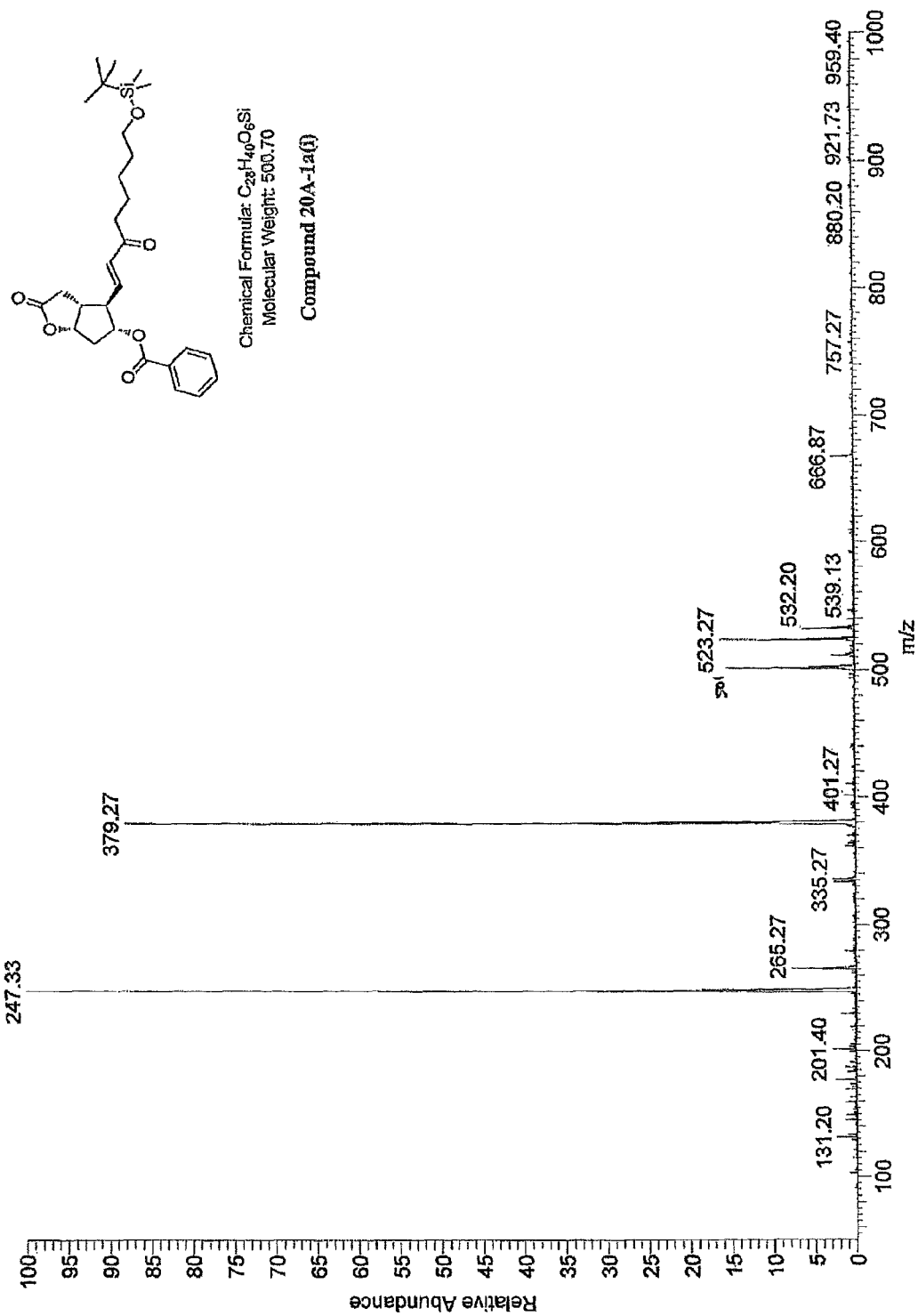
Figure 16:
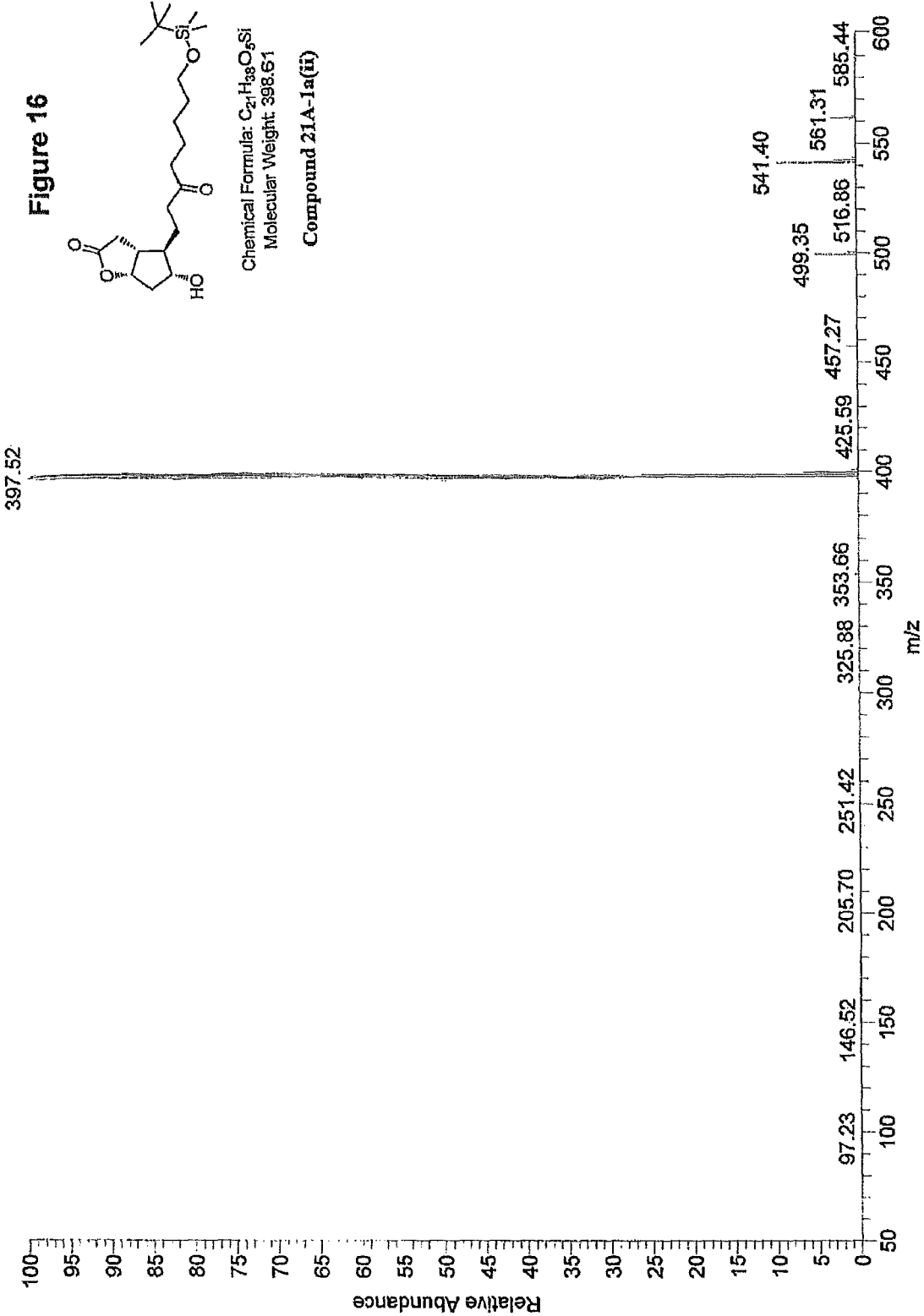
Figure 17:
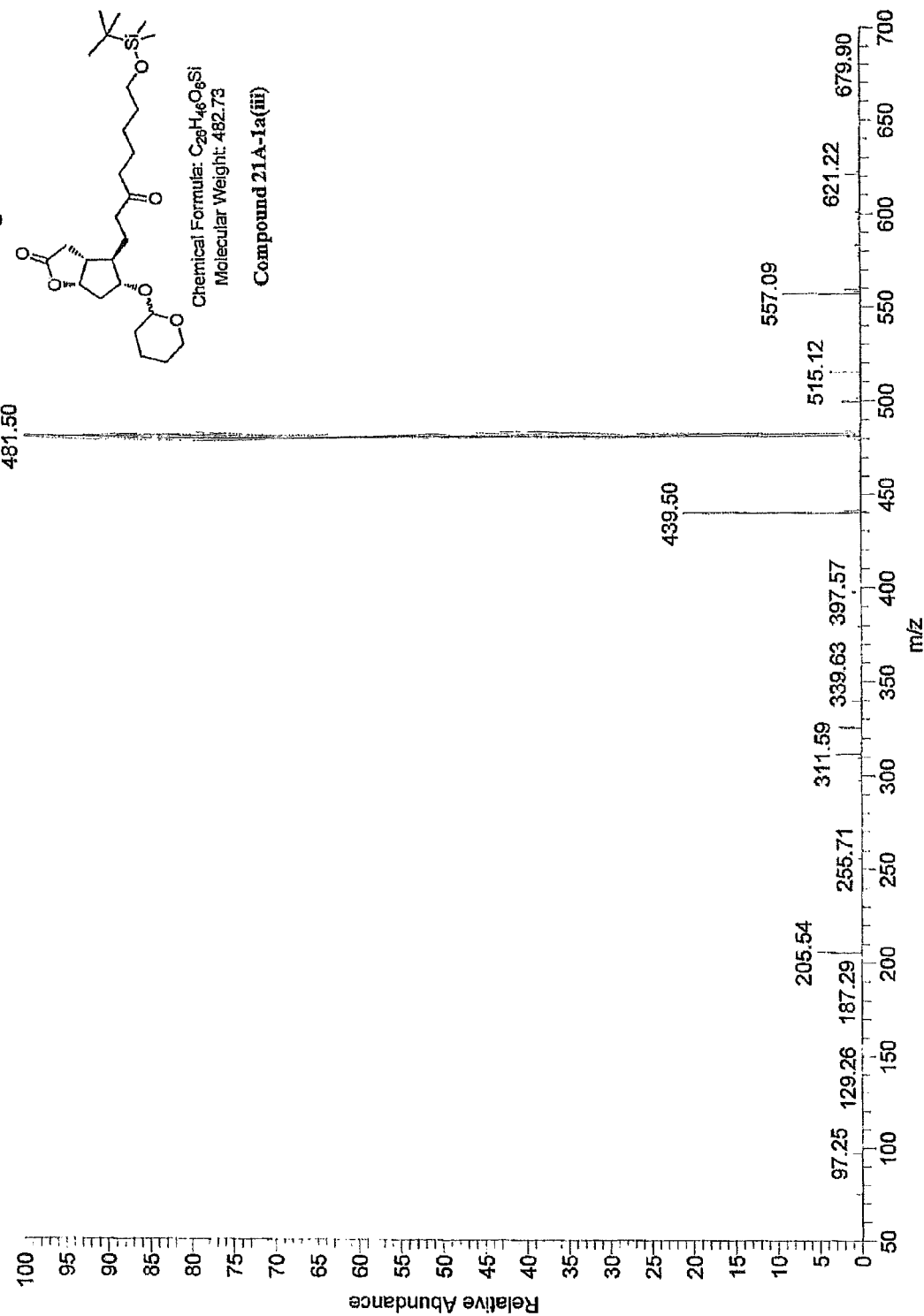
Figure 18:
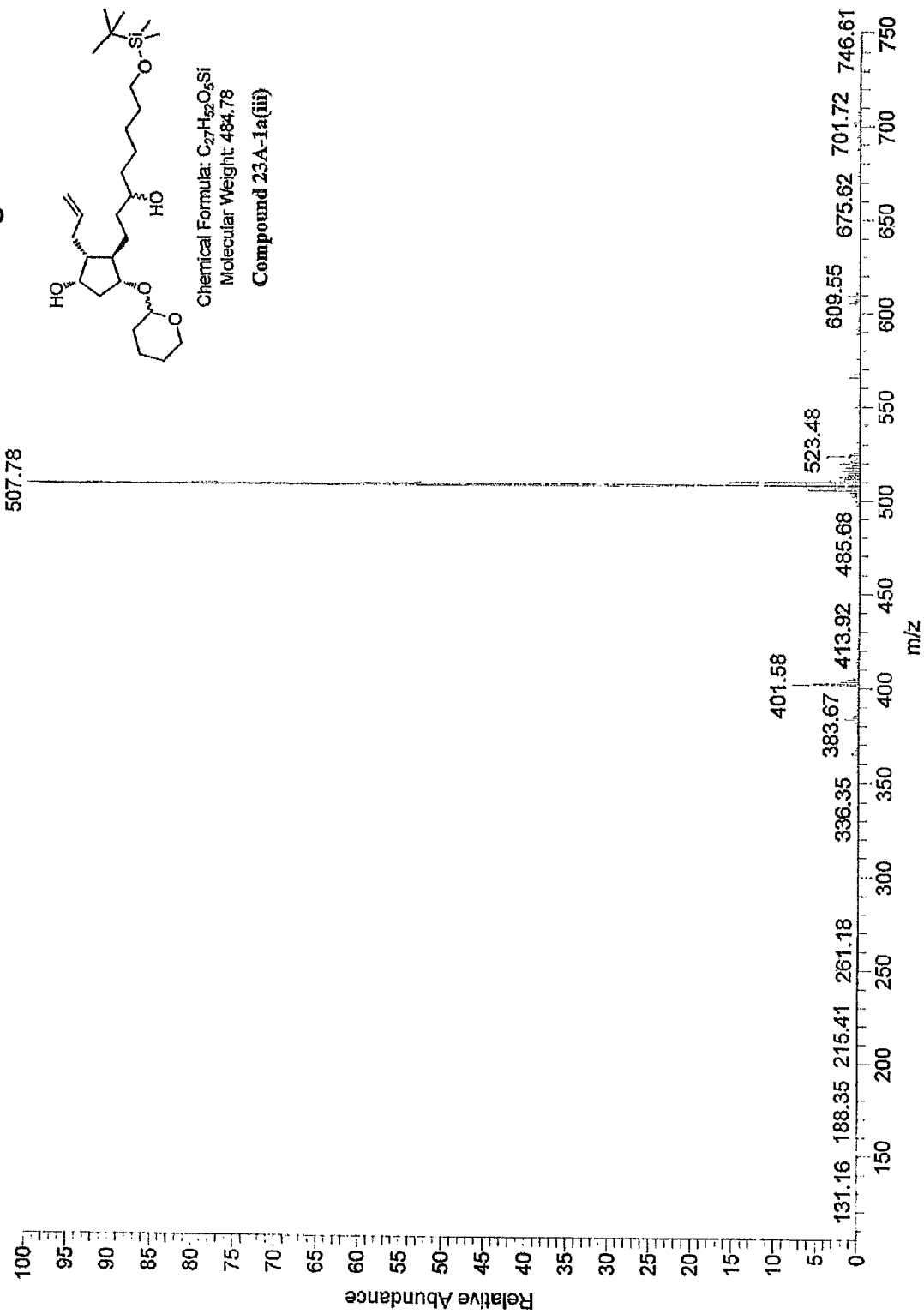
Figure 19:
Figure 20:
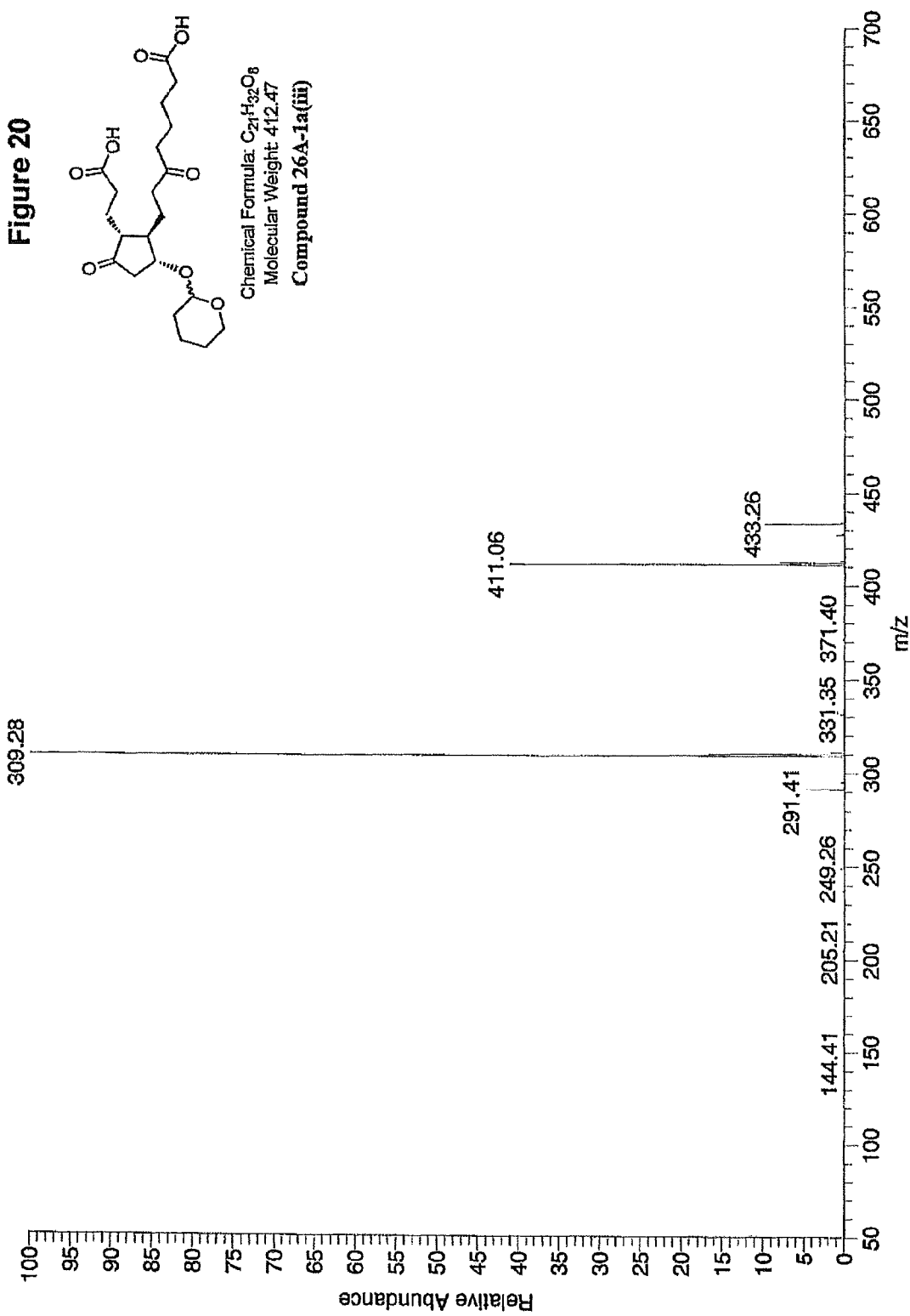
Figure 21D:
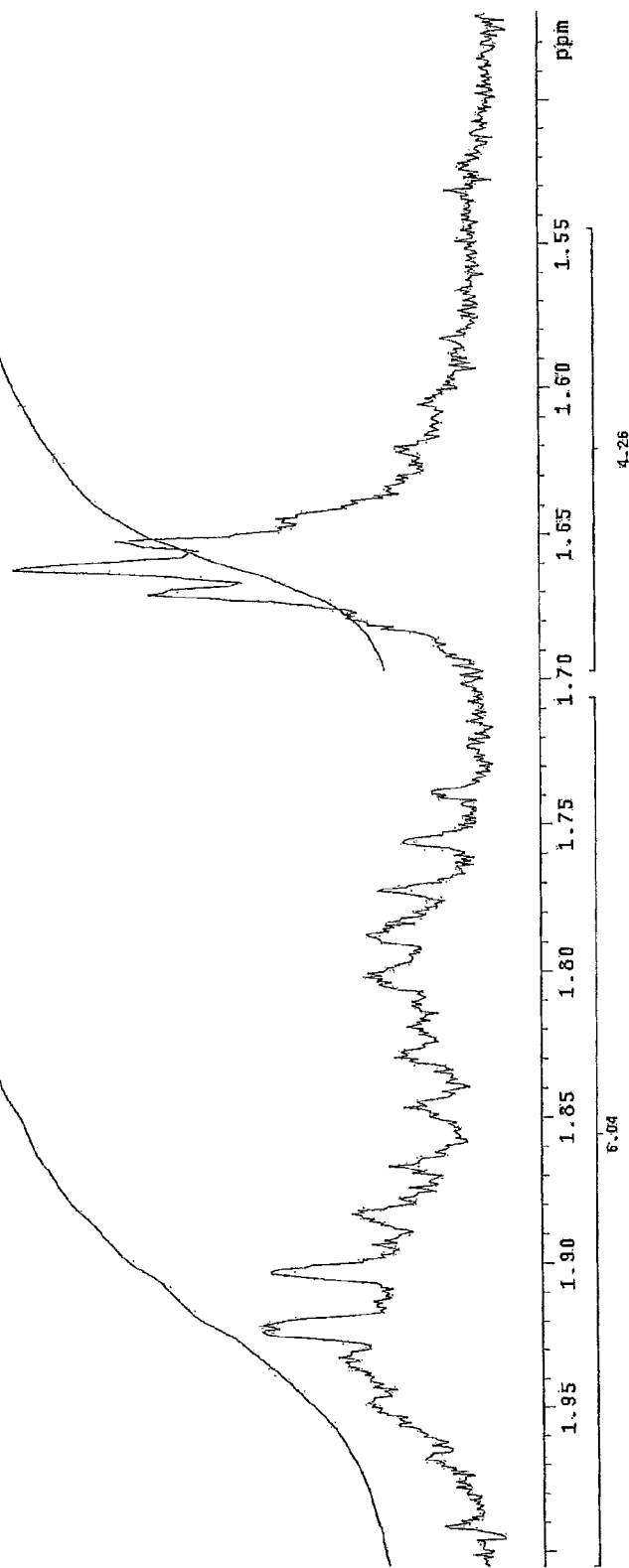
Figure 22:
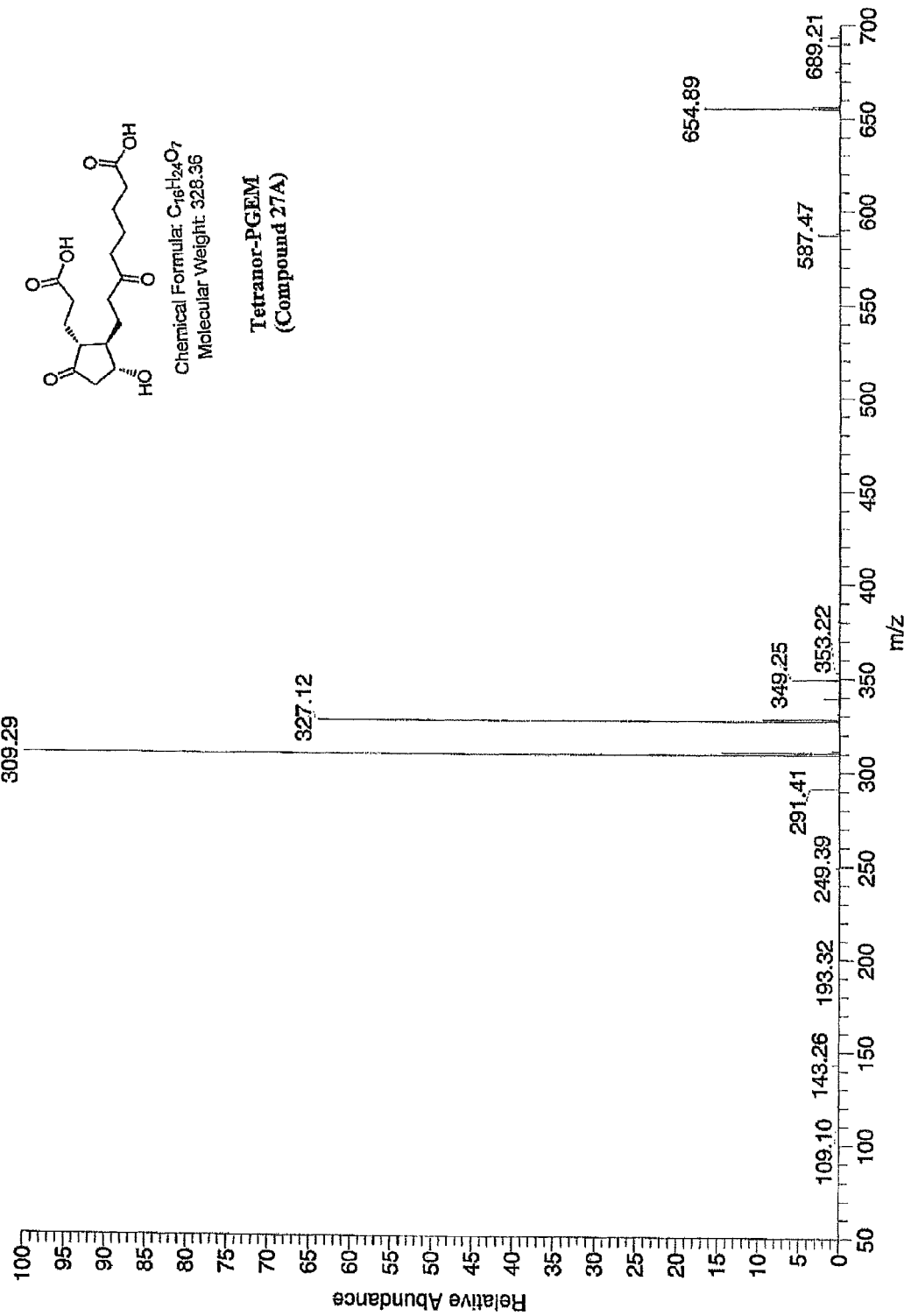

In certain embodiments, the acid comprises any organic or inorganic acid. In certain embodiments, the acid comprises acetic acid or trifluoroacetic acid. See FIGS. 13 and 14A-B for spectral data confirming the synthesis of Compound 15 by the methods of Scheme II.

Other exemplary embodiments may be directed to a synthetic route for the preparation of Compound 27A, tetranor-PGEM, and Compound 27B, a deuterated ($D_6$) analog of tetranor-PGEM, comprising the reaction steps as illustrated in Scheme III:

(Scheme III)

16A, $R^6$ = H
16B, $R^6$ = D

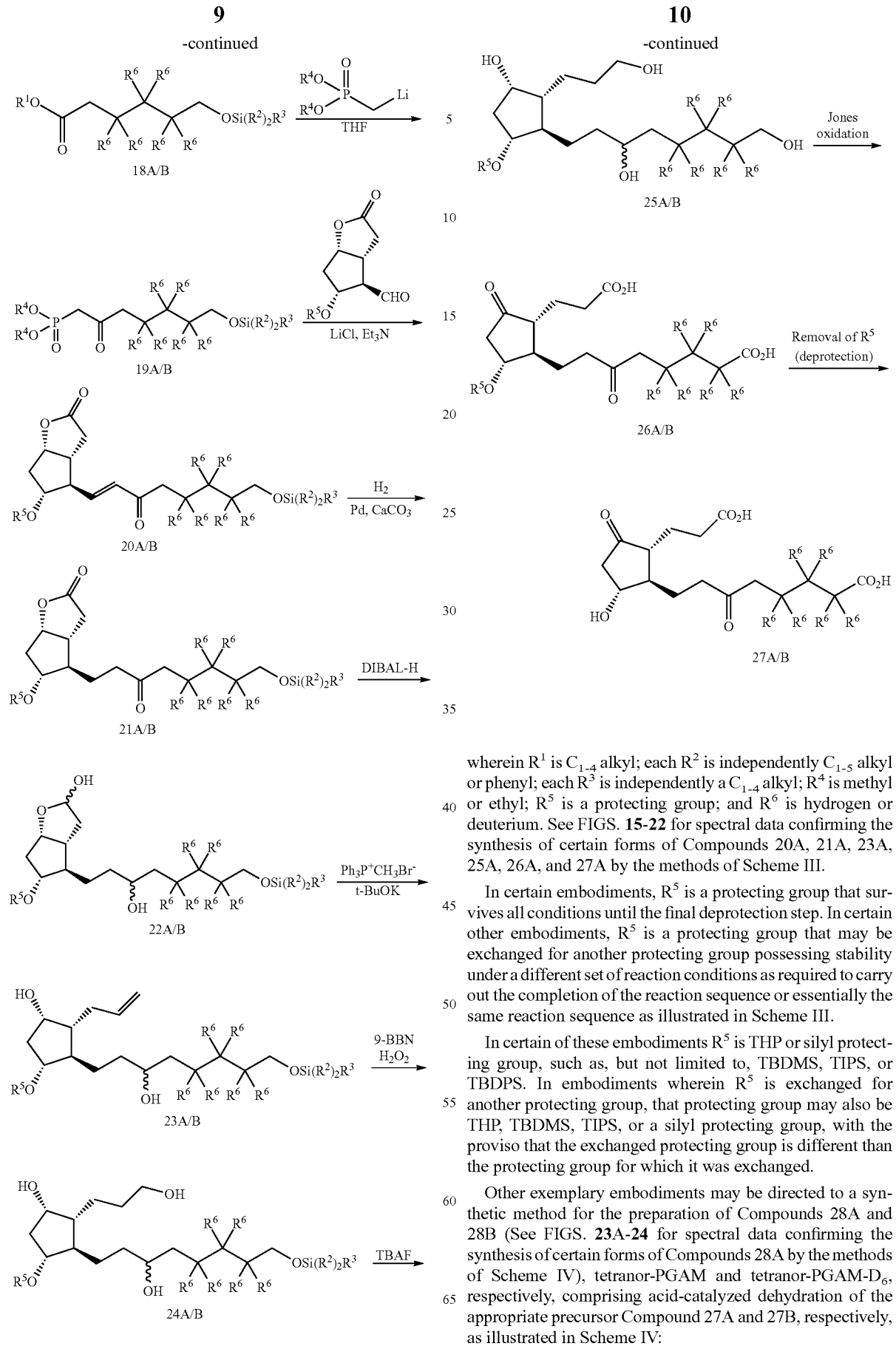

wherein $R^1$ is $C_{1-4}$ alkyl; each $R^2$ is independently $C_{1-5}$ alkyl or phenyl; each $R^3$ is independently a $C_{1-4}$ alkyl; $R^4$ is methyl or ethyl; $R^5$ is a protecting group; and $R^6$ is hydrogen or deuterium. See FIGS. 15-22 for spectral data confirming the synthesis of certain forms of Compounds 20A, 21A, 23A, 25A, 26A, and 27A by the methods of Scheme III.

In certain embodiments, $R^5$ is a protecting group that survives all conditions until the final deprotection step. In certain other embodiments, $R^5$ is a protecting group that may be exchanged for another protecting group possessing stability under a different set of reaction conditions as required to carry out the completion of the reaction sequence or essentially the same reaction sequence as illustrated in Scheme III.

In certain of these embodiments $R^5$ is THP or silyl protecting group, such as, but not limited to, TBDMS, TIPS, or TBDPS. In embodiments wherein $R^5$ is exchanged for another protecting group, that protecting group may also be THP, TBDMS, TIPS, or a silyl protecting group, with the proviso that the exchanged protecting group is different than the protecting group for which it was exchanged.

Figure 23A:
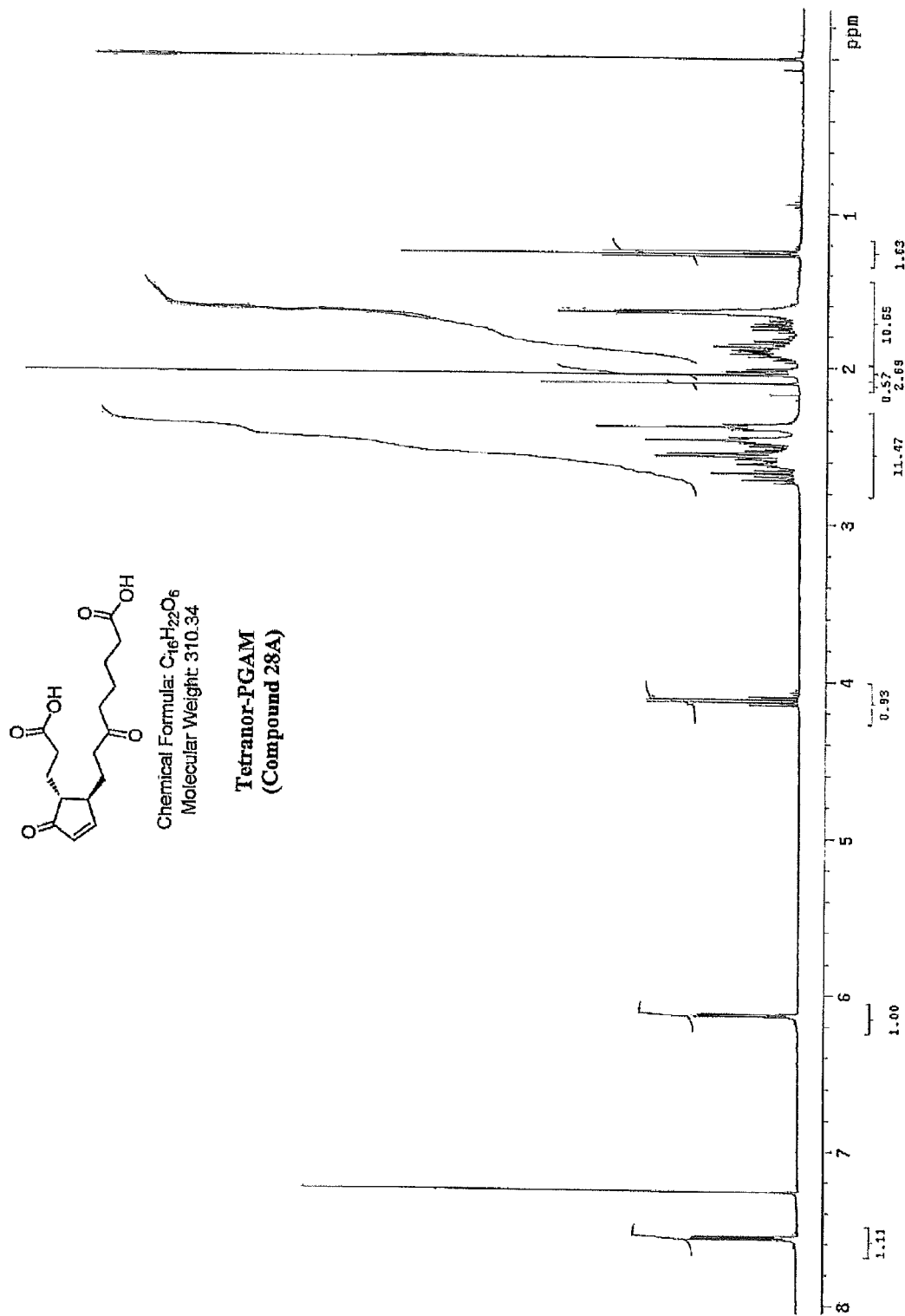
Figure 23B:
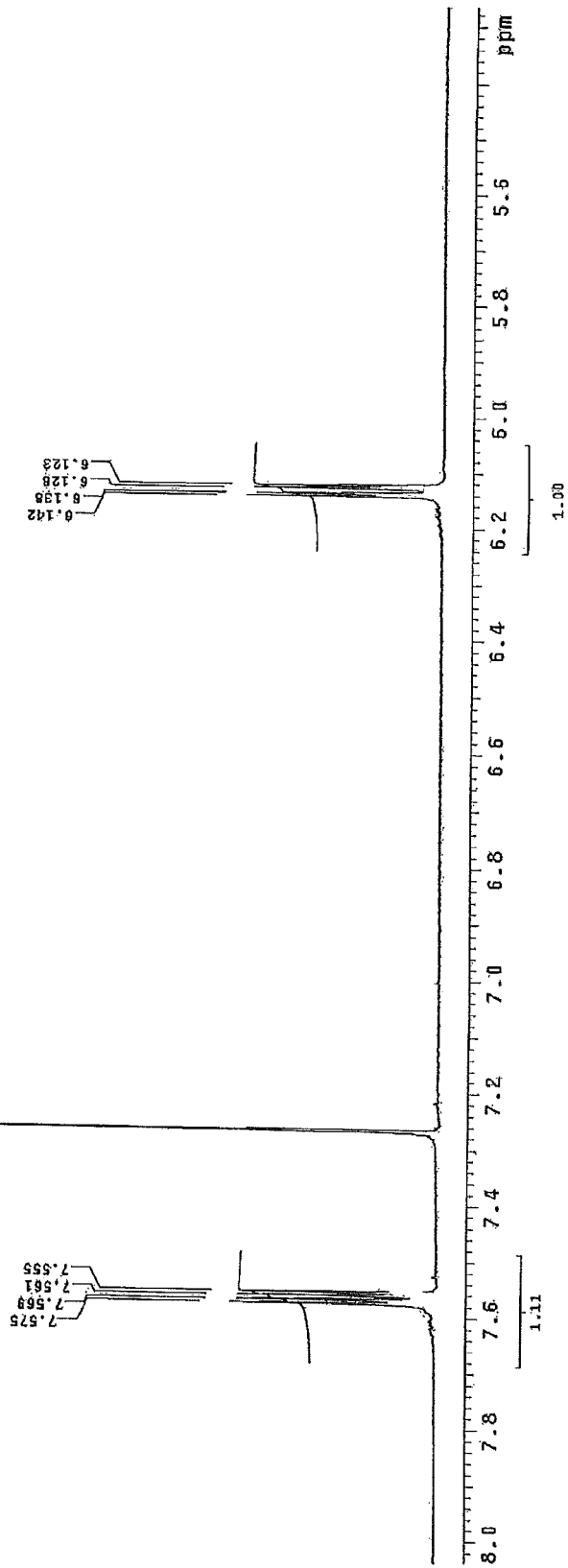
Figure 24:
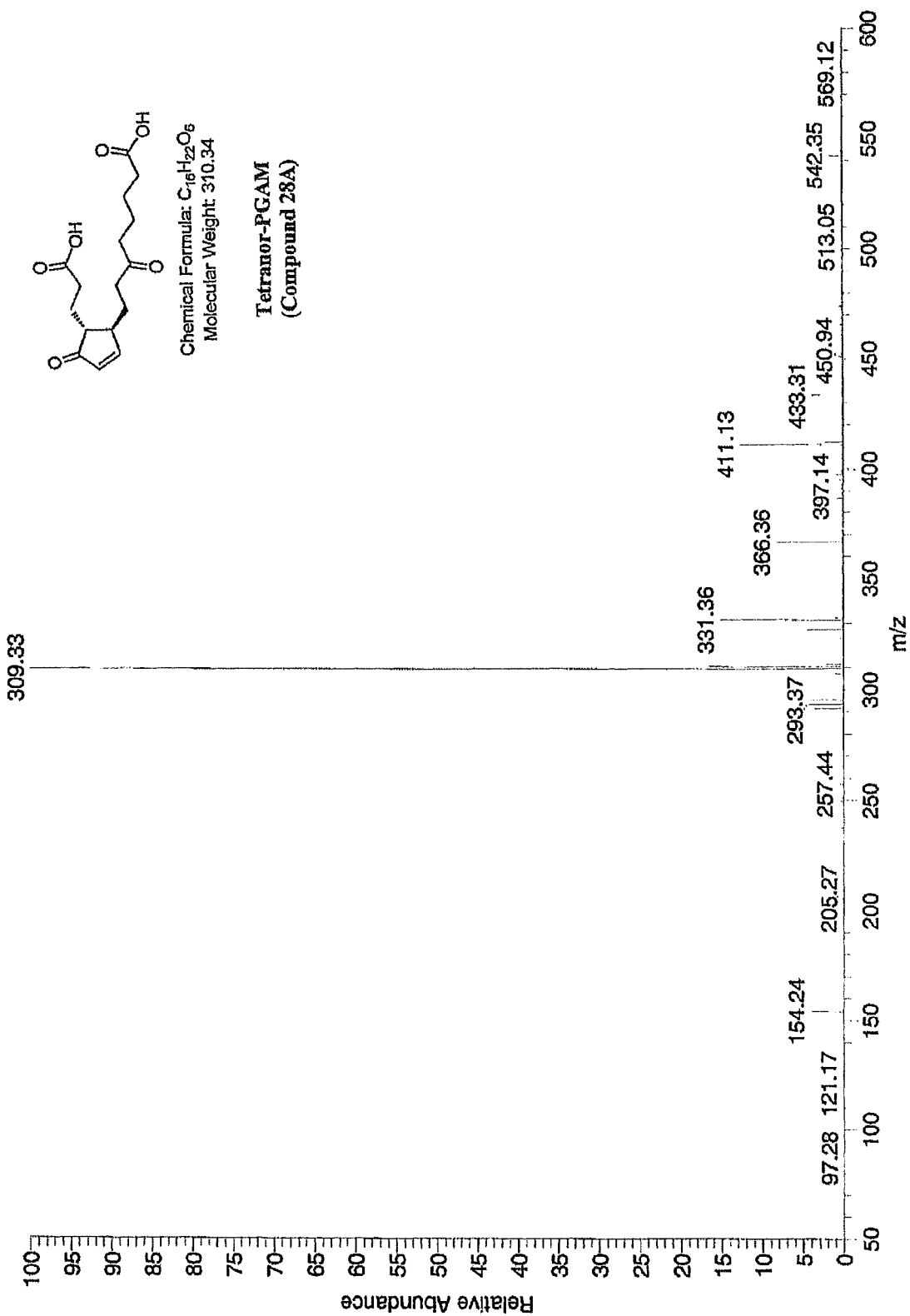
Figure 25A:
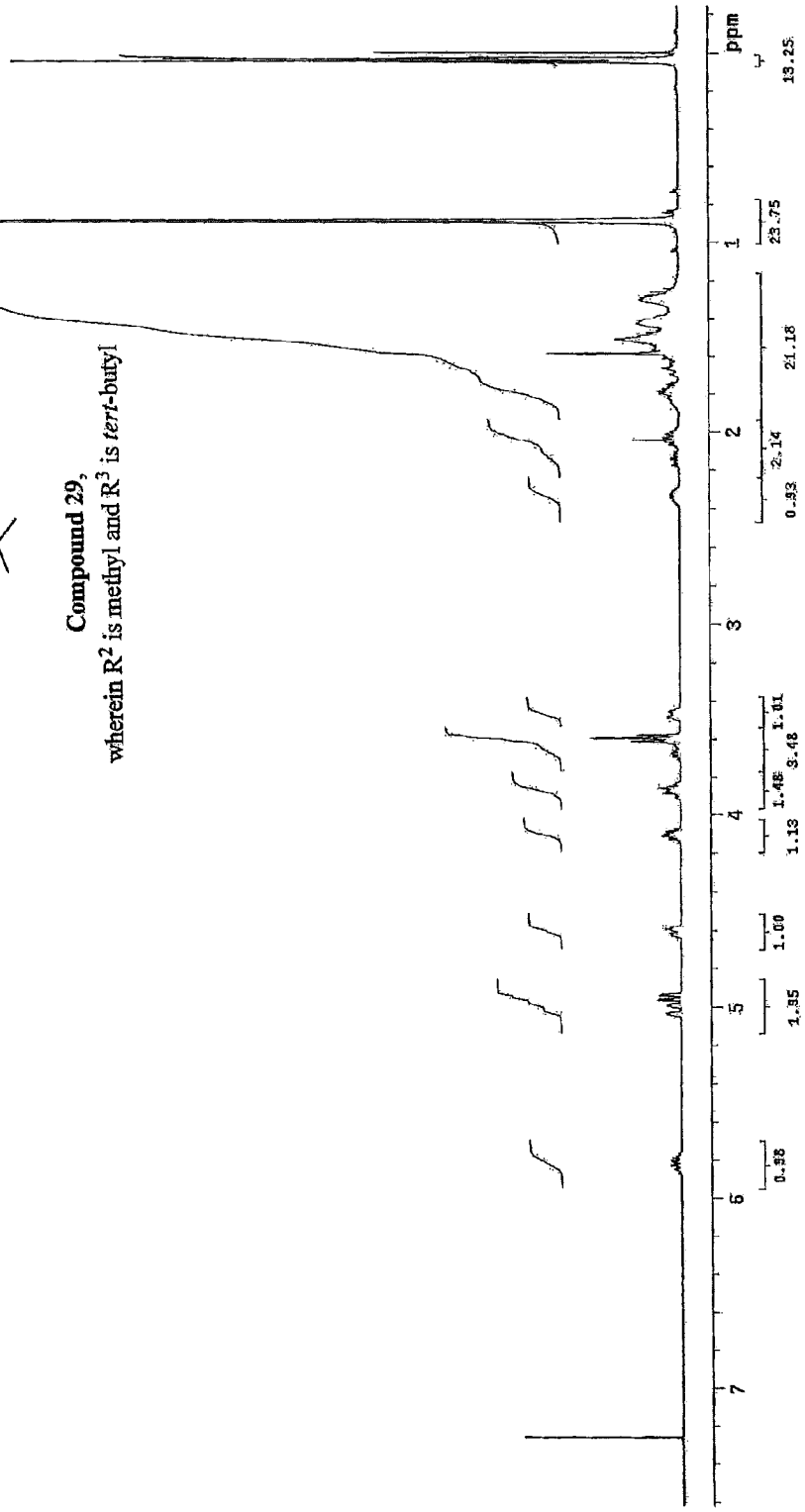
Figure 25B:
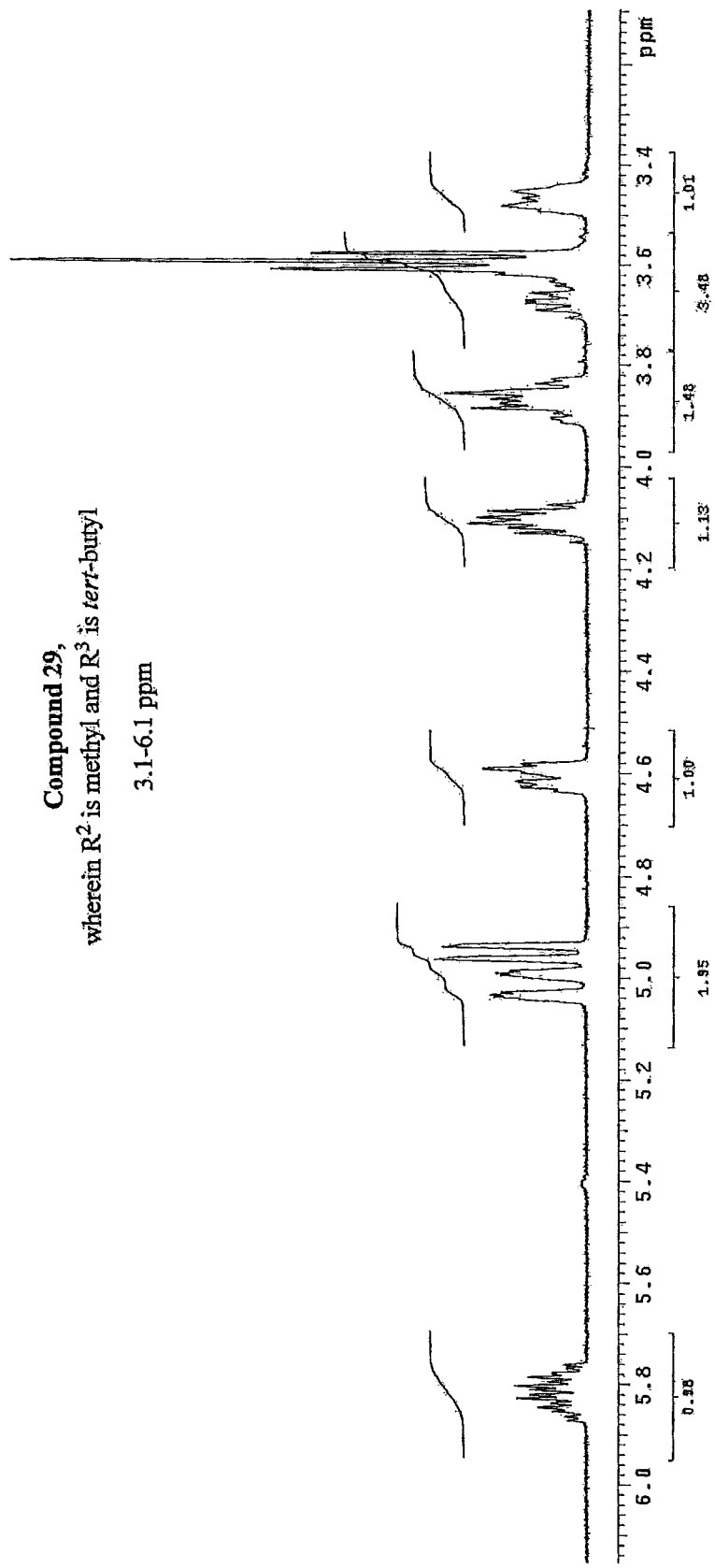
Figure 25D:
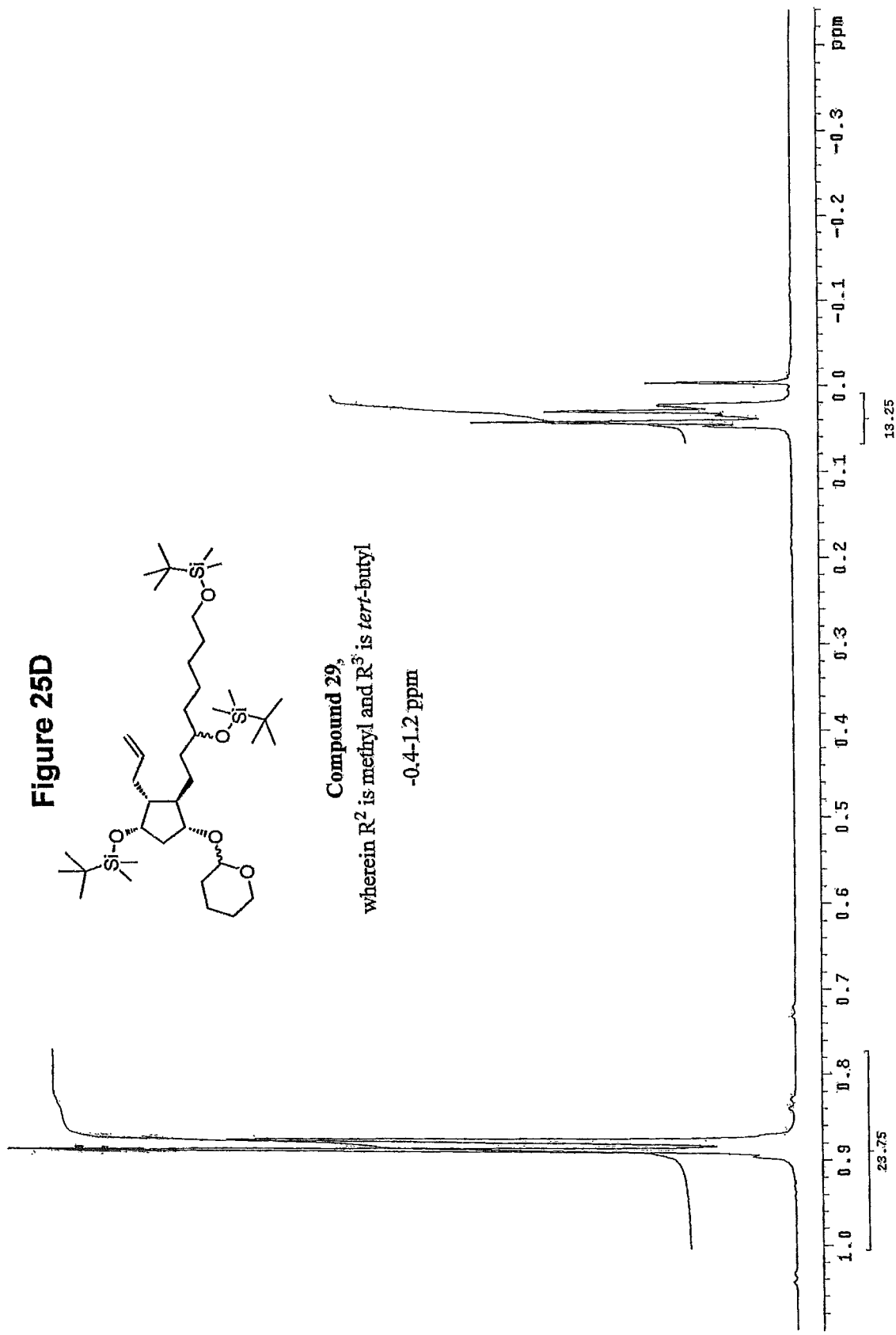

Other exemplary embodiments may be directed to a synthetic method for the preparation of Compounds 28A and 28B (See FIGS. 23A-24 for spectral data confirming the synthesis of certain forms of Compounds 28A by the methods of Scheme IV), tetranor-PGAM and tetranor-PGAM-$D_6$, respectively, comprising acid-catalyzed dehydration of the appropriate precursor Compound 27A and 27B, respectively, as illustrated in Scheme IV:

(Scheme IV)

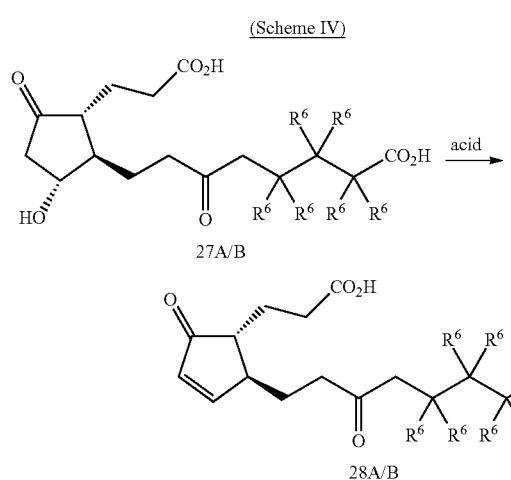

Other exemplary embodiments may be directed to a synthetic route for the preparation of Compound 34, tetranor-PGFM, comprising the reaction steps illustrated in Scheme V (See FIGS. 25A-25D for spectral data confirming the synthesis Compound 29 by the methods of Scheme V):

(Scheme V)

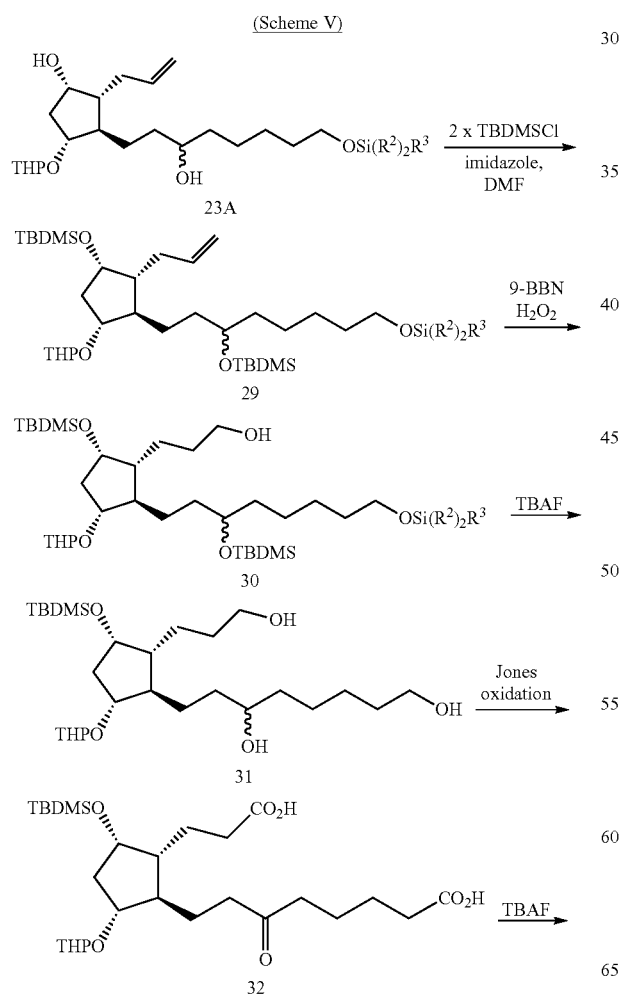

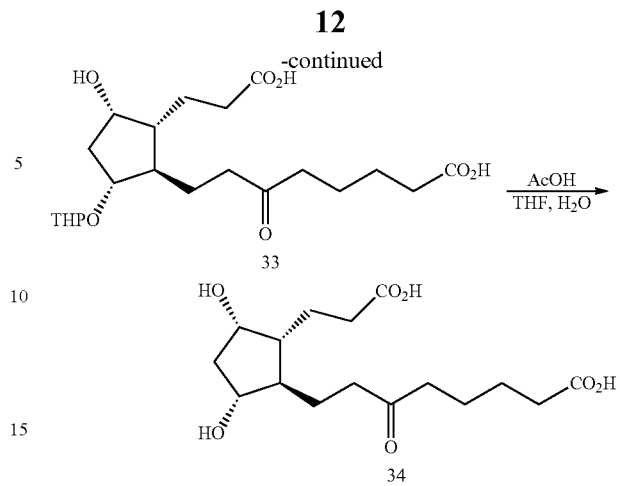

The above description of exemplary embodiments, and examples provided below, are merely exemplary in nature and, thus, variations thereof are not to be regarded as a departure from the spirit and scope of the invention.

EXAMPLES

The Examples provided herein describe embodiments directed to methods for synthesizing various tetranor-PG metabolites.

Example 1

Preparation of Tetranor-PGDM

Preparation of Ester (2A) from 6-hydroxyhexanoate (1A)

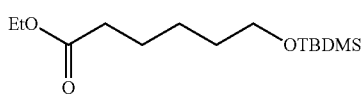

2A
(2, wherein $R^1$ is ethyl,
$R^2$ is methyl, and
$R^3$ is tert-butyl)

50.0 g (312.1 mmol) of ethyl 6-hydroxyhexanoate (1A)
61.15 g (405.72 mmol) of TBDMSCl;
42.5 g (624.2) of imidazole;
500 ml of DMF.

A solution of ethyl 6-hydroxyhexanoate (1A) in dry DMF was cooled with an ice bath and treated with TBDMSCl and imidazole portion wise for 10 minutes. The cooling bath was removed and the reaction mixture was stirred overnight (controlled by TLC, hexane-ethyl acetate 90:10). The next day the reaction mixture was treated with ice (200 g), stirred for 5 minutes, and extracted with H-EA (10:1, 800 ml, 2×200 ml). The combined organic phases were washed with water-brine (1:1, 2×100 ml), brine (100 ml), dried over $Na_2SO_4$, and evaporated. The residue was purified by flash chromatography: Silica gel (300 g), hexane (H)-ethyl acetate (EA) 100:1-

70:1. The mass of the collected product (Ester (2A)) was 81.5 g (95%), TLC Rf=0.8 (solvent system:hexane-ethyl acetate 90:10).

Preparation of Phosphonate (3A) from Ester (2A)

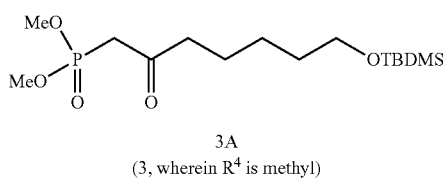 [SMILES: COP(=O)(CC(=O)CCCCCO[Si](C)(C)C(C)(C)C)OC]

3A
(3, wherein $R^4$ is methyl)

41.17 g (150 mmol) of protected ester 2A;
17.88 ml (165 mmol) of dimethyl methylphosphonate;
72.2 ml (195 mmol) of 2.7 M n-BuLi;
500 ml of THF.

A 2.5 M solution of n-BuLi in hexanes was added to a solution of phosphonate in dry THF (450 ml) at −75° C. under a nitrogen blanket ($N_2$). After 3 hours, ester 2A was added in 50 ml of dry THF to the solution and the resultant mixture (RM) was stirred 1 hour at the same temperature. The mixture was then allowed to sit overnight at room temperature. 200 ml of $NH_4Cl$ aqueous solution was then added to the mixture and the resultant mixture was extracted with ethyl acetate (3×200 ml), washed with brine, dried over $MgSO_4$, and evaporated. The residue remaining after evaporation was purified by flash chromatography:Silica gel (1000 g), $CH_2Cl_2$-MeOH 100:1. The mass of the collected product (Phosphonate (3A)) was 26.2 g (57%), $R_f$=0.5 ($CH_2Cl_2$-MeOH 95:5).

Preparation of PG-Lactone (4A) from Phosphonate (3A)

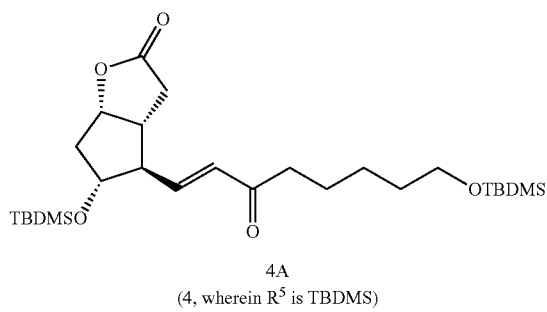 [SMILES: CC(C)(C)[Si](C)(C)OCCCCCC(=O)/C=C/[C@@H]1[C@H]2CC(=O)O[C@H]2C[C@H]1O[Si](C)(C)C(C)(C)C]

4A
(4, wherein $R^5$ is TBDMS)

23.77 g (67.4 mmol) of phosphonate 3A;
18.27 g (64.23 mmol) of Corey aldehyde;
2.72 g (64.23 mmol) of LiCl;
8.95 ml (64.23 mmol) of TEA (triethyl amine);
300 ml of THF.

A solution of phosphonate 3A and Corey aldehyde in dry THF was treated with LiCl and stirred at room temperature until the resultant mixture become a clear solution (10-15 minutes). The mixture was then cooled to −10° C. and treated with TEA drop wise for 5 minutes under a nitrogen blanket ($N_2$). The resulting slurry was stirred for 1 hour at the same temperature and then the cooling bath was removed. The resultant mixture was then stirred overnight at room temperature. The next day, 100 ml of $NH_4Cl$ aqueous solution was added to the reaction mixture and the resultant mixture was extracted with ethyl acetate. The combined organic phases were then washed with brine, dried over $MgSO_4$, and evaporated. The residue after evaporation was purified by flash chromatography: Silica gel (600 g), H-EA 10:1-5:1. The mass of the collected product (PG Lactone (4A)—See FIG. 1) was 21.5 g (65%), $R_f$=0.7 (H-EA 70:30). See FIG. 1.

Preparation of Lactone (5A) from PG-Lactone (4A)

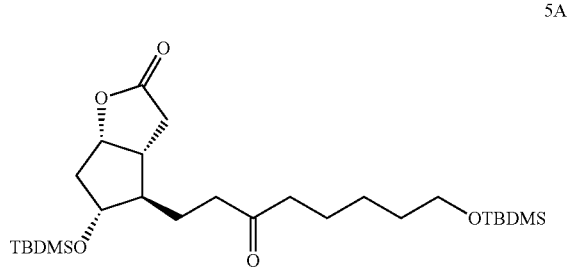 [SMILES: CC(C)(C)[Si](C)(C)OCCCCCC(=O)CC[C@@H]1[C@H]2CC(=O)O[C@H]2C[C@H]1O[Si](C)(C)C(C)(C)C]

5A 21.7 g (42.48 mmol) of PG-lactone 4A;
4.0 g of $Pd/CaCO_3$;
400 ml of ethyl acetate.

A solution of PG-lactone 4A in ethyl acetate (EA) was treated with a catalyst and the resulting suspension was stirred under $H_2$ (balloon) overnight. The catalyst was then filtered through Celite, and the filtrate was evaporated and the remaining residue was used further without purification. Crude product (Lactone (5A)—See FIG. 2)—21.2 g, $R_f$=0.75 (H-EA 65:35).

Preparation of Lactone (6A) from Lactone (5A)

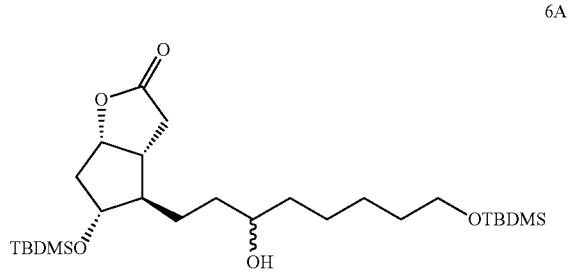 [SMILES: CC(C)(C)[Si](C)(C)OCCCCCC(O)CC[C@@H]1[C@H]2CC(=O)O[C@H]2C[C@H]1O[Si](C)(C)C(C)(C)C]

6A 21.1 g (41.15 mmol) of lactone 5A;
1.56 g (41.15 mmol) of $NaBH_4$;
100 ml of MeOH;

A solution of lactone 5A in dry methanol was cooled to −7° C. and treated with $NaBH_4$ portion wise for 30 minutes. The reaction mixture was then treated with $NH_4Cl$ aqueous solution. The cooling bath was removed and the resultant mixture was extracted with diethyl ether. The combined organic phases were washed with brine, dried over $MgSO_4$, and evaporated. The residue remaining after evaporation was used further without purification. Crude product (Lactone 6A—See FIG. 3)—21.18 g, $R_f$=0.5 (H-EA 60:40).

Preparation of Lactone (7A) from Lactone (6A)

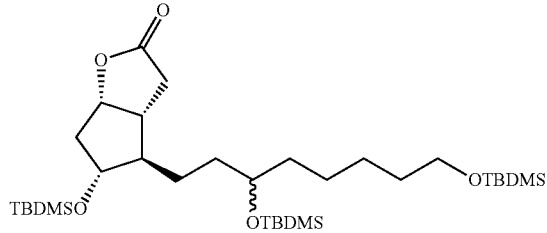

7A 21.18 g (41.15 mmol) of lactone 6A;
9. g (61.73 mmol) of TBDMSCl;
6.16 g (90.5) of imidazole;
300 ml of DMF.

A solution of lactone 6A in dry DMF was cooled with an ice bath and treated with TBDMSCl and imidazole portion wise for 10 minutes. The cooling bath was removed and the reaction mixture was stirred overnight (controlled by TLC, H-EA 80:20). The next day, the reaction mixture was treated with ice (200 g), stirred for 5 minutes, and extracted with ethyl acetate. The combined organic phases were washed with water-brine (1:1, 2×100 ml), brine (100 ml), dried over $Na_2SO_4$, and evaporated. The remaining residue was purified by flash chromatography:Silica gel (600 g), H-EA 50:1-20:1. The mass of the collected product (Lactone (7A)—See FIG. 4) was 25.6 g (95% after 3 steps), $R_f$=0.8 (H-EA 80:20).

Preparation of Lactone (8A) from Lactone (7A)

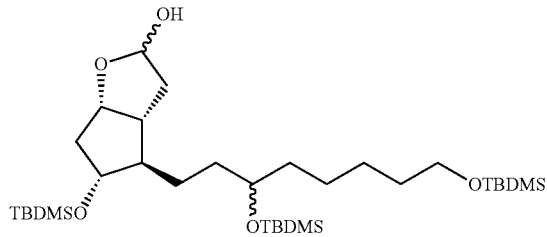

8A 25.5 g (40.5 mmol) of lactone 7A;
52.7 ml of DIBAl-H (1 M solution in toluene);
600 ml of toluene;
50 ml of THF—$H_2O$ 7:1 mixture.

A solution of lactone 7A in dry toluene was cooled to −70° C. and DIBAL was added drop wise under a nitrogen blanket ($N_2$). The reaction mixture was then stirred for 1 hour and TLC (H-EA 85:15) showed no starting material. The reaction mixture was then treated with ethyl acetate (3 ml), followed with a THF—$H_2O$ mixture. The cooling bath was removed and the reaction mixture was stirred for 2 hours. During this time a precipitate was formed, which was filtered and washed with toluene. The filtrate was then evaporated to give 27 g of pure lactol (Lactone (8A)), which was used for the next step without purification. $R_f$=0.5 (H-EA 85:15).

Preparation of Olefin A from Lactone (8A)

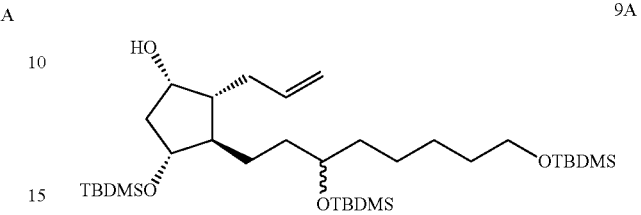

9A 27.0 g (crude) (40.5 mmol) of lactol 8A;
40.53 ml of n-BuLi (2.5 M solution in hexanes, 101.33 mmol);
33.3 g (93.22 mmol) of methyltriphenylphosphonium bromide;
500 ml of THF.

Methyltriphenylphosphonium bromide was placed in 1 liter 3-neck flame dried round bottom flask. Dry THF (450 ml) was added to the salt, and the suspension was cooled in an ice bath. While the suspension was being stirred, n-BuLi was added under a nitrogen ($N_2$) atmosphere. The ice bath was removed and the orange reaction mixture was stirred for 30 minutes at room temperature. Lactol 8A was added (in 50 ml of dry THF) to the reaction mixture and the reaction mixture was stirred overnight. The next day, the yellow reaction mixture was quenched with an aqueous solution of $NH_4Cl$ (200 ml), stirred for 10 minutes, and diluted with 500 ml of ethyl acetate. The water phase was separated and extracted with ethyl acetate. The combined organic phases were washed with brine, dried over $MgSO_4$, and evaporated. The remaining residue was purified by flash chromatography: Silica gel (1 kg), H-EA 50:1-30:1. The mass of the collected product (Olefin (9A)—See FIGS. 5A-5C and 6) was 22.9 g (90% after 2 steps), $R_f$=0.7 (H-EA 95:5).

Preparation of Triol (10A) from Olefin (9A)

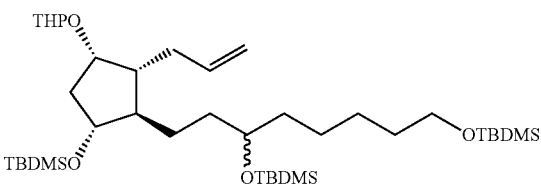

10A 1.05 g (1.67 mmol) of olefin 9A;
0.3 ml (3.33 mmol) of dihydropyran;
21 mg (0.08 mmol) of PPTS (pyridinium p-toluenesulfonate);
20 ml of $CH_2Cl_2$.

A solution of olefin 9A in dry $CH_2Cl_2$ was treated with dihydropyrane and PPTS. The resulting mixture was stirred overnight at room temperature. The next day the reaction mixture was washed with an aqueous solution of $NaHCO_3$ and brine, dried over $MgSO_4$, and evaporated. The remaining residue was purified by flash chromatography: Silica gel (24 g), H-EA 100:1-50:1. The mass of the collected product (Triol (10A)—See FIG. 7) was 0.95 g (80%, $R_f$=0.8 (H-EA 95:5).

Preparation of Pentaol (11A) from Triol (10A)

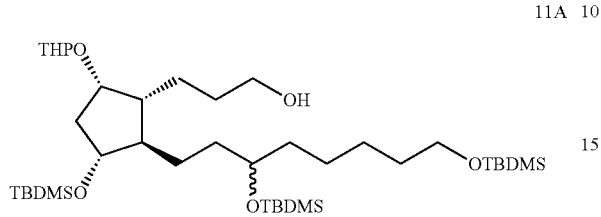

11A 0.95 g (1.33 mmol) of triol 10A;
12.0 ml of 9-BBN (0.5 M solution in THF, 6.0 mmol)
1.5 ml Of NaOH (4 N solution);
1.53 ml of $H_2O_2$ (50%, 26.6 mmol);
40 ml of THF.

A solution of olefin 10A in THF was cooled by an ice bath and 9-BBN was added drop wise under a nitrogen ($N_2$) blanket. After 1 hour, the cooling bath was removed and the reaction mixture was stirred for two hours. The reaction mixture was then cooled by an ice bath and NaOH was added followed by $H_2O_2$. The reaction mixture was stirred for two hours, diluted with ethyl acetate (100 ml), and moved to a funnel. The reaction mixture was then washed with brine (2×20 ml), dried over $MgSO_4$, and evaporated. The remaining residue was purified by flash chromatography: Silica gel (60 g), H-EA 20:1-10:1. The mass of the collected product (Pentaol (11A)—See FIGS. 8A-8C) was 0.72 g (75%, $R_f$=0.5 (H-EA 80:20).

Preparation of Tetraol (12A) from Pentaol (11A)

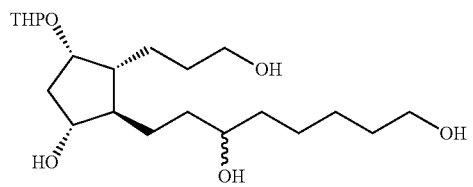

12A 0.61 g (0.83 mmol) of tri-TBS pentaol 11A;
5.8 ml of TBAF (1.0 M solution in THF, 5.8 mmol);
3 ml of THF.

TBAF was added to a solution of tri-TBS pentaol 11A in THF, and the reaction mixture was stirred overnight. The next day 30 ml of ethyl acetate was added to the reaction mixture and the reaction mixture was then washed with brine (2×20 ml), dried over $MgSO_4$, and evaporated. The residue was purified by flash chromatography:Silica gel (24 g), $CH_2Cl_2$-MeOH 20:1. The mass of the collected product (Tetraol (12A)—See FIG. 9A-9C) was 0.26 g (78%), $R_f$=0.5 ($CH_2Cl_2$-MeOH 90:10).

Preparation of Protected Tetranor PGDM (13A) from Tetraol (12A)

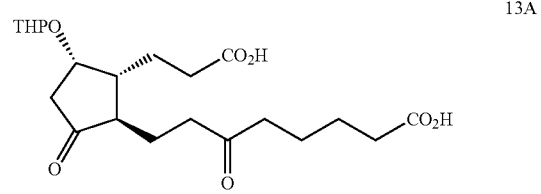

13A 255 mg (0.66 mmol) of tetraol 12A;
Jones reagent (2.66 M solution in $H_2O$);
20 ml of acetone.

A solution of tetraol 12A in acetone (10 ml) was treated with Jones reagent (5 portions of freshly diluted with acetone in 5:1 ratio) at 0° C. for 40 minutes until the color of the reaction mixture became yellow and did not disappear for 10 minutes. The reaction mixture was then stirred for 10 minutes more, treated with 0.5 ml of i-PrOH, diluted with 100 ml of ethyl acetate, dried over $MgSO_4$, and evaporated. The residue was purified by flash chromatography: Silica gel (120 g), H-EA-HOAc 70:30:0.5. The mass of the collected product (Protected tetranor PGDM (13A)) was 110 mg (40%). $R_f$=0.5 (H-EA-HOAc 15:85:1).

Preparation of Tetranor PGDM (14) from Protected Tetraol PGDM (13A)

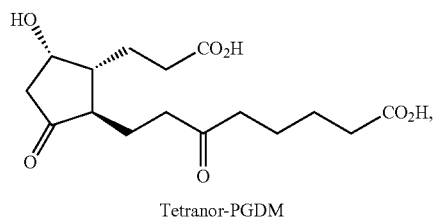

14

Tetranor-PGDM 180 mg (0.44 mmol) of protected tetranor PGDM;
0.4 ml (0.52 mmol) of 10% TFA in $CH_2Cl_2$
2 ml of $CH_2Cl_2$.

A solution of protected tetranor PGDM (13A) (in 2 ml of $CH_2Cl_2$) was treated with 10% TFA (in $CH_2Cl_2$) and stirred overnight at room temperature. The next day the remaining residue after evaporation was purified by flash chromatography:Silica gel (8 g), H-EA-HOAc 70:30:0.5-30:70:0.5%. The mass of the collected product (Tetranor PGDM (14)—See FIG. 12) was 70 mg (50%). $R_f$=0.35 (H-EA-HOAc 10:90:1).

Example 2

Preparation of Tetranor-PGJM (Compound (15))

A solution of Tetranor-PGDM (Compound 14) in 2 ml of $CH_2Cl_2$ was treated with TFA and stirred overnight at room temperature. The next day the remaining residue after evaporation was purified by flash chromatography: Silica gel (4 g), H-EA-HOAc 60:40:0.5-50:50:0.5%. The mass of the collected product ((Compound (15)—See FIGS. 13 and 14A-B) was 26 mg (46%). $R_f$=0.75 (H-EA-HOAc 15:85:1)

Example 3

Preparation of Tetranor-PGEM-$D_6$, Compound (27B)

Preparation of Ester (17B-1) from Sodium Salt (16B)

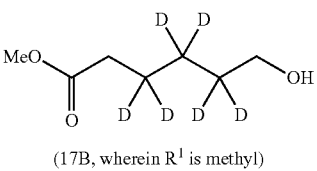

(17B, wherein $R^1$ is methyl)

2.0 g (12.49 mmol) of sodium salt 16B;

5% $KHSO_4$ aq. s-n;

$CH_2N_2$ in ether (about 75 ml obtained from Diazald by standard procedure from Organic Synthesis).

A saturated, aqueous solution of sodium salt 16B was treated with 5% aqueous solution of $KHSO_4$ until a pH of about 1 was achieved. The solution was then extracted 4 times with ethyl acetate. The organic phase was washed with brine, dried over $Na_2SO_4$, and evaporated. The remaining residue (1.86 g) was dissolved in 20 ml of ether and treated portion wise with an ether solution of $CH_2N_2$ until the color of reaction mixture become yellow. The remaining residue (ester 17B-1) after evaporation (1.85 g, 95% yield) was used for the next step without purification.

Preparation of Protected Ester (18B-1a) from Ester (17B-1)

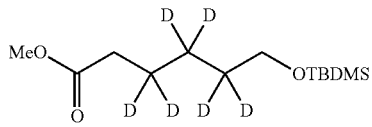

(18B-1, wherein $R^2$ is methyl and $R^3$ is tert-butyl)

1.8 g (11.8 mmol) of hydroxy ester 17B-1;

2.14 g (14.2 mmol) of TBDMSCl;

1.00 g (14.75) of imidazole;

20 ml of DMF.

The ester 17B-1 was dissolved in DMF. TBDMSCl and imidazole was then added and the reaction mixture was stirred overnight (controlled by TLC, hexane-ethyl acetate 10:1). The reaction mixture was then diluted with 200 ml of ethyl acetate, washed with brine (2×100 ml), dried over $Na_2SO_4$, and evaporated. The remaining residue was purified by flash chromatography:Silica gel (250 g), hexane-ether 50:1-20:1. The mass of the collected product (Ester 18-B-1a (i)) was 2.44 g (80%), $R_f$=0.55 (hexane-ethyl acetate 10:1).

Preparation of Protected Ester (19B-1a(i)) from Protected Ester (18B-1a)

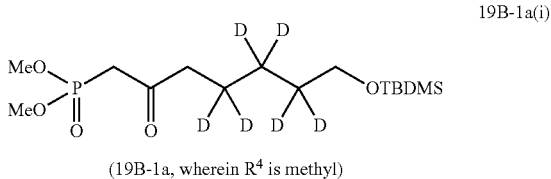 [SMILES: [2H]C([2H])(CO[Si](C)(C)C(C)(C)C)C([2H])([2H])C([2H])([2H])CC(=O)CP(=O)(OC)OC]

(19B-1a, wherein $R^4$ is methyl)

2.44 g (9.16 mmol) of protected ester 18B-1a;

1.02 ml (9.43 mmol) of dimethyl methylphosphonate;

3.66 ml (9.16 mmol) of 2.5 M n-BuLi;

50 ml of THF.

A 2.5 M solution of n-BuLi in hexanes was added to the solution of phosphonate in THF (45 ml) at −75° C. under a nitrogen ($N_2$) blanket. After 40 minutes, ester 18B-1a was added in 5 ml of THF to the reaction mixture and the reaction mixture was stirred for 1 hour at −75° C. and 1 hour at room temperature. 20 ml of an aqueous solution of $NH_4Cl$ aq. was added and the reaction mixture was extracted with ethyl acetate (3×100 ml), washed with brine, dried over $MgSO_4$, and evaporated. The remaining residue (Phosphonate (19B-1a(i)) after evaporation (3.08 g, 95% yield) was used for the next step without purification.

Preparation of PG-Lactone (20B-1a(i)) from Phosphonate (19B-1a(i))

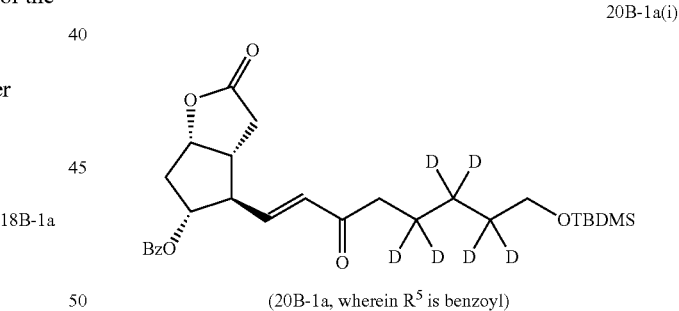

(20B-1a, wherein $R^5$ is benzoyl)

3.07 g (8.6 mmol) of phosphonate 19B-1a(i);

2.235 g (8.14 mmol) of Corey aldehyde;

0.37 g (8.6 mmol) of LiCl;

1.2 ml (8.6 mmol) of TEA (triethyl amine);

30 ml of THF.

LiCl and Corey aldehyde in THF TEA* were added at −10° C. under $N_2$ drop wise to a suspension of phosphonate 19B-1a(i). The reaction mixture was then stirred at −10° C., wherein the cooling bath was removed. The reaction mixture was then stirred overnight at room temperature. The next day, 10 ml of an aqueous solution of $NH_4Cl$ was added to the reaction mixture. The reaction mixture was then extracted with ethyl acetate, washed with brine, dried over $MgSO_4$, and evaporated. The remaining residue after evaporation (4.48 g) was purified by flash chromatography:Silica gel (200 g), hexane-ethyl acetate 5:1-2:1. The mass of the collected product (PG-lactone 20B-1a(i)) was 2.34 g (54%), $R_f$=0.6 (hexane-ethyl acetate 60:40).

*Alternatively, LiCl-TEA may be used in excess (1.2-1.5 molar equivalents).

Preparation of PG-Lactone (21B-1a(i)) from PG-Lactone (20B-1a(i))

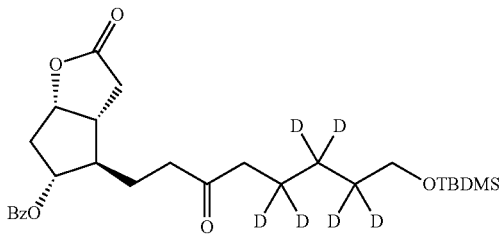

21B-1a(i)

2.34 g (4.6 mmol) of PG-lactone 20B-1a(i);
0.7 g of Pd/C;
50 ml of ethyl acetate.

PG-lactone 20B-1a(i) was first dissolved in ethyl acetate. The reaction flask was flashed with $N_2$ and a catalyst was added carefully portion wise to the reaction mixture. The reaction mixture was stirred with $H_2$ for two hours, resulting in the removal of about 105 ml of $H_2$. The catalyst was filtered off, and the reaction mixture was washed with ethyl acetate. The filtrate was evaporated and purified by flash chromatography:Silica gel (80 g), hexane-ethyl acetate 3:1-2:1. The mass of the collected product (PG-Lactone 21B-1a(i)) was 2.15 g (91%), $R_f$=0.55 (hexane-ethyl acetate 60:40).

Preparation of Lactone (21B-1a(ii)) from PG-Lactone (21B-1a(i))

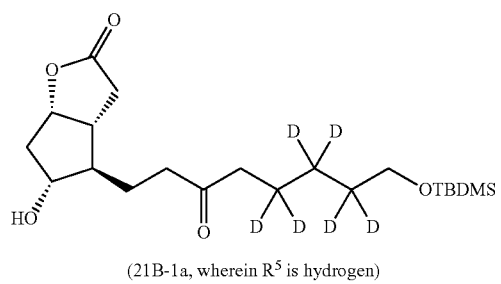

21B-1a(ii)

(21B-1a, wherein $R^5$ is hydrogen)

2.15 g (4.2 mmol) of PG-lactone 21B-1a(i);
0.58 g (4.2 mmol) of $K_2CO_3$;
30 ml of MeOH.

Lactone 21B-1a(i) was dissolved in MeOH and stirred with $K_2CO_3$ for 5 hours (controlled by TLC, hexane-ethyl acetate 50:50). The reaction mixture was then diluted with 200 ml of ethyl acetate, washed with brine (2×100 ml), dried over $MgSO_4$, and evaporated. The remaining residue (2.23 g) was purified by flash chromatography:Silica gel (80 g), hexane-ethyl acetate 2:1-1:1. The mass of the collected product (Lactone 21B-1a(ii)) was 1.34 g (81%), $R_f$=0.3 (hexane-ethyl acetate 50:50).

Preparation of Lactone (21B-1a(iii)) from PG-Lactone (21B-1a(ii))

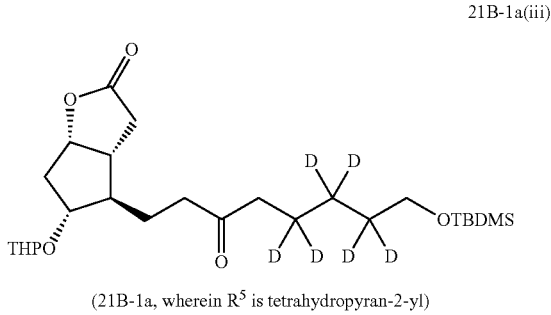

21B-1a(iii)

(21B-1a, wherein $R^5$ is tetrahydropyran-2-yl)

1.33 g (0.22 mmol) of lactone 21B-1a(ii);
0.62 ml (6.82 mmol) of dihydropyrane;
43 mg (0.17 mmol) of PPTS (pyridinium p-toluenesulfonate);
40 ml of $CH_2Cl_2$.

Lactone 21B-1a(ii), dihydropyrane, PPTS and $CH_2Cl$ were mixed together and stirred overnight. The next day the reaction mixture was washed with an aqueous solution of $NaHCO_3$, brine, dried over $MgSO_4$, and evaporated. The remaining residue (1.72 g) was purified by flash chromatography:Silica gel (80 g), hexane-ethyl acetate 3:1-1:1. The mass of the collected product (Lactone (21B-1a(iii))) was 1.495 g (93%), $R_f$=0.7 (hexane-ethyl acetate 1:1).

Preparation of Lactol (22B-1a(iii)) from PG-Lactone (21B-1a(iii))

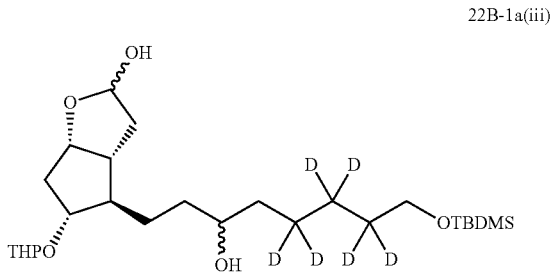

22B-1a(iii)

1.49 g (3.05 mmol) of lactone 21B-1a(iii);
8.2 ml of DIBAl-H (1 M solution in toluene);
100 ml of toluene;
15 ml of THF—$H_2O$ 2:1 mixture.

A solution of lactone 21B-1a(iii) in toluene was cooled to −70° C. and DIBAL was added drop wise under a nitrogen ($N_2$) blanket. The reaction mixture was stirred for 1 hour and TLC ($CH_2Cl_2$-MeOH 20:1) showed no starting materials. A mixture of THF—$H_2O$ was added to the reaction flask, wherein the cooling bath was removed and the reaction mixture was stirred for 2 hours. During this time a precipitate was formed. The precipitate was filtered and washed with toluene. The filtrate (Lactol (22B-1a(iii))) was then evaporated to give 1.6 g (>98%) of pure lactole, which was used for the next step without purification. $R_f$=0.65 ($CH_2Cl_2$-MeOH 20:1).

Preparation of Olefin (23B-1a(iii)) from Lactol (22B-1a(iii))

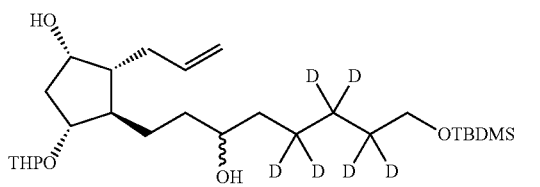

23B-1a(iii)

1.6 g (3.05 mmol) of lactol 22B-1a(iii);
4.3 ml of n-BuLi (2.5 M solution in hexanes);
3.8 g (10.7 mmol) of methyltriphenylphosphonium bromide;
50 ml of THF.

Methyltriphenylphosphonium bromide was placed in 100 ml 3-neck flame dried round bottom flask, THF was added to the salt, and the resultant, suspension was cooled by and ice bath. n-BuLi was added to the reaction mixture while the reaction mixture was being stirred under a nitrogen ($N_2$) atmosphere. The icebath was removed and an orange reaction mixture was stirred for 30 minutes at room temperature. Lactol 22B-1a(iii) was added in 10 ml of THF to the orange reaction mixture was stirred overnight. The next day a yellow reaction mixture was quenched with an aqueous solution of $NH_4Cl$, stirred for 10 minutes, and diluted with 150 ml of ethyl acetate. The water phase was separated and extracted with ethyl acetate. The combined organic phases were washed with brine, dried over $MgSO_4$, and evaporated. The remaining residue (2.78 g) was purified by flash chromatography:Silica gel (80 g), hexane-ethyl acetate 3:1-1:1. The mass of the collected product (Olefin (23B-1a(iii))) was 1.04 g (70%), $R_f$=0.8 ($CH_2Cl_2$-MeOH 20:1).

Alternatively, methyltriphenylphosphonium bromide may be used in excess up to 10 molar equivalents with corresponding excess of the n-BuLi base up to 11 molar equivalents.

Preparation of Triol (24B-1a(iii)) from Olefin (23B-1a(iii))

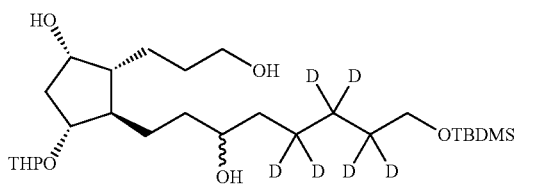

24B-1a(iii)

0.33 g (0.678 mmol) of olefin 23B-1a(iii);
6.1 ml of 9-BBN (0.5 M solution in THF)
NaOH 1.0 ml (3 M solution);
0.8 ml of $H_2O_2$ (50%);
20 ml of THF.

A solution of olefin 23B-1a(iii) in THF was cooled by an ice bath and 9-BBN was added drop wise to the solution under a nitrogen ($N_2$) blanket. After 1 hour, the cooling bath was removed and the reaction mixture was stirred for two hours. The reaction mixture was then cooled by an ice bath and NaOH was added followed by $H_2O_2$. The reaction mixture was stirred for two hours, diluted with ethyl acetate (100 ml) and moved to the funnel. The reaction mixture was washed with brine (2×20 ml), dried over $MgSO_4$, and evaporated. The remaining residue (0.97 g) was purified by flash chromatography:Silica gel (80 g), $CH_2Cl_2$-MeOH 30:1-20:1. The mass of the collected product (Triol (24B-1a(iii))) was 0.35 g (the yield is quantitative), which was used for the next step without purification. $R_f$=0.3 ($CH_2Cl_2$-MeOH 10:1).

Preparation of Tetraol (25B-1a(iii)) from Triol (24B-1a(iii))

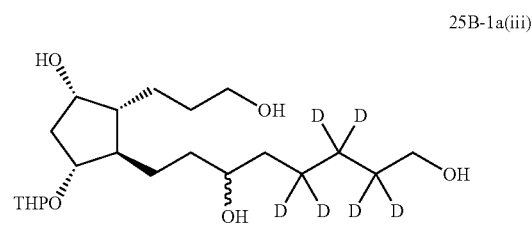

25B-1a(iii)

0.345 g (~0.678 mmol) of crude 24B-1a(iii);
1.0 ml of TBAF (1.0 M solution in THF);
10 ml of THF.

TBAF was added to a solution of triol 24B-1a(iii) in THF and the reaction mixture was stirred overnight. The next day, 50 ml of ethyl acetate was added to the reaction mixture and the reaction mixture was washed with brine (2×20 ml), dried over $MgSO_4$, and evaporated. The remaining residue (0.55 g) was purified by flash chromatography:Silica gel (60 g), MeOH-ethyl acetate-HOAc 5:95:0.5-20:80:0.5. The mass of the collected product (Tetraol (25B-1a(iii))) was 224 mg (83% after two steps). $R_f$=0.4 (MeOH-ethyl acetate-HOAc 5:95:1).

Preparation of Tetranor PGEM (26B-1a(iii)) from Tetraol (25B-1a(iii))

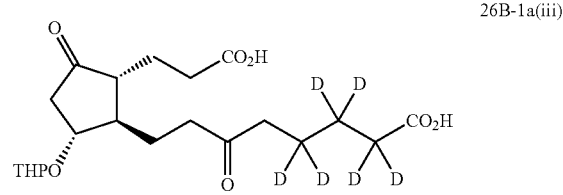

26B-1a(iii)

214 mg (0.57 mmol) of tetraol 25B-1a(iii);
Jones reagent (2.66 M solution in $H_2O$);
70 ml of acetone.

A solution of tetraol 25B-1a(iii) in acetone (20 ml) was treated with Jones reagent (5 portions of freshly diluted with acetone in 50:1 ratio) at 0° C. for 40 minutes until the color of the reaction material become yellow and did not disappear for 10 minutes. The reaction mixture was stirred 10 minutes more, treated with 0.5 ml of i-PrOH, diluted with 150 ml of ethyl acetate, dried over $MgSO_4$, and evaporated. The residue (0.248 g) was purified by flash chromatography:Silica gel (60 g), hexane-ethyl acetate-HOAc 60:40:0.5-20:80:0.5. The mass of the collected product (Tetranor PGEM (26B-1a(iii))) was 46 mg (18%). $R_f$=0.57 (hexane-ethyl acetate-HOAc 10:90:1).

Preparation of Tetranor PGAM (27(B)) from Tetranor PGEM (26B-1a(iii))

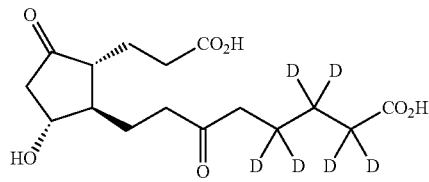

27B 45 mg (0.11 mmol) of protected tetranor PGEM 26B-1a (iii);
5 ml of HOAc/THF/$H_2O$ (4:2:1) mixture.

A solution of protected tetranor PGEM 26B-1a(iii) (in 5 ml of HOAc/THF/$H_2O$ (4:2:1)) was stirred for two days and evaporated with toluene. The remaining residue (40 mg) was purified by flash chromatography:Silica gel (20 g), hexane-ethyl acetate —HOAc 25:75:0.5-hexane-ethyl acetate-HOAc 10:90:0.5. The mass of the collected product (Tetranor PGAM (27(B))) was 14 mg (40%). $R_f$=0.45 (ethanol-ethyl acetate-HOAc 5:95:1).

It is understood for purposes of this disclosure that various changes and modifications may be made to the invention that are well within the scope of the invention. Numerous other changes may be made which will readily suggest themselves to those skilled in the art and which are encompassed in the spirit of the invention disclosed herein.

The list of citations to patents, patent application publications, and publications cited herein are each hereby incorporated by reference in its entirety for all purposes.

What is claimed is:
1. A method for preparing tetranor-PGDM comprising the following reaction steps as shown in Scheme I:

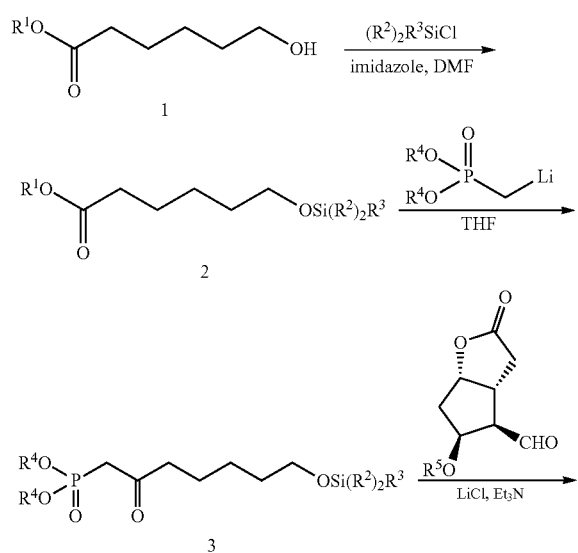

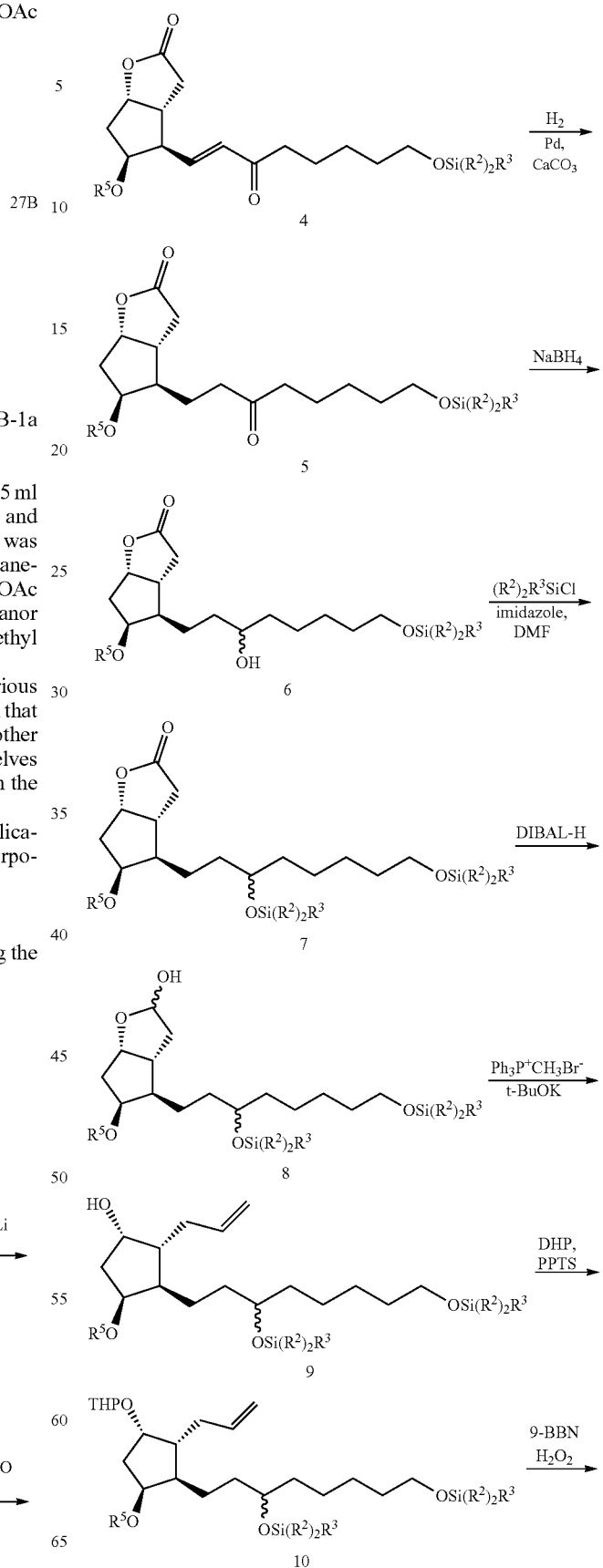

-continued

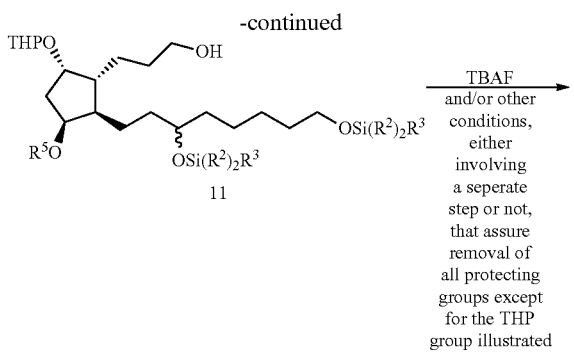
11

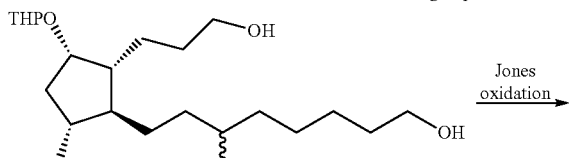
12

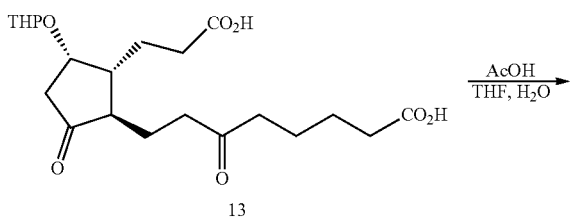
13

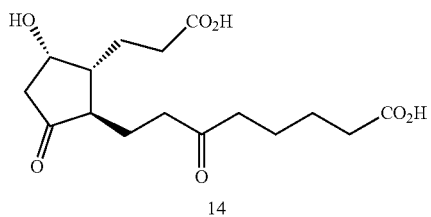
14 wherein
DMF is N,N-dimethylformamide;
THF is tetrahydrofuran;
Et is ethyl
DIBAL is diisobutylaluminum;
t-BuOK is potassium tert-butoxide;
TBAF is tetrabutylammonium fluoride;
THP is tetrahydropyran;
Ac is acetyl;
$R^1$ is $C_{1-4}$ alkyl;
each $R^2$ is independently $C_{1-5}$ alkyl or phenyl;
each $R^3$ is independently a $C_{1-4}$ alkyl;
$R^4$ is methyl or ethyl; and
$R^5$ is a protecting group.

2. The method of claim 1, wherein the protecting group $R^5$ comprises tert-butyldimethylsilyl (TBDMS).

3. The method of claim 1, wherein the protecting group $R^5$ is stable to all reaction conditions between its introduction to the reaction sequence illustrated in Scheme I and its required removal by appropriate deprotection conditions.

4. A method for forming tetranor-PGJM comprising the following reaction steps as shown in Reaction Schemes I and II:

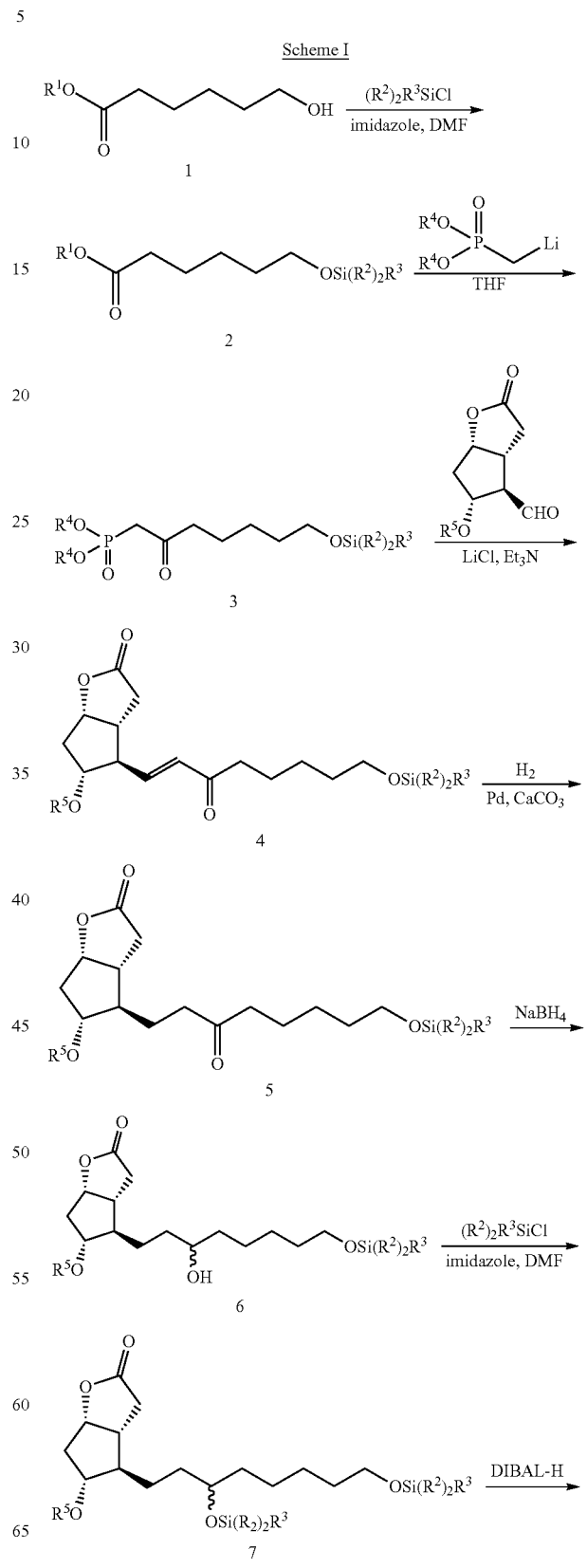

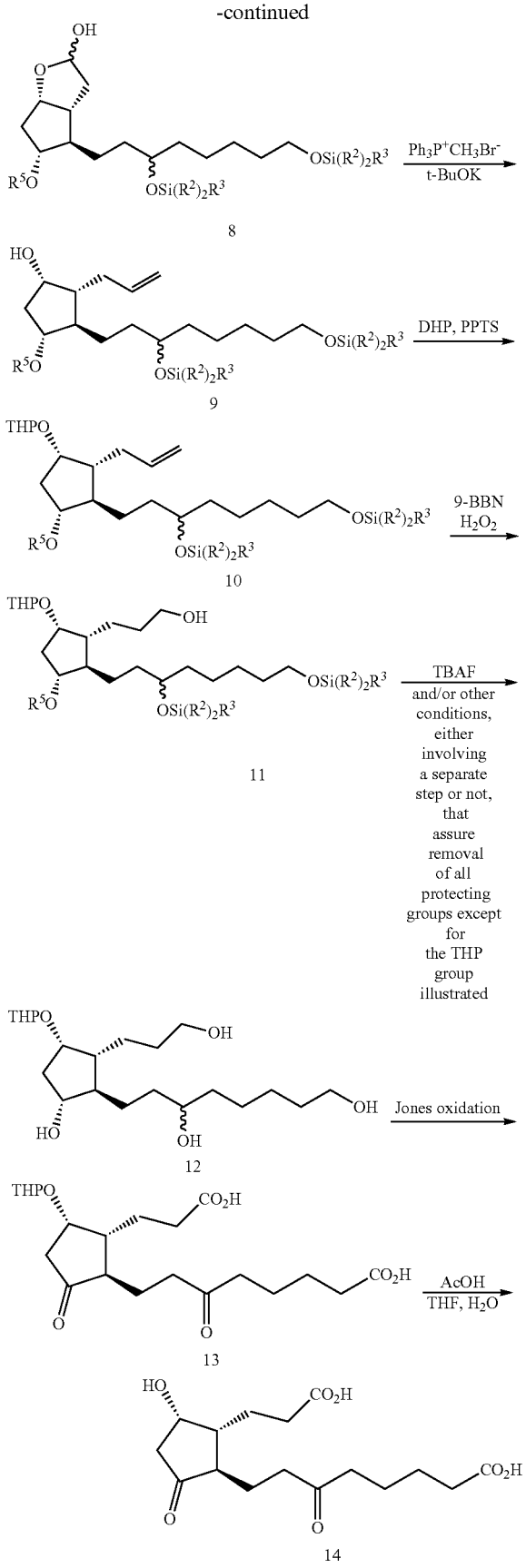

wherein
DMF is N,N-dimethylformamide;
THF is tetrahydrofuran;
Et is ethyl
DIBAL is diisobutylaluminum;
t-BuOK is potassium tert-butoxide;
TBAF is tetrabutylammonium fluoride;
THP is tetrahydropyran;
Ac is acetyl;
$R^1$ is $C_{1-5}$ alkyl;
each $R^2$ is independently $C_{1-5}$ alkyl or phenyl;
each $R^3$ is independently a $C_{1-4}$ alkyl;
$R^4$ is methyl or ethyl; and
$R^5$ is a protecting group; and Scheme II

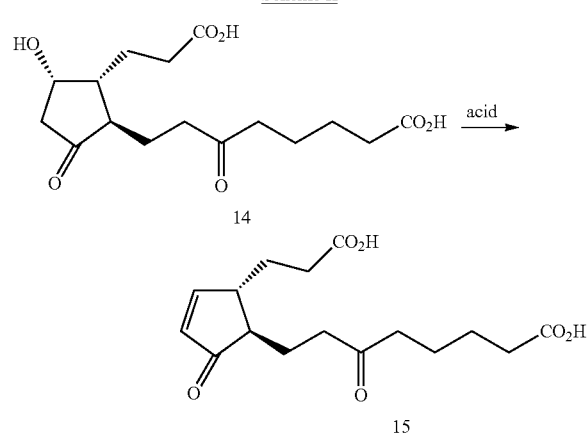

wherein said acid comprises an organic acid or an inorganic acid.

5. The method of claim 4, wherein said acid comprises acetic acid.

6. The method of claim 4, wherein said acid comprises trifluoroacetic acid.

7. A method for forming tetranor-PGEM or tetranor-PGEM-$D_6$ comprising the following reaction steps as shown in Scheme III:

Scheme III

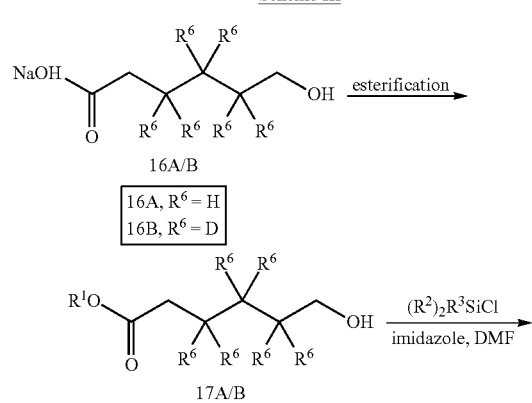

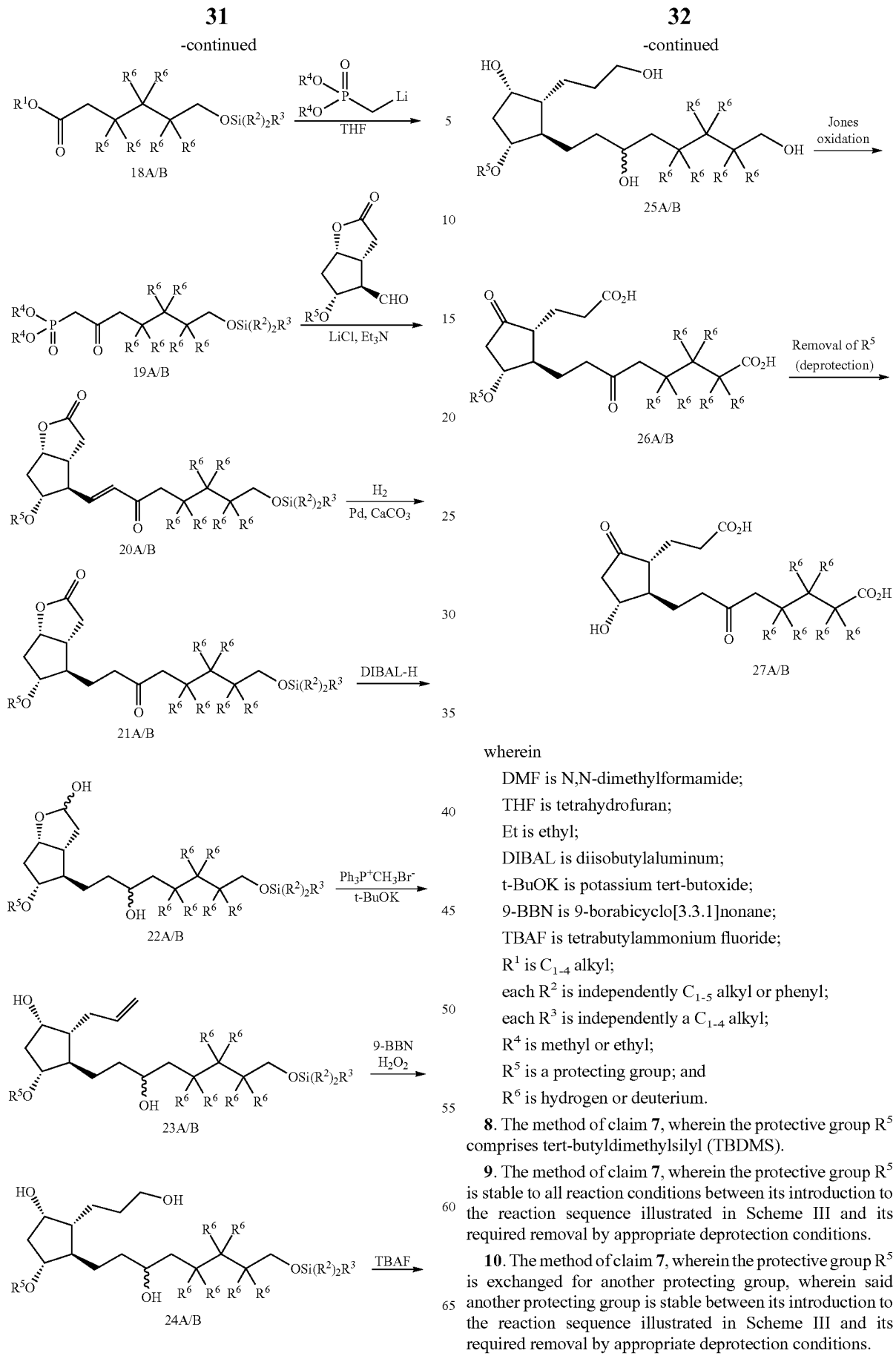

wherein
DMF is N,N-dimethylformamide;
THF is tetrahydrofuran;
Et is ethyl;
DIBAL is diisobutylaluminum;
t-BuOK is potassium tert-butoxide;
9-BBN is 9-borabicyclo[3.3.1]nonane;
TBAF is tetrabutylammonium fluoride;
$R^1$ is $C_{1-4}$ alkyl;
each $R^2$ is independently $C_{1-5}$ alkyl or phenyl;
each $R^3$ is independently a $C_{1-4}$ alkyl;
$R^4$ is methyl or ethyl;
$R^5$ is a protecting group; and
$R^6$ is hydrogen or deuterium.

8. The method of claim 7, wherein the protective group $R^5$ comprises tert-butyldimethylsilyl (TBDMS).

9. The method of claim 7, wherein the protective group $R^5$ is stable to all reaction conditions between its introduction to the reaction sequence illustrated in Scheme III and its required removal by appropriate deprotection conditions.

10. The method of claim 7, wherein the protective group $R^5$ is exchanged for another protecting group, wherein said another protecting group is stable between its introduction to the reaction sequence illustrated in Scheme III and its required removal by appropriate deprotection conditions.

11. A method for forming tetranor-PGAM comprising the following reaction steps as shown in Schemes III and IV:

Scheme III

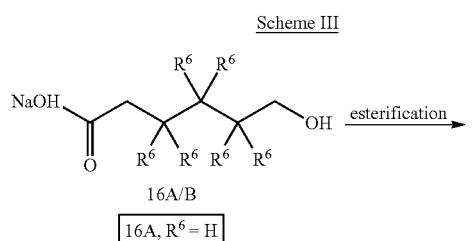

16A, $R^6$ = H
16B, $R^6$ = D

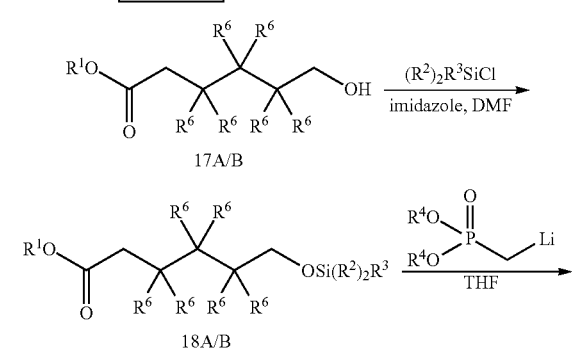

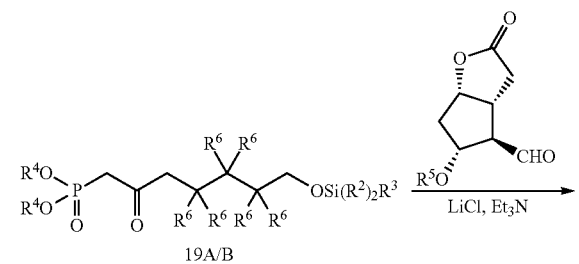

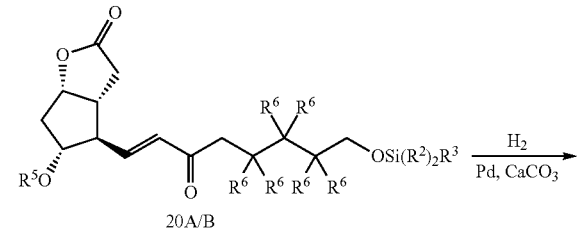

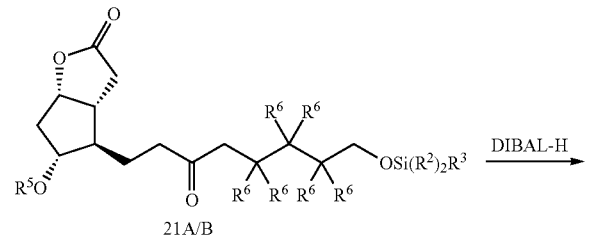

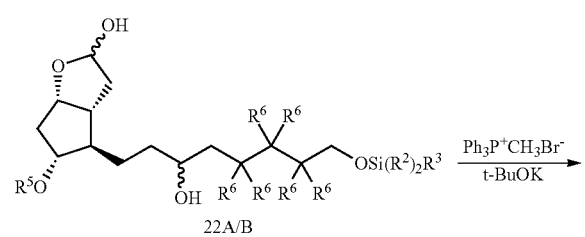

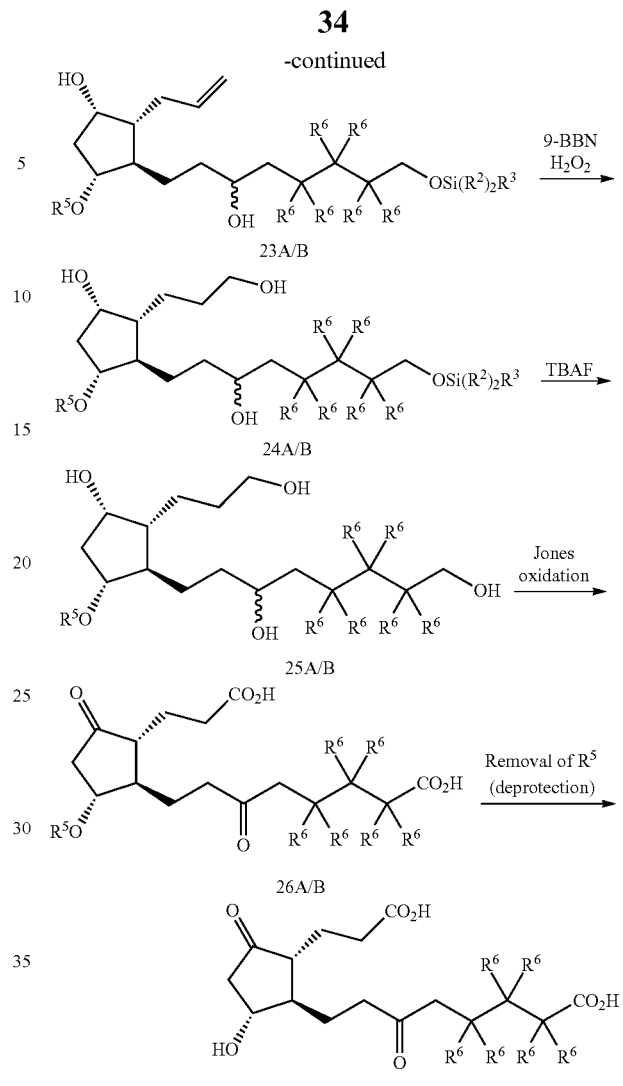

Scheme IV

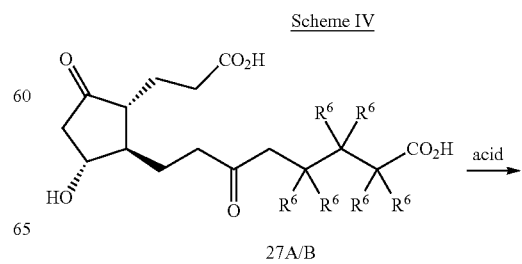

wherein
DMF is N,N-dimethylformamide;
THF is tetrahydrofuran;
Et is ethyl;
DIBAL is diisobutylaluminum;
t-BuOK is potassium tert-butoxide;
9-BBN is 9-borabicyclo[3.3.1]nonane;
TBAF is tetrabutylammonium fluoride;
$R^1$ is $C_{1-4}$ alkyl;
each $R^2$ is independently $C_{1-5}$ alkyl or phenyl;
each $R^3$ is independently a $C_{1-4}$ alkyl;
$R^4$ is methyl or ethyl;
$R^5$ is a protecting group; and
$R^6$ is hydrogen or deuterium; and

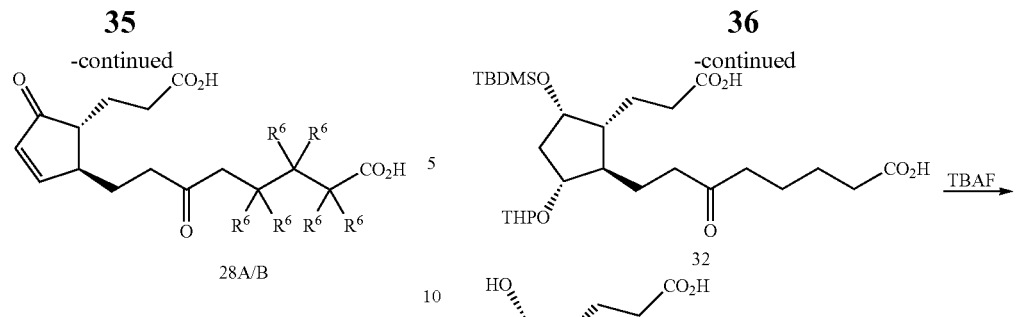

wherein said acid comprises an organic acid or an inorganic acid and wherein $R^6$ comprises hydrogen or deuterium.

12. The method of claim 11, wherein said organic acid comprises trifluoroacetic acid.

13. A method for producing tetranor-PGFM comprising the following steps as shown in Scheme V:

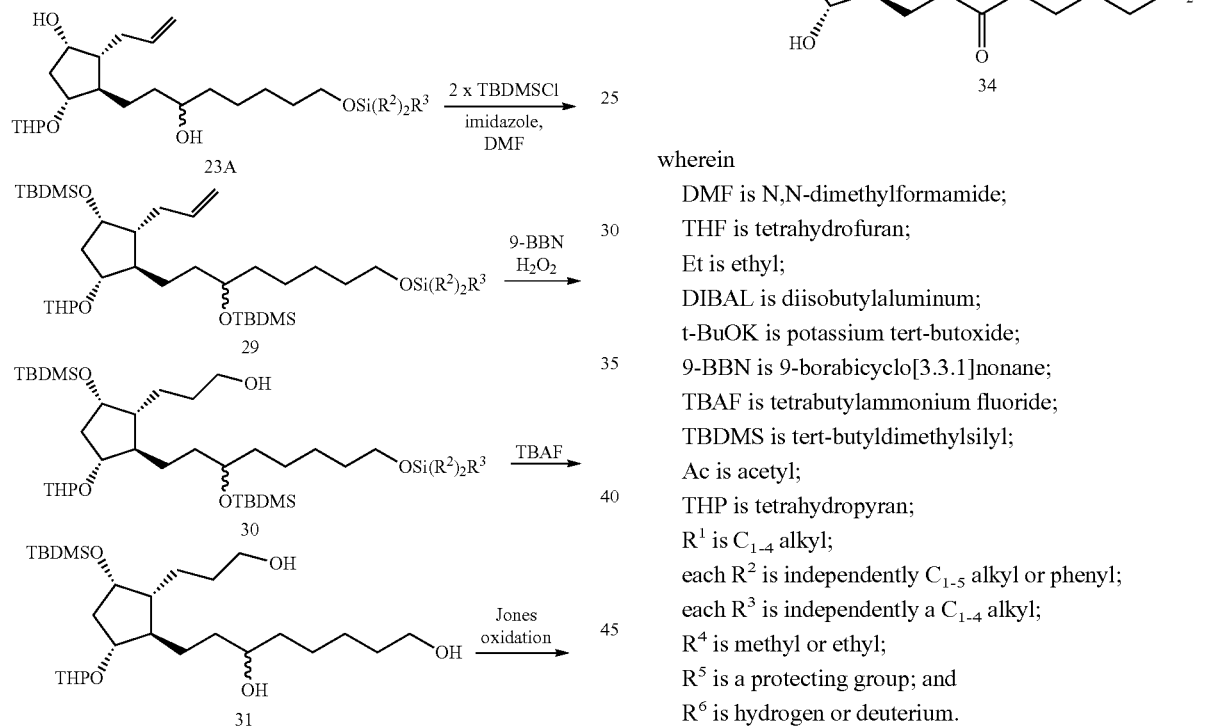

wherein
DMF is N,N-dimethylformamide;
THF is tetrahydrofuran;
Et is ethyl;
DIBAL is diisobutylaluminum;
t-BuOK is potassium tert-butoxide;
9-BBN is 9-borabicyclo[3.3.1]nonane;
TBAF is tetrabutylammonium fluoride;
TBDMS is tert-butyldimethylsilyl;
Ac is acetyl;
THP is tetrahydropyran;
$R^1$ is $C_{1-4}$ alkyl;
each $R^2$ is independently $C_{1-5}$ alkyl or phenyl;
each $R^3$ is independently a $C_{1-4}$ alkyl;
$R^4$ is methyl or ethyl;
$R^5$ is a protecting group; and
$R^6$ is hydrogen or deuterium.

\* \* \* \* \*